United States Patent
Barale et al.

(10) Patent No.: US 9,404,142 B2
(45) Date of Patent: Aug. 2, 2016

(54) **SCREENING METHODS FOR IDENTIFYING *PLASMODIUM* PROTEASES INHIBITORS**

(75) Inventors: Jean-Christophe Barale, Vanves (FR); Anthony Bouillon, Paris (FR); David Giganti, Paris (FR); Olivier Louis Gabiel Gorgette, Paris (FR); Veronique Stoven, Paris (FR); Michael Nilges, Voisins les Bretonneux (FR); Odile Puijalon, Issy les Moulineaux (FR)

(73) Assignee: Institut Pasteur, Paris (FR)

( * ) Notice: Subject to any disclaimer, the term of this patent is extended or adjusted under 35 U.S.C. 154(b) by 328 days.

(21) Appl. No.: 13/989,844

(22) PCT Filed: Nov. 29, 2010

(86) PCT No.: PCT/IB2010/003423
§ 371 (c)(1),
(2), (4) Date: Jan. 6, 2014

(87) PCT Pub. No.: WO2012/073066
PCT Pub. Date: Jun. 7, 2012

(65) Prior Publication Data
US 2014/0134657 A1    May 15, 2014

(51) Int. Cl.
*C07K 7/06* (2006.01)
*C07K 7/08* (2006.01)
*C07K 14/00* (2006.01)
*C12Q 1/37* (2006.01)
*G01N 33/569* (2006.01)

(52) U.S. Cl.
CPC ... *C12Q 1/37* (2013.01); *C07K 7/06* (2013.01); *C07K 7/08* (2013.01); *C07K 14/00* (2013.01); *G01N 33/56905* (2013.01)

(58) Field of Classification Search
None
See application file for complete search history.

(56) References Cited

FOREIGN PATENT DOCUMENTS

WO    2006/120579 A2    11/2006

OTHER PUBLICATIONS

Hertzberg et al., "High-throughput screening: new technology for the 21st century", Current Opinion in Chemical Biology, 2000, pp. 445-451.*
Pattanaik et al., "Stage-specific profiling of Plasmodium falciparum proteases using an internally quenched multispecificity protease substrate", Biochemical and Biophysical Research Communications, 2003, pp. 974-979.*
Carlton., substilisin-like protease precursor [Plasmodium vivax Sal-1]; NCBI Reference Sequence: XP_001613247.1; direct submission, 2008; pp. 1-2.*
Michael J. Blackman, et al., "Structural and Biochemical Characterization of a Fluorogenic Rhodamine-Labeled Malarial Protease Substrate," Biochemistry 2002, 41, 12244-12252.
Jane M. Carlton, et al., "Comparative genomics of the neglected human malaria parasite Plasmodium vivax," Nature, vol. 455, Oct. 9, 2008, pp. 757-763.
Philip J. Rosenthal, "Cysteine proteases of malaria parasites," International Journal for Parasitology 34 (2004) 1489-1499.
Chrislaine Withers-Martinez, et al., "Subtilisin-like proteases of the malaria parasite," Molecular Microbiology (2004) 53 (1), 55-63.

* cited by examiner

*Primary Examiner* — Lianko Garyu
(74) *Attorney, Agent, or Firm* — Law Office of Salvatore Arrigo and Scott Lee, LLP

(57) ABSTRACT

The invention relates to the field of parasitology. Methods and peptidic substrate for screening and identifying inhibitors of *Plasmodium* are described. Also described are compounds identified by these screening methods, including more particularly inhibitors of *Plasmodium* subtilisin-like proteases. The invention also concerns anti-malaria compounds, anti-malaria compositions, and uses thereof for preventing, treating, improving, and/or alleviating a *Plasmodium* infection in a subject, and more *Plasmodium vivax* and/or by *Plasmodium falciparum* human infections.

14 Claims, 15 Drawing Sheets

```
PBSUB1        ---------------------------------KIIEDLRFLEKVDAILENG
PYSUB1        -----MGFSKMRREFIYGQVMSLADCTISAHNDLMNKEKDVEKIIEDLRFLEKVDAILENG
PBSUB1-SAL1   MMITRRAAILCPWVIQLVIKRTLAGDILPNEGKREKDDVSKIISELRFILKVEIILESS
PVSUB1-BELEM  MMITRRAAILCPWVIQLVIKRTLAGDILPNEGKREKDDVSKIISELRFILKVEIILESS
PFSUB1-3D7    MMINKKVVAICTLTLHLFCIFLCIGKEVRSHENGKIQDDAKKIMSELRFLEKVEDVIEKG

PBSUB1        NMTIDDVKADADAYNPDEDAPKEE---------INKIEMEKNAEEEAKN----------G
PYSUB1        NMTIDDVEDGDAYNPDEDAPKEE---------INKIEMEKNAEEEEKH----------G
PBSUB1-SAL1   NMSVSDVEADANAYNPDRDAPKEE-----LDKLIDDDEIPSDDHNLEN----------G
PVSUB1-BELEM  NMSVSDVEADANAYNPDRDAPKEE-----LDKLIDDDEIPSDDHNLEN----------G
PFSUB1-3D7    NLGGNEIDADIHSENPDIEMILEEIEEIKMREDNLVKEEKMENDHNNINNNISSSSSS

PBSUB1        KKRIIEDYLLDEKKKKSLRLIVSENHATSPSFFEESILQEDIMSFIQSKGHIVNLKNLKS
PYSUB1        KKRIIEKDLLNEKKNKSLRLIVSENHATIPSFFEESILQEDIMSFIQSKGHIVNLKNIKS
PBSUB1-SAL1   PCRRAEKKESPGKNKKSLRLIVSENHATSPSFFEESLLQEDVISFIQSKGKLSNLKNLKS
PVSUB1-BELEM  PCRRAEKKESPGKNKKSLRLIVSENHATSPSFFEESLLQEDVISFIQSKGKLSNLKNLKS
PFSUB1-3D7    SNIFQDEKEEVSKKKRNLRLIVSENHATIPSFFQESLIIPDVISFLESKGNLSNLKNING

PBSUB1        MIIELNSDMTDEIEAYILLIKKGAHMESILVGADSIMDIIKDAVKRGDISINIKGM
PYSUB1        MIIELNSDMTDEIETYILLIKKGAHMESILVGADSIMDIIKDAVKRGDISINIKII
PBSUB1-SAL1   MIIDLNSDMTDEEIAEIISLLERKGALIESDKLVGADDVSLASVKDAVRRGESSIMKEL
PVSUB1-BELEM  MIIDLNSDMTDEEIAEIISLLERKGALIESDKLVGADDVSLASVKDAVRRGESSIMKEL
PFSUB1-3D7    MIIELKEDITDEEIISYIKILERKGALIESDKLVSADNIDISGIKDAIRRGEENIDVNDY

PBSUB1        QSNMLEVEN----------------------------------------
PYSUB1        QSNMLEVEN----------------------------------------
PBSUB1-SAL1   RSIMLEVPS--------GESPPSHAASS---------GSP---------EH
PVSUB1-BELEM  RSIMLEVPS--------GESPPSHAASS---------GSP---------EH
PFSUB1-3D7    KSI-MLEVENDAEDYDKMEGMFNESHAATSKRKRHSTNERGYDTFSSESYKTYSKSDYIK

PBSUB1        ---------KTYEKINNNEKSKNSYK------KSFNDEYRNLQWGLDLARLIDACEMIT
PYSUB1        ---------NTYEKINNKEKSKNSDK------KSYNDEYRNLQWGLDLARLIDACEMIT
PBSUB1-SAL1   DDDDLLSEAAIEREEAIIAGSKIIKG------YKFNDEYRNLQWGLDLARLDETQELIN
PVSUB1-BELEM  DDDDLLSEAAIEREEAIIAGSKIIKG------YKFNDEYRNLQWGLDLARLDETQELIN
PFSUB1-3D7    DDNNNNYYYSISGNIEINSSSENLSSSRSRPGKYFNDEYRNLQWGLDISRLDETQELIN
```

*FIG. 1C*

```
PBSUB1        TNSVETTKICVIDSGIDYNHPDLKCNIMVNLEIGKEGIDDDNNGIIDDIYGVNMVNNI
PYSUB1        TNSVRTTKMCVIDSGIDYNHPDLKCNIMVNLKEIGKPGVDDDNNGIIDDIYGANMVNNI
PBSUB1-SAL1   ANRVSVTKICVIDSGIDYNHPDIRNNIDVNMKELHGRKGVDDDSNGIVDDVYGANFVNNS
PVSUB1-BELEM  ANRVSVTKICVIDSGIDYNHPDIRNNIDVNMKELHGRKGVDDDSNGIVDDVYGANFVNNS
PFSUB1-3D7    EHQVMSTRICVIDSGIDYNHPDLKDNIEINLKELHGRKGIDDDNNGIVDDIYGANFVNNS

PBSUB1        GDPMDDHNEGSHVSGIISAIGNNSIGVVGVNPSSKLVICKALDDKKLGRLGNIFKCIDYC
PYSUB1        GDPMDDHNHGTHVAGIISAIGNNSIGVVGVNTNSKLVICKALDDKKLGRLGNIFKCIDYC
PBSUB1-SAL1   GDPMDDNYHGTHVSGIISAVGNNGIGVVGVBGHSKLVICKALDCHKLGRLGDM--C----
PVSUB1-BELEM  GDPMDDNYHGTHVSGIISAVGNNGIGVVGVBGHSKLVICKALDCHKLGRLGDMFKCIDYC
PFSUB1-3D7    GNPMDDNYHGTHVSGIISAIGNNNIGVVGVDVNSKLIICKALDEHKLGRLGDMFKCLDYC

PBSUB1        INKKVNINGSESFDEYSTIESSIIEYIARLGILFMVSSSNCSHPPSSIPDITRCDLSVN
PYSUB1        INNKANINGSESFDEYSTVESSIIEYIGRLGILFMVSSSNCSHPSSIPDITRCDLSVN
PBSUB1-SAL1   ----AHMINGSFSFDEYSNIFNASVEHLRSLGILFFVSASNCAHLKLSKPDIAKCDLAVN
PVSUB1-BELEM  ISRQAHMINGSFSFDEYSNIFNASVEHLRSLGILFFVSASNCAHLKLSKPDIAKCDLAVN
PFSUB1-3D7    ISRNAHMINGSFSFDEYSGIFNSSVEYLQRKGILFFVSASNCSHPKSSIPDIRKCDLSIN

PBSUB1        SKYPSVLSTLYDNMVVANLKK-KINGELDISINSFYSILYCQMSAPGANIYSTASRGSY
PYSUB1        SKYPSVLSTLYDNVMVANLKK-KKNGELDMSINSFYSILYCQMSAPGANIYSTATRGSY
PBSUB1-SAL1   HRVPPILSKTHNNVIAVANLKR-DLDESYSLSVNSFYSNIYCOLAAPGTNIYSTIEMNNI
PVSUB1-BELEM  HRVPPILSKTHNNVIAVANLKR-DLDESYSLSVNSFYSNIYCOLAAPGTNIYSTIEMNNI
PFSUB1-3D7    AKYPPILSTVYDNVISVANLKKNDNNHYSLSINSFYSNKYCQLAAPGTNIYSTAHNSY

PBSUB1        MEXSGTSMAAPHVALIASIIISINFDLTYKQVVNILKNSMVKISSHKNKIAWGGYIDIIN
PYSUB1        LELSGTSMAAPHVALIASIIISINFDLTYKQVVSILKNSMVKISSHKNKIAWGGYIDIIK
PBSUB1-SAL1   RKLNGTSMASPHVAAIASIVPSINFNLTYLQVPIIRNAIVKLPSIIERVSWGGYMDIIR
PVSUB1-BELEM  RKLNGTSMASPHVAAIASIVRSINFNLTYLQVPIIRNAIVKLPSIIERVSWGGYMDIIR
PFSUB1-3D7    RKLNGTSMAAPHVAAIASLIPSINFDISYKMVIQILKDSIVMLPSLKNMVANAGYADINK

PBSUB1        AVKNAISSKNS-IIFFQGIRMWKSKKN--
PYSUB1        AVKNAISSKNS-YIFQGISIWKNKKN---
PBSUB1-SAL1   AVNLAIDSKAAPYIKSHSWFRWKQGSRR-
PVSUB1-BELEM  AVNLAIDSKAAPYIKSHSWFRWKQGSRR-
PFSUB1-3D7    AVNLAIKSKKT-YINSISNKWKKSEYLH
```

*FIG. 1C*
*(CONT.)*

FIGURE 4A: *Plasmodium vivax* SUB1-Belem (*Pv*SUB1-Belem) nucleotide sequence

```
   1 agaattcgcc cttggtaact cctgcacagc aacgcaatgg tgctgacgcg aagagcagcg
  61 ctcctcctgt gcccctgggt aatccaactg gtaatcaagc gaaccctcgc aggggacatc
 121 ctgccgaatg agggcaagaa ggaaaaggat gatgtgcata aaattataag cgagttgcgc
 181 ttcctacaga aggtagaaac cattttggag agcagcaaca tgagcgtttc agatgtggag
 241 gcagatgcga atgcgtataa tcctgatagg gacgcccta aagaggagct gcagaagctc
 301 caagaccagc aggaaacccc ctcgaagcag cctaataacc tacggaatag cccccaaaaa
 361 agagcagaaa aaaaagagtc acctgggaaa aataaaaagt cgttacgctt aattgtgagt
 421 gagaaccacg ccacgagtcc ctccttcttc gaggagtctc tccttcaaga agacgtggtg
 481 agcttcatcc agagcaaagg gaagctatcc aatctgaaga atctaaaatc gatgataatc
 541 gatttgaaca gcgacatgac ggatgaggag ttggcagagt acattagcct gttggagagg
 601 aagggggcgt tgatagaatc tgacaagctc gtggggcgg acgacgtgag ccttgcatct
 661 gtaaaggatg cggtcaggcg cggggagagt agcgtcaatt ggggtaaact ccgcagcacc
 721 atgttggagg ttccaagcgg ggagtccccc cccagccacg ccgctagcag tggcagcccc
 781 ttcgatgacg atgatgacct cctgtcggag gcggccctcc acagggagga agcccacctg
 841 gcggggagca aaaccaccaa ggggtacaaa ttcaacgatg agtacaggaa cctgcagtgg
 901 gggttggacc tcgccaggct agacgaaacg caggatctta taaacgcaaa ccgagtgagc
 961 gtaaccaaaa tctgcgtaat tgacagcggg atcgattaca accaccccga cttgaggaac
1021 aacatagatg tgaatgtgaa agagctgcac ggaagaaaag gagtggacga tgatagcaac
1081 ggagtcgtgg acgatgtgta tggagccaat tttgtaaaca acagtggaga tcctatggat
1141 gataattacc acggaacgca tgtctctgga atcatttccg ccgttgggaa taatggcata
1201 ggtatagtgg gggtagatgg gcactctaag ctagtcatat gtaaggcact agatcaacac
1261 aagctgggac gactagggga catgttcaaa tgcattgact actgcataag cagacaggca
1321 catatgatta atggtagctt ttcatttgac gagtatagca atatctttaa tgcgtctgtg
1381 gagcacctac gatctctggg aattcttttc ttcgtctcgg ccagcaactg tgcacatgat
1441 aagctctcca accggacat tgccaaatgc gacctcgccg ttaatcatag gtaccctccc
1501 atcttgtcta aaacgcacaa caatgtaatc gctgttgcga atttgaagag agacctagat
1561 gagagctact ccctctctgt taactccttt tacagtaata tttattgcca gttggctgct
1621 ccggggacta atatatattc taccacgcct atgaataact atcggaagct caatggcact
1681 tccatggcat ctccgcacgt ggctgcaatc gcctccatcg ttaggtctat caaccctaat
1741 ttgacttacc tgcaaattgt cgaaattttg aggaacgcca ttgtgaagct ccctcctc
1801 accgagaggg tctcgtgggg aggctacgtc gacatcctgc gcgccgtcaa cctggccatc
1861 gactccaagg cggcgccta catcaagtcg cactcctggt tcaggtggaa cagggcagt
1921 aggcggtagg cggtggacgg tggacggtgg gcggtgggcg gtggagcggt aaagcggtgg
1981 agcggcacgc gacagggcaa cagagcaaca gagcaacaga gcggcgtcac atcagagcga
2041 ccgcgcaaca
```

FIGURE 4B: *Plasmodium vivax* SUB1-Belem (*Pv*SUB1-Belem) full length amino acid sequence

```
MVLTRRAALLLCPWVIQLVIKRTLAGDILPNEGKKEKDDVHKIISELRFLQKVETILESSNMSVSD
VEADANAYNPDRDAPKEELQKLQDQQETPSKQPNNLRNSPQKRAEKKESPGKNKKSLRLIVSENHA
TSPSFFEESLLQEDVVSFIQSKGKLSNLKNLKSMIIDLNSDMTDEELAEYISLLERKGALIESDKL
VGADDVSLASVKDAVRRGESSVNWGKLRSTMLEVPSGESPPSHAASSGSPFDDDDDLLSEAALHRE
EAHLAGSKTTKGYKFNDEYRNLQWGLDLARLDETQDLINANRVSVTKICVIDSGIDYNHPDLRNNI
DVNVKELHGRKGVDDDSNGVVDDVYGANFVNNSGDPMDDNYHGTHVSGIISAVGNNGIGIVGVDGH
SKLVICKALDQHKLGRLGDMFKCIDYCISRQAHMINGSFSFDEYSNIFNASVEHLRSLGILFFVSA
SNCAHDKLSKPDIAKCDLAVNHRYPPILSKTHNNVIAVANLKRDLDESYSLSVNSFYSNIYCQLAA
PGTNIYSTTPMNNYRKLNGTSMASPHVAAIASIVRSINPNLTYLQIVEILRNAIVKLPSLTERVSW
GGYVDILRAVNLAIDSKAAPYIKSHSWFRWKQGSRR
```

FIGURE 4C: Recombinant *Plasmodium vivax* SUB1-Belem (*Pv*SUB1-Belem) full length amino acid sequence

```
MLLVNQSHQGFNKEHTSKMVSAIVLYVLLAAAAHSAFAADPGDILPNEGKKEKDDVHKIISELRFL
QKVETILESSNMSVSDVEADANAYNPDRDAPKEELQKLQDQQETPSKQPNNLRNSPQKRAEKKESP
GKNKKSLRLIVSENHATSPSFFEESLLQEDVVSFIQSKGKLSNLKNLKSMIIDLNSDMTDEELAEY
ISLLERKGALIESDKLVGADDVSLASVKDAVRRGESSVNWGKLRSTMLEVPSGESPPSHAASSGSP
FDDDDDLLSEAALHREEAHLAGSKTTKGYKFNDEYRNLQWGLDLARLDETQDLINANRVSVTKICV
IDSGIDYNHPDLRNNIDVNVKELHGRKGVDDDSNGVVDDVYGANFVNNSGDPMDDNYHGTHVSGII
SAVGNNGIGIVGVDGHSKLVICKALDQHKLGRLGDMFKCIDYCISRQAHMINGSFSFDEYSNIFNA
SVEHLRSLGILFFVSASNCAHDKLSKPDIAKCDLAVNHRYPPILSKTHNNVIAVANLKRDLDESYS
LSVNSFYSNIYCQLAAPGTNIYSTTPMNNYRKLNGTSMASPHVAAIASIVRSINPNLTYLQIVEIL
RNAIVKLPSLTERVSWGGYVDILRAVNLAIDSKAAPYIKSHSWFRWKQGSRRHHHHHH
```

FIGURE 4D: Amino acid sequence of the recombinant enzymatically active form of *Plasmodium vivax* SUB1-Belem (*Pv*SUB1-Belem), following auto-maturation at the KLVGAD//DVSLA site.

```
DVSLASVKDAVRRGESSVNWGKLRSTMLEVPSGESPPSHAASSGSPFDDDDDLLSEAALHREEAHL
AGSKTTKGYKFNDEYRNLQWGLDLARLDETQDLINANRVSVTKICVIDSGIDYNHPDLRNNIDVNV
KELHGRKGVDDDSNGVVDDVYGANFVNNSGDPMDDNYHGTHVSGIISAVGNNGIGIVGVDGHSKLV
ICKALDQHKLGRLGDMFKCIDYCISRQAHMINGSFSFDEYSNIFNASVEHLRSLGILFFVSASNCA
HDKLSKPDIAKCDLAVNHRYPPILSKTHNNVIAVANLKRDLDESYSLSVNSFYSNIYCQLAAPGTN
IYSTTPMNNYRKLNGTSMASPHVAAIASIVRSINPNLTYLQIVEILRNAIVKLPSLTERVSWGGYV
DILRAVNLAIDSKAAPYIKSHSWFRWKQGSRRHHHHHH
```

FIGURE 5A : recombinant *Plasmodium falciparum* SUB1 (*Pf*SUB1) recodoned nucleotide sequence

```
   1 ttactgtttt cgtacagttt tgtaataaaa aaacctataa atattccgga ttattcatac
  61 cgtcccacca tcgggcgcgg atctatgcta ctagtaaatc agtcacacca aggcttcaat
 121 aaggaacaca caagcaagat ggtaagcgct attgttttat atgtgctttt ggcggcggcg
 181 gcgcattctg cctttgcggc ggatcttgga tctaaggagg tgagatccga agagaacggc
 241 aaaatacaag acgatgcgaa gaaaatagtg agcgagctcc ggtttcttga gaaggttgaa
 301 gacgtcattg agaaaagcaa tataggaggc aacgaggtgg atgcagacga gaatagtttc
 361 aaccctgata cagaagtgcc catcgaggag atagaagaga tcaagatgcg agagctgaag
 421 gacgtcaaag aggaaaagaa taaaaacgat aatcacaaca ataataataa caatattagt
 481 agttccagtt cttccagtag caacacgttt ggagaggaaa aagaagaggt tagtaagaaa
 541 aaaaagaaac tgagactgat cgtgtcagag aatcatgcaa ctaccectag cttcttccag
 601 gaatccctgc tcaaccaga cgtcttgagc tttctggaat caaagggcaa cctgagcaat
 661 ctgaagaaca tcaattccat gattattgaa ctcaaggaag acaccaccga cgatgaactc
 721 atctcttata tcaagatttt ggaggagaaa ggagctctca tcgagtccga taagctggtt
 781 agtgcagaca acatcgatat tccggtatc aaggatgcca tacgcagggg agaggaaaac
 841 atcgatgtga atgattacaa gagcatgctt gaagtggaaa atgatgccga agactatgat
 901 aaaatgtttg gaatgttcaa cgagagccat gccgccacaa gtaagcggaa aagacactcc
 961 acaaacgaga ggggctacga cacttttagc tcacctagtt ataagaccta ctccaagtct
1021 gactacctgt acgacgacga caacaataac aataactact actacagcca ttccagcaat
1081 ggacataatt cctcaagtcg aaatagctct agctcacgca gtaggccagg caaataccac
1141 tttaacgacg agttcagaaa cctgcaatgg ggactggact tgtcacgact cgacgagact
1201 caggaattga tcaacgagca ccaggtgatg tccactcgga tttgcgtcat agactccgga
1261 attgattata accaccctga cctgaaggac aatatcgagc ttaatctgaa ggaactccac
1321 gggaggaagg gatttgatga tgataataat ggcatcgtgg acgacatcta cggtgccaat
1381 ttcgtgaata acagcgggaa cccgatggac gataactatc atggtacgca cgtttctggc
1441 atcatcagcg ccatcggcaa taacaacatt ggagtagttg gtgtagatgt caactcaaaa
1501 ttgatcatct gtaaggccct tgacgaacac aaacttggac ggctgggcga tatgttcaag
1561 tgccttgact attgcatatc taggaatgcc cacatgataa acggctcatt ctcattcgac
1621 gagtactctg ggatctttaa ctcttcagtg gagtatcttc agcgcaaagg aatactcttc
1681 tttgtcagcg caagcaattg ttcacacccc aagtcttcta cacctgatat tcggaagtgt
1741 gacctgagca ttaacgctaa gtacccaccc atcctgtcaa ctgtgtacga taatgtcatc
1801 agcgtggcta atctgaaaaa gaacgacaac aacaatcact atagtctttc tatcaactct
1861 ttctattcta acaaatattg ccagttggcg gctccaggca ccaatatcta tagcacagca
1921 ccccataact catatagaaa actcaacggg acctctatgg ctgcacccca cgtagccgct
1981 attgcctccc tgattttcag cattaaccca gatttgtcct acaaaaaggt cattcagatt
2041 ctgaaggact ccatagttta cttgccctcc ttgaagaaca tggtggcatg ggccggttac
2101 gctgatatta ataaggccgt gaaccttgct atcaaatcca agaaaaccta cattaattca
2161 aatattagca acaaatggaa gaaaaaatct cggtatctgc atcaccatca tcaccactga
2221 agatcccggg ccatgggaat ccggagcggc cgc
```

FIGURE 5B: recombinant *Plasmodium falciparum* SUB1 (*Pf*SUB1) amino acid sequence <u>MLLVNQSHQGFNKEHTSKMVSAIVLYVLLAAAAHSAFAA</u>DLGSKEVRSEENGKIQDDAKKIVSELR
FLEKVEDVIEKSNIGGNEVDADENSFNPDTEVPIEEIEEIKMRELKDVKEEKNKNDNHNNNNNNIS
SSSSSSSNTFGEEKEEVSKKKKKLRLIVSENHATTPSFFQESLLEPDVLSFLESKGNLSNLKNINS
MIIELKEDTTDDELISYIKILEEKGALIESDKLVSADNIDISGIKDAIRRGEENIDVNDYKSMLEV
ENDAEDYDKMFGMFNESHAATSKRKRHSTNERGYDTFSSPSYKTYSKSDYLYDDDNNNNNYYYSHS
SNGHNSSSRNSSSSRSRPGKYHFNDEFRNLQWGLDLSRLDETQELINEHQVMSTRICVIDSGIDYN
HPDLKDNIELNLKELHGRKGFDDDNNGIVDDIYGANFVNNSGNPMDDNYHGTHVSGIISAIGNNNI
GVVGVDVNSKLIICKALDEHKLGRLGDMFKCLDYCISRNAHMINGSFSFDEYSGIFNSSVEYLQRK
GILFFVSASNCSHPKSSTPDIRKCDLSINAKYPPILSTVYDNVISVANLKKNDNNNHYSLSINSFY
SNKYCQLAAPGTNIYSTAPHNSYRKLNGTSMAAPHVAAIASLIFSINPDLSYKKVIQILKDSIVYL
PSLKNMVAWAGYADINKAVNLAIKSKKTYINSNISNKWKKKSRYL<u>HHHHHH</u>

FIGURE 6A : recombinant *Plasmodium berghei* SUB1 (*Pb*SUB1) recodoned nucleotide sequence

```
                                          ATGCTACTAGTAAATCA
GTCACACCAAGGCTTCAATAAGGAACACACAAGCAAGATGGTAAGCGCTA
TTGTTTTATATGTGCTTTTGGCGGCGGCGGCGCATTCTGCCTTTGCGGCG
GATCCGcacaacgacctgatgaacaaggagaaggacgtgcagaagatcat
cgaggacctcaggttcctggagaaggtggacgctatcctggagaactcca
acatgactatcgacgacgtgaaggccgacgctgacgcttacaaccctgac
gaggacgcccctaaggaggagctgaacaagatcgagatggagaagaagaa
ggctgaggaggaggctaagaactctaagaagaagatcctggagaggtacc
tcctggacgagaagaagaagaagtccctgaggctgatcgtgtccgagaac
cacgctacttctccttccttcttcgaggagagcctgatccaggaggactt
catgtccttcatccagtccaagggcgagatcgtgaacctgaagaacctga
agagcatgatcatcgagctcaacagcgacatgaccgacaaggagctcgag
gcctacatcactctgctgaagaagaagggtgctcacgtcgagtctgacga
gctggtgggagctgactccatctacgtcgacatcatcaaggacgctgtga
agcgtggcgacacctccatcaacttcaagaagatgcagtccaacatgctg
gaggtcgagaacaagacctacgagaagctcaacaacaacctcaagaagag
caagaacagctacaagaagagcttcttcaacgacgagtaccgcaacctcc
agtggggactggacctggcccgcctggacgacgctcaggagatgatcacc
accaacagcgtggagactaccaagatctgcgtgatcgactccggaatcga
ctacaaccacccgacctgaagggcaacatctacgtgaacctgaacgagc
tcaacggcaaggagggtatcgacgacgacaacaacggcatcatcgacgac
atctacggagtgaactacgtgaacaacaccggtgacccttgggacgacca
caaccacggttctcacgtgagcggaatcatctccgctatcggtaacaact
ccatcggtgtggtcggtgtcaaccctcctctaagctcgtcatctgcaag
gctctggacgacaagaagctcggaaggctgggcaacatcttcaagtgcat
cgactactgcatcaacaagaaggtcaacatcatcaacggctccttctcct
tcgacgagtactccaccatcttctcctccactatcgagtacctcgcccgt
ctcggcatcctgttcgtggtctccagctccaactgcagccaccccccctc
ctccatccctgacatcactcgctgcgacctgtccgtcaactccaagtacc
cctccgtgctgtccacccagtacgacaacatggtggtggtcgctaacctg
aagaagaagatcaacggcgagtacgacatctccatcaactccttctactc
tgacatctactgccaggtctccgctcccggcgctaacatctactccaccg
cttcccgcggttcttacatggagctgtccggaacttccatggctgcccct
cacgtggctggtatcgcttccatcatcctgtctatcaaccctgacctgac
ctacaagcaggtggtgaacatcctcaagaacagcgtggtgaagctgagca
gccacaagaacaagatcgcctggggtggttacatcgacatcctgaacgct
gtcaagaacgccatctctagcaagaactcttacatcaggttccagggtat
caggatgtggaagagcaagaagcgtaacgctgctcaccaccaccaccacc
actaagaattc
```

FIGURE 6B: recombinant *Plasmodium berghei* SUB1 (*Pb*SUB1) amino acid sequence

```
MLLVNQSHQGFNKEHTSKMVSAIVLYVLLAAAAHSAFAADP
HNDLMNKEKDVQKIIEDLRFLEKVDAILENSNMTIDDVKADADAYNPD
EDAPKEELNKIEMEKKKAEEEAKNSKKKILERYLLDEKKKKSLRLIVSEN
HATSPSFFEESLIQEDFMSFIQSKGEIVNLKNLKSMIIELNSDMTDKELE
AYITLLKKKGAHVESDELVGADSIYVDIIKDAVKRGDTSINFKKMQSNML
EVENKTYEKLNNNLKKSKNSYKKSFFNDEYRNLQWGLDLARLDDAQEMIT
TNSVETTKICVIDSGIDYNHPDLKGNIYVNLNELNGKEGIDDDNNGIIDD
IYGVNYVNNTGDPWDDHNHGSHVSGIISAIGNNSIGVVGVNPSSKLVICK
ALDDKKLGRLGNIFKCIDYCINKKVNIINGSFSFDEYSTIFSSTIEYLAR
LGILFVVSSSNCSHPPSSIPDITRCDLSVNSKYPSVLSTQYDNMVVVANL
KKKINGEYDISINSFYSDIYCQVSAPGANIYSTASRGSYMELSGTSMAAP
HVAGIASIILSINPDLTYKQVVNILKNSVVKLSSHKNKIAWGGYIDILNA
VKNAISSKNSYIRFQGIRMWKSKKRNAAHHHHHH
```

SCREENING METHODS FOR IDENTIFYING *PLASMODIUM* PROTEASES INHIBITORS

FIELD OF THE INVENTION

The invention relates to the field of parasitology. More particularly, it relates to the identification of inhibitors of *Plasmodium*, and to screening methods for identifying such inhibitors.

BACKGROUND OF THE INVENTION

Malaria is the most important human parasitic disease. More than forty percent of the world's population live in areas where malaria is transmitted (e.g., parts of Africa, Asia, the Middle East, Central and South America, Hispaniola, and Oceania). An estimated 700,000-2.7 million persons die of malaria each year, 75% of them being African children.

Biochemical and genetic analyses have shown that proteases of *Plasmodium*, the causative agent of malaria, play a central role in the entrance of the sporozoite and the merozoite into the host hepatocyte or red blood cell (RBC), respectively. The surface proteins of both extracellular invasive forms undergo obligatory proteolytic processing executed by parasite-encoded serine proteases, which are thus directly accessible to host factors such as antibodies or drugs. Importantly, 60% of the plasmatic proteins are protease inhibitors (mainly involved in the regulation of coagulation or complement activation) suggesting that the parasitic proteases active on the outer surface of the parasite are highly specific, differ from the host proteases and are insentive to host plasmatic protease inhibitors. Altogether, the features of the parasite serine proteases involved in RBC and hepatocytes invasion make them attractive targets as novel anti-malarials.

SUB2 and SUB1 are two essential *Plasmodium* serine proteases which are known to be involved in host cells invasion. The SUB2 subtilisin-like serine protease is discharged by the parasite onto the surface of the extracellular merozoite, where it performs proteolytic processing of major parasite surface proteins, a final maturation step that is essential for host cell invasion. SUB2 sequence is highly conserved in *P. falciparum* and *P. vivax*. Because of all its interesting properties, SUB2 has been described as a novel anti-malarial drug target in International PCT patent application WO2006/120579. The SUB1 enzyme has been shown to be involved in the egress of *Plasmodium* from infected erythrocytes and plays also a yet undefined role during the RBC invasion process per se. The SUB1 enzyme of *P. falciparum* has also been the subject of a fluorescence-based assay for identifying inhibitors of *P. falciparum* (Blackman et al. (2002), Biochemistry, 41, 12244-12252). SUB2 and SUB1 share substantial inter-species structural homology in their catalytic domains (e.g. >75% sequence identity between the PfSUB2 and PvSUB2 domains, and between PfSUB1 and PvSUB1 domains). The *Plasmodium* genome harbours a third prokaryotic subtilisin-like serine protease, SUB3, which differs from SUB1 and SUB2 in being not essential for the intra-erythrocytic cycle. However, its expression is activated after the entry of the sporozoites into the hepatocytes, suggesting a role during the establishment of the infectious process in mammalian hosts.

Chloroquine is a 4-aminoquinoline drug used in the treatment or prevention of malaria. Popular drugs based on chloroquine phosphate (also called nivaquine) are Chloroquine FNA, Resochin and Dawaquin. Worryingly, resistance to both *Plasmodium falciparum* and *P. vivax*, the two main species infecting humans, have eroded treatment efficacy and malaria control measures. In addition, mosquito resistance to insecticides is spreading. Efforts at developing a malaria vaccine with long term efficiency have met with limited success.

There is thus an urgent need for the discovery, screening and development of novel anti-malarials. There is also a need for compounds targeting *Plasmodium* invasion process of either the hepatocyte or the red blood cells. There is also a need for enzyme inhibitors effective for prophylaxis preventing host infection.

BRIEF SUMMARY OF THE INVENTION

The present inventors have designed methods for screening inhibitors of *Plasmodium*, and more particularly inhibitors of *Plasmodium* subtilisin-like proteases. The inventors have also identified new inhibitors of *Plasmodium*, and more particularly inhibitors of *Plasmodium* subtilisin-like proteases.

One particular aspect of the invention relates to a screening method for identifying inhibitors of *Plasmodium* and compounds identified using such methods, including more particularly inhibitors of *Plasmodium* subtilisin-like proteases. The screening method of the invention can be a low throughput screening or a high throughput screening. Alternatively, the screening method of the invention can comprise one or several step(s) of low throughput screening and one or several step(s) of high throughput screening.

A related aspect concerns tagged peptidic substrates for use in screening assays directed in indentifying inhibitors of *Plasmodium*. The tagged peptidic substrates may be particularly useful in high-throughput screening methods and screening assays. Related aspect concerns high-throughput screening methods, including fluorescence based methods comprising the use of such tagged peptidic substrates for identifying inhibitors of *Plasmodium*, including inhibitors of *Plasmodium* subtilisin-like proteases.

The invention also relates to methods for identifying compounds capable of targeting more than one protease, presumably at different parasite stages, which is likely to maximize efficacy, and minimize the risks of failure or resistance. In other embodiments, the selected *Plasmodium* proteases belong to the same family of enzymes, thus displaying common features in their active sites, thereby providing the possibility of identifying biologically active inhibitors capable of binding multiple *Plasmodium* targets. The methods of the invention may also be useful in identifying anti-malarial candidates targeting a set of *Plasmodium* enzymes crucial for the parasite invasion into and egress from host cells processes.

The invention also relates to nucleic and amino acid sequences as shown in FIGS. 1C, 4A, 4B, 4C, 4D, 5A, 5B, 6A and 6B. In particular aspects the invention relates to the *Plasmodium vivax* Belem strain SUB1 wild-type and its amino acid sequence as defined at FIG. 1C and encoded by the polynucleotide of FIG. 4A. The invention further relates to recombinant PvSUB1, PfSUB1 and PbSUB1 purified enzymes and to the recodoned nucleic sequences of PfSUB1 and PbSUB1 as defined at FIGS. 5A and 6A, respectively.

The invention further encompasses assay kits and methods for screening of possible therapeutic anti-malaria compounds and compositions to help alleviate, treat and/or prevent *Plasmodium* infections, especially in humans.

Additional aspects, advantages and features of the present invention will become more fully understood from the detailed description given herein and from the accompanying drawings, which are exemplary and should not be interpreted as limiting the scope of the invention.

BRIEF DESCRIPTION OF THE FIGURES

FIG. 1C is a panel showing multiple sequence alignment of different strains of *Plasmodium*. The sequences of *P. falciparum* SUB1 (clone 3D7, PlasmoDB™ ID no PFE0370c: SEQ ID NO: 23), *P. berghei* SUB1 (strain ANKA, PlasmoDB™ ID no PB001288.02.0: SEQ ID NO: 20), *P. yoelii* SUB1 (strain 17XNL, PlasmoDB™ ID no PY04329: SEQ ID NO: 21) and *P. vivax* SUB1 (clone SalI, PlasmoDB™ ID no PVX_097935: SEQ ID NO: 22) have been extracted from plasmodb.org, while the *P. vivax* SUB1 (clone Belem, GenBank™ accession number FJ536584; SEQ ID NO: 2) has been PCR amplified from genomic DNA and sequenced. The alignment has been obtained using ClustalW and formatted using Boxshade, both accessible on bioweb2.pasteur.fr. Residues identical in all sequences appeared in black boxes, while similar residues are in grey boxes. The four residues (Aspartic acid, Histidine, Asparagine and Serine) constitutive of SUB1 subtilisine-like active site are indicated with a star (*) and boxed.

FIG. 2A (middle panel) depicts analysis of HPLC-fractions of purified recombinant PvSUB1 by SDS-PAGE stained with Coomassie blue.

FIG. 2A (bottom panel) is a bar graph showing enzymatic activity of HPLC-fractions of purified recombinant PvSUB1 using a FRET-specific based assay.

FIG. 3A shows inhibition of the maturation of PfSUB1's natural substrate SERA5 comprising In vitro synchronized culture of *P. falciparum* composed of 0.5% of segmented schizonts (To). FIG. 3B shows inhibition of the merozoites egress/invasion steps on *P. falciparum* in vitro culture.

FIG. 4A depicts the nucleotide sequence of *Plasmodium vivax* SUB1-Belem (PvSUB1-Belem) (SEQ ID NO: 1). Underlined 5' and 3' sequences correspond to untranslated nucleotides from the vector.

FIG. 4B depicts the full length amino acid sequence of *Plasmodium vivax* SUB1-Belem (PvSUB1-Belem) (SEQ ID NO: 2).

FIG. 4C depicts the full length amino acid sequence of recombinant *Plasmodium vivax* SUB1-Belem (PvSUB1-Belem) (SEQ ID NO: 3). Underlined sequences correspond to a signal peptide sequence and vector-related amino acids (N-terminal) and a tag composed of 6 histidines (C-terminal).

FIG. 4D the amino acid sequence of the recombinant enzymatically active form of *Plasmodium vivax* SUB1-Belem (PvSUB1-Belem), following auto-maturation at the KLV-GAD//DVSLA (SEQ ID NO: 91 site (SEQ ID NO: 4). Underlined sequence corresponds a tag composed of 6 histidines.

FIG. 5A depicts the recodoned nucleotide sequence of recombinant *Plasmodium falciparum* SUB1 (PfSUB1) nucleotide sequence (SEQ ID NO: 5). Underlined 5' and 3' sequences correspond to untranslated nucleotides from the vector.

FIG. 5B depicts the full length amino acid sequence of recombinant *Plasmodium falciparum* SUB1 (PfSUB1) (SEQ ID NO: 6). Underlined sequences correspond to a signal peptide sequence and vector-related amino acids (N-terminal) and a tag composed of 6 histidines (C-terminal).

FIG. 6A depicts the recodoned nucleotide sequence of recombinant *Plasmodium berghei* SUB1 (PbSUB1) (SEQ ID NO: 7). 5' capital letters correspond to vector sequences encoding a signal peptide and vector-related amino acids. Underlined 3' sequence correspond to untranslated nucleotides from the vector.

FIG. 6B depicts the full length amino acid sequence of recombinant *Plasmodium berghei* SUB1 (PbSUB1) (SEQ ID NO: 8). Underlined sequences correspond to a signal peptide sequence and vector-related amino acids (N-terminal) and a tag composed of 6 histidines (C-terminal).

DETAILED DESCRIPTION OF PREFERRED EMBODIMENTS

I. Screening Methods

Figure 1A:
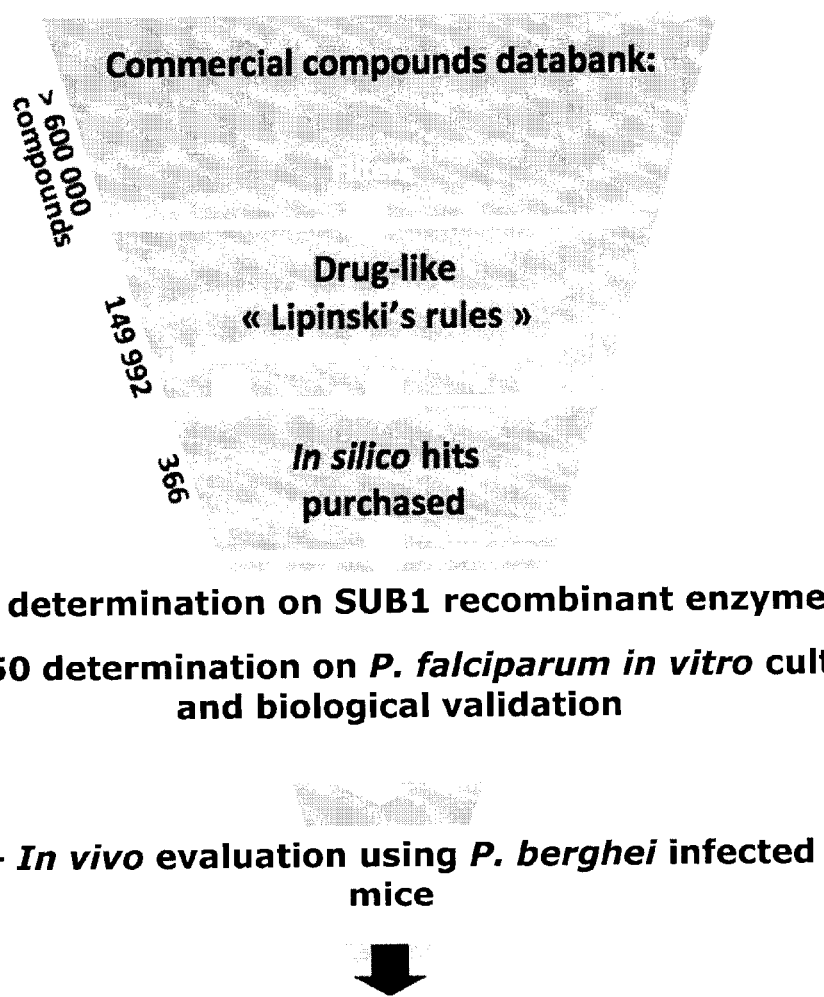
FIG. 1A is a schematic representation of a screening method for *Plasmodium* inhibitors according to an embodiment of the invention.

One aspect of the invention concerns screening methods for identifying inhibitors of *Plasmodium*, and more particularly inhibitors of *Plasmodium* subtilisin-like proteases. In the context of the present invention, "inhibitors of *Plasmodium*" or "anti-malaria compounds" refer to compounds that are able to help alleviate, treat and/or prevent *Plasmodium* infections, especially in humans. Suitable inhibitors according to the invention include those compounds capable of inhibiting *Plasmodium* life-cycle, including but not limited to inhibition of *Plasmodium* growth, multiplication, development, liberation from host-infected cells and invasion into host cells. In some embodiments, these compounds are able to inhibit the parasite invasion into and egress from red blood cells. In some embodiments, the compounds are inhibitors of *Plasmodium* subtilisin-like proteases, able to inhibit the enzymatic activity of a *Plasmodium* subtilisin-like serine protease. Preferably, the compounds are inhibitors of orthologous subtilisin-like serine protease (i.e. "same" or "corresponding" protease from different *Plasmodium* species). In other preferred embodiments, the compounds are inhibitors of different types subtilisin-like serine protease (e.g. SUB1, SUB2 and SUB3).

In Vitro Screening of *Plasmodium* Inhibitors

According to additional particular aspects, the invention relates to in vitro screening methods and tagged peptidic substrates for identifying inhibitors of *Plasmodium*. These in vitro screening methods and substrates are based on the importance of normal biological activity of subtilisin-like proteases for the life-cycle of various species of *Plasmodium* such as *Plasmodium vivax, Plasmodium falciparum, Plasmodium berghei* and other *Plasmodium* species. Potentially pharmaceutically useful inhibitors of *Plasmodium* can thus be identified by measuring the effect of candidate compounds on one or more subtilisin-like proteases. Accordingly, the present inventors have developed tagged peptidic substrates and related methods for measuring subtilisin-like proteases activity.

In one embodiment, the in vitro screening method for identifying inhibitors of *Plasmodium*, comprises assessing cleavage of a peptidic substrate in presence of a candidate compound, wherein the peptidic substrate is cleavable by a protease comprising SEQ ID NO: 4. A particular example of a protease comprising SEQ ID NO: 4 is the active form of PvSUB1-Belem which amino acid sequence is illustrated in FIG. 4D. Additional examples of proteases comprising SEQ ID NO: 4 include the full-length inactive precursor of PvSUB1-Belem of FIGS. 4B and 4C. In preferred embodiments, assessing cleavage of the peptidic substrate consists of detecting the cleavage of the peptidic substrate by the malarial protease PvSUB1-Belem which amino acid sequence is illustrated in FIG. 4D. For performing an enzymatic assay, the protease may be produced and purified under a soluble active recombinant protein, or it may be purified from parasite-RBC culture by HPLC fractionation.

In a preferred embodiment, the tagged peptidic substrate comprises two aspartic acids and the protease cleaves the peptidic substrate between these two aspartic acids. Preferably the tagged peptidic substrate comprises the amino acid sequence K-L-V-G-A-D-D-V-S-L-A (SEQ ID NO: 9). In another embodiment, the tagged peptidic substrate comprises the amino acid sequence K-L-V-G-A-D-D-V-S-L-A-K (SEQ ID NO: 10).

As it will be exemplified hereinafter, the peptidic substrate is preferably tagged with a quencher and/or a fluorophore, most preferably both, for easily measuring cleavage of the peptide in high-throughput fluorescence assays such as FRET. Examples of suitable quenchers include, but are not limited to, Dabsyl and DYQ60. Examples of suitable fluorophores include, but are not limited to, EDANS or DY630. Because they allow screening a large diversity of chemical compounds in an enzymatic assay in a robust and reproducible way, the following combinations of quencher and fluorophore are preferred: i) Dabsyl and EDANS; and ii) in a most preferred way DYQ660 and DY630, which work with excitation and emission wavelengths in the far red spectrum, thus reducing the risks of auto-fluorescence of the chemical compounds. In preferred embodiments, the tagged peptidic substrate consists of Dabsyl-K-L-V-G-A-D-D-V-S-L-A-EDANS (Dabsyl-SEQ ID NO: 9-EDANS) or DYQ660-K-L-V-G-A-D-D-V-S-L-A-K-DY630 (DYQ660-SEQ ID NO: 10-DY630). It is within the skill of those in the art to select suitable quenchers and fluorophores and other possibilities include for instance Dabcyl and EDANS, 5-IATR, 6-IATR.

In particular embodiments, the in vitro screening method comprises assessing cleavage of the peptidic substrate in presence and in absence of a candidate compound. Accordingly a candidate compound is considered an inhibitor of *Plasmodium* if the cleavage of the peptidic substrate is reduced when compared to testing under similar conditions, in the absence of the candidate compound.

Inhibitory activity of the candidate compound may also be quantified. For instance, the in vitro testing may comprise: (i) measuring an inhibition constant (Ki) for the one or more *Plasmodium* subtilisin-like protease in presence of the candidate compound and/or (ii) measuring a half maximal inhibitory concentration (IC50) of the candidate compound on the one or more *Plasmodium* subtilisin-like protease. In particular embodiments, compounds having a Ki lower than about 50 µM, lower than 25 µM, lower than 10 µm, or lower than 5 µM may be considered interesting candidates and selected for further testing and development.

Preferably, the in vitro screening method of the invention is a high-throughput method. Suitable methods include fluorescence-based methods such as Fluorescent Resonance Energy Transfer (FRET). Those skilled in the art are capable of indentifying additional high-throughput methods, techniques and assays which can be adapted for screening and/or identifying inhibitors of *Plasmodium*, and/or for assessing cleavage of a peptidic substrate according the methods of the invention.

The in vitro screening method of the invention may comprise additional steps for selecting, validating or chemically optimizing potentially useful candidate compounds. Potentially active inhibitors may thus be tested in any suitable in silico, in vitro, ex vivo and/or in vivo assays. In a particular embodiment the in vitro screening method further comprises selecting a candidate compound capable of inhibiting cleavage of the peptidic substrate; and testing the selected compound ex vivo on a culture of one or more species of *Plasmodium* and/or testing said selected compound in vivo in at least one *Plasmodium*-infected animal. Although it is generally preferable to proceed incrementally from in silico, in vitro, ex vivo to in vivo testing, the invention is not limited to a particular order.

In Silico Screening of *Plasmodium* Inhibitors

The invention further relates to computational related methods for screening and/or identifying inhibitors of *Plasmodium* in silico.

According to a particular aspect, the invention relates to a screening method for identifying inhibitors of *Plasmodium*, comprising:
 (a) in silico docking a 3D structure of a plurality of candidate compounds to a 3D computerized model of one or more *Plasmodium* subtilisin-like protease; and
 next carrying out at least one of the steps of:
 (b) testing in vitro candidate compound(s) from step (a) having a desired in silico docking activity for assessing in vitro inhibition of one or more *Plasmodium* subtilisin-like protease;
 (c) testing ex vivo candidate compound(s) from step (a) having a desired in silico docking activity for assessing inhibition of one or more species of *Plasmodium* in culture;
 (d) testing in vivo candidate compound(s) from step (a) having a desired in silico docking activity for assessing inhibition of one or more species of *Plasmodium* in a *Plasmodium*-infected animal.

In one particular embodiment, the screening method comprises:
 (a) in silico docking a 3D structure of a plurality of candidate compounds to a 3D computerized model of one or more *Plasmodium* subtilisin-like protease,
 (b) testing in vitro inhibitory activity of the candidate compound(s) from step (a) having a desired in silico docking activity on one or more *Plasmodium* subtilisin-like protease enzymatic activity,
 (c) optionally testing ex vivo inhibitory activity of the candidate compound(s) from step (b) on a culture of one or more *Plasmodium* species,
 (c) optionally testing in vivo the candidate compound(s) from step (b) or (c) having a desired in vitro and/or ex vivo activity on at least one *Plasmodium*-infected animal model,
 wherein the identified inhibitors of *Plasmodium* are able to inhibit several *Plasmodium* species.

According to another aspect, the invention relates to a screening method for identifying inhibitors of multiple *Plasmodium* species. In one embodiment the method comprises:
 (a) in silico docking a 3D structure of a plurality of candidate compounds to a 3D computerized model of one or more *Plasmodium* subtilisin-like protease; and (b) testing in vitro, ex vivo, and/or in vivo candidate compounds from step (a) having a desired in silico docking activity;

wherein step (b) is carried out for identifying inhibitors active against at least one subtilisin-like protease that is different from and that is an ortholog of the subtilisin-like protease of step (a).

In a further aspect, the invention relates to a method for identifying inhibitors of multiple *Plasmodium* species, comprising testing with at least two different techniques for candidate compounds having a desired *Plasmodium* protease inhibitory or binding activity;

wherein the at least two different techniques are selected from the group consisting of in silico docking, in vitro inhibitory activity, ex vivo inhibitory activity, and in vivo inhibitory activity; and wherein the at least two different techniques involve testing inhibitory activity of the candidate compounds against *Plasmodium* subtilisin-like proteases from at least two different *Plasmodium* species (e.g. orthologs) and/or against at least two distinct subtilisin-like protease from a same *Plasmodium* species.

The screening methods above comprise a step that is carried out in silico. In silico screening of drugs and in silico-based drug design is becoming more and more popular (e.g. Song et al., 2005, PNAS, 102:4700-05; Plewczynski et al., 2007, Chem Biol Drug Des, 69:269-279; Leitao et al., 2008, Eur J Med Chem, 43:1412-1422; Kirchmair et al, 2008, Curr Med Chem 15:2040-53; Zoete et al., 2009, J Cell Mol Med, 13:238-78; Jain A N 2004, Curr Opin Drug Discov Devel, 7:396-403; Rester U 2008, Curr Opin Drug Discov. Devel 11:559-68). The present invention uses general principles of in silico screening known and applied by those skilled in the art in the discovery or screening of enzymes inhibitors, including protease inhibitors. Without being bound by any particular details or explanation, a first element which is typically required is a virtual 3D-structure of the targeted protein. Such structure may be obtained from the 3D X-ray crystallography resolution, or from a model deriving from the 3D X-ray crystallography resolved structure of one or more closely related proteins. The second required element is a precise spatial identification of the catalytic site of interest (e.g. hydrophobic pocket). Such precise spatial identification generally comprises 3D coordinates of (i) the catalytic site where the substrate will dock and (ii) of the proximal amino acids which participates in the docking because of physico-chemical forces (e.g. hydrophobic interactions, hydrogen bonding, van der Waals forces, etc.). Finally, the third required element is the 3D structure of the chemical compounds to be tested (e.g. a library of chemical compounds). 3D structure of a chemical compound may be a X-ray crystallography resolved structure or a 3D structure which has been modeled using the 2D chemical structure or the chemical formula of the compound. Having these three elements in silico screening typically takes place by using computational chemistry software, the software calculating, for each chemical compound to be tested, probabilities for the compound to interact or bond into the catalytic site of the targeted protein. Compounds with the best score are selected for subsequent in vitro, ex vivo, and/or in vivo rounds of screening. Suitable computational chemistry software include, but are not limited to, Flex™, FlexX-Pharm™, and Icm™.

The *Plasmodium* protease may be selected from the subtilisin-like protease 1 "SUB1", the subtilisin-like protease 2 "SUB2", and the subtilisin-like protease 3 "SUB3". One may take advantage of the similarity of *Plasmodium* subtilisins active site and use, as the 3D model, a homology model of two different *Plasmodium* proteases (e.g. SUB1 and SUB2). Similarly, one may take advantage of the similarity of SUB1 active site with bacterial subtilisins and use, as the 3D model, a homology model based on known bacterial and/or fungi subtilisins 3D structures. Examples of known and accessible 3D structures include, but are not limited to, those published in the RCSB Protein Data Bank™ that are directly accessible on the web site pdb.org or via the NCBI web site. Particular examples include the following proteins: BPN' (Acc. No. 1LW6); sphericase (Acc. No. 1EA7); Thermitase (Acc. No. 2TEC); AK-1 Serine protease (Acc. No. 1 DBI); subtilisin Carlsberg (Acc. No. 1ROR); proteinase K (Acc. No. 1106) and *Bacillus lentus* subtilisin (Acc. No. 1GCI).

In a preferred embodiment, the 3D computerized model of one or more *Plasmodium* protease used according to the methods of the invention is a single homology model realized using at least two distinct *Plasmodium* subtilisin-like proteases (e.g. orthologs from *Plasmodium vivax, Plasmodium falciparum* and *Plasmodium berghei*).

In various embodiments, the methods of the invention permits to test candidate compounds against one or more *Plasmodium* subtilisin-like protease. Accordingly, the one or more *Plasmodium* subtilisin-like protease may be orthologous subtilisin-like proteases from different *Plasmodium* species (e.g. SUB1 from *P. vivax* then against SUB1 from *P. falciparum* and/or SUB1 from *P. berghei*). According to some embodiments, the in silico, in vitro, ex vivo and in vivo testing may be carried out on different strains of *Plasmodium*. In one particular embodiment the in silico docking step involves a 3D-model of a protease from *Plasmodium vivax* whereas in vitro and ex vivo testings involve a protease from *Plasmodium vivax* and/or *Plasmodium falciparum*, and in vivo testing involves an animal model for *Plasmodium berghei* infection. The one or more *Plasmodium* subtilisin-like protease may also consist of different enzymes, but from the same *Plasmodium* species (e.g. SUB1, SUB2 and/or SUB3 from *P. vivax*). Additional permutations are also possible (e.g. testing against (Pv)SUB1 and (Pf)SUB2).

Accordingly, in step (b) assessing in vitro inhibition of one or more *Plasmodium* subtilisin-like protease may comprise: (i) assessing in vitro inhibition of a subtilisin-like protease which is orthologous protease from a different species of *Plasmodium* than the *Plasmodium* subtilisin-like protease of step (a); and/or (ii) assessing in vitro inhibition of a subtilisin-like protease which is from a same *Plasmodium* species but a distinct protease than the *Plasmodium* subtilisin-like protease of step (a). Similarly, step (b) itself may comprises multiple testing of candidate compounds against one or more *Plasmodium* subtilisin-like protease and may comprise: (i) assessing in vitro inhibition of orthologous subtilisin-like proteases from at least two different species of *Plasmodium*; and/or (ii) assessing in vitro inhibition of distinct subtilisin-like proteases from a same *Plasmodium* species. Various testing experiments may also be performed in parallel (e.g. testing against (Pv)SUB1 and (Pf)SUB2). The in vitro testing step can consist in one or more of in vitro assays as described above. Other routinely in vitro assays can also be performed.

A further aspect, the invention relates to a method for identifying inhibitors of *Plasmodium falciparum*, comprising: (i) a first screening step directed in identifying potential inhibitors of *Plasmodium vivax*, and (ii) testing subsequently in vitro, ex vivo and/or in vivo potential inhibitors from step (i) for inhibition against *Plasmodium vivax, Plasmodium falciparum* and/or *Plasmodium berghei*. The first screening step comprises a step that is carried out in silico, more preferably by in silico docking a 3D structure of potential inhibitors into a 3D model of a *Plasmodium vivax* protease.

In preferred embodiments the *Plasmodium vivax* protease is a recombinant SUB1 protease, for instance a recombinant SUB1 protease comprising the amino acid sequence of PvSUB1-Bellem as defined at FIG. 1C.

In a particular embodiment of the screening methods described hereinbefore, candidate compounds are tested in silico (step (a)) using a 3D computerized model of SUB1 from *P. vivax*; next candidate compounds are tested in vitro (at step (b)) using SUB1 from *P. vivax*; next candidate compounds are tested ex vivo (step (c)) against *P. falciparum*; and then candidate compounds are tested in vivo (step (d)) against *P. berghei*.

In an another embodiment of the screening method described hereinbefore, candidate compounds are tested in silico (step (a)) using a 3D computerized model of SUB1 from *P. falciparum*; next candidate compounds are tested in vitro (at step (b)) using SUB1 from *P. falciparum*; next candidate compounds are tested ex vivo (step (c)) against *P. falciparum*; and then candidate compounds are tested in vivo (step (d)) against *P. berghei*.

The in vitro testing step can be performed using different types of assays, for instance by measuring the enzymatic activity of a *Plasmodium* subtilisin-like protease in presence of a compound to be tested. In a preferred embodiment, the assay is an enzymatic assay as described hereinbefore based on the cleavage of FRET (Fluorescent Resonance Energy Transfer) SUB-specific substrates. Suitable examples of substrates for SUB1 enzymes include, but are not limited to, those shown in Table 3. For performing an enzymatic assay, the *Plasmodium* protease may be produced and purified under a soluble active recombinant protein, or it may be purified from parasite-RBC culture by HPLC fractionation.

Inhibitory activity of the candidate compound may also be quantified. For instance, the in vitro testing may comprise: (i) measuring an inhibition constant (Ki) for the one or more *Plasmodium* subtilisin-like protease in presence of the candidate compound and/or (ii) measuring a half maximal inhibitory concentration (IC50) of the candidate compound on the one or more *Plasmodium* subtilisin-like protease. For instance, compounds having a Ki lower than about 50 µM, lower than 25 µM, lower than 10 µm or lower than 5 µM may be considered as interesting candidates for further testing and development.

The inhibition of the enzymatic activity of a *Plasmodium* subtilisin-like protease by a test compound could also be validated by quantification of the processed parasite target proteins using specific antibodies. Some of the natural substrates of SUB2 and SUB1 are known: AMA1 and MSP1-42 for SUB2, and SERA for SUB1. The effect of SUB1 inhibitors on SERA maturation can be evaluated for example, and is further illustrated in Examples.

Similarly, assessment of ex vivo efficacy of a test compound can be evaluated by measuring the $EC_{50}$ (or $IC_{50}$) constant for the test compound. Typically, the parasite culture is a *Plasmodium falciparum* or a *Plasmodium vivax* culture. Ex vivo cultivated *Plasmodium* can be chosen among references clones or among *Plasmodium* field isolates. A representative panel of *P. falciparum* and *P. vivax* parasites can be used for this type of assay.

The ex vivo testing step can consist in assessing the effect of a test compound on a *Plasmodium* stage-specific ex vivo culture. The ex vivo culture is for example composed of segmented schizonts of *P. falciparum* at 0.5% parasitemia and 1% hematocrit. The progress of the parasitemia from segmented schizonts to newly formed trophozoits, and the effect of test compound on this process, may be assessed by flow cytometry analysis.

The in vivo testing step can consist in measuring the effect of a test compound on red blood cell infection in *Plasmodium*-infected animals. The preferred parasited animal model is *Plasmodium berghei*-infected mice.

Kits

A further aspect of the invention relates to kits. The kits of the invention may be useful for the practice of the methods of the invention, particularly for in vitro screening of *Plasmodium* inhibitors.

A kit of the invention may comprise a tagged peptidic substrate as described herein and a protease, particularly a *Plasmodium* subtilisin-like protease. Preferably the protease comprises SEQ ID NO:4, and more preferably the protease is a recombinant protease. The kit may also comprise one or more additional components, such as incubation and assay buffer(s), controls, additional substrate(s), standards, detection materials (e.g. antibodies, fluorescein-labelled derivatives, luminogenic substrates, detection solutions, scintillation counting fluid, etc.), laboratory supplies (e.g. desalting column, reaction tubes or microplates (e.g. 96- or 384-well plates), a user manual or instructions, etc. Preferably, the kit and methods of the invention are configured such as to permit a quantitative detection or measurement of the protease activity.

Polynucleotides, Polypeptides and Cells

An addition aspect of the invention concerns nucleic and amino acid sequences as shown in FIGS. 1C, 4A, 4B, 4C, 4D, 5A, 5B, 6A and 6B. In particular aspects, the invention relates to the *Plasmodium vivax* Belem strain SUB1 wild-type and its amino acid sequence as defined at FIG. 1C and FIG. 4B (SEQ ID NO: 2) and encoded by the polynucleotide of sequence as set forth in FIG. 4A (SEQ ID NO:1). The invention also encompasses recombinant forms of SUB1 Belem, including the amino acid sequence as defined at FIG. 4C (SEQ ID NO: 3) and the enzymatically active form defined at FIG. 4D (SEQ ID NO: 4). The invention further encompasses to recombinant PvSUB1, PfSUB1 and PbSUB1 purified enzymes and to the recodoned nucleic sequences of PfSUB1 and PbSUB1 as defined at FIG. 5A (SEQ ID NO: 5); FIG. 5B (SEQ ID NO: 6); FIG. 6A (SEQ ID NO: 7), and FIG. 6B (SEQ ID NO: 8).

The invention further encompasses cells comprising a isolated polynucleotide as set forth in SEQ ID NO:1, SEQ ID NO:5 and/or SEQ ID NO:7, and cells comprising and/or expressing a polypeptide comprising SEQ ID NO:2, SEQ ID NO:3, SEQ ID NO:4, SEQ ID NO:6 and/or SEQ ID NO:8. Examples of cells encompassed by the invention include eukaryotic cells and more particularly cells suitable for baculovirus/insect cells expression system including, but not limited to, such as _sf9 and Hi5 cells.

II. Therapeutics

As exemplified hereinafter the methods of the invention successfully resulted in the identification of compounds having anti-malarial activity, in vitro, ex vivo and in vivo. In the context of the present invention, anti-malaria compounds, *Plasmodium*-inhibiting compounds, inhibitors of *Plasmodium* and anti-malaria candidates are equivalent terms (have the same meaning).

Accordingly, another aspect of the invention concerns anti-malaria compounds, and more particularly compounds inhibiting a *Plasmodium* protease. These compounds may be advantageously identified by the screening method of the invention. Preferably the *Plasmodium* protease is a subtilisin-like protease. In various embodiments the subtilisin-like protease is SUB1, SUB2 or SUB3.

The invention is also directed to methods for preventing, treating, improving, and/or alleviating a *Plasmodium* infection in a subject. The method comprises administering to the subject a therapeutically effective amount of a compound or of a pharmaceutical composition as defined herein. In some embodiments, a compound of the invention prevents, reduces and/or inhibits the *Plasmodium* parasite egress from and/or invasion into host cells. A related aspect concerns pharmaceutical compositions comprising a compound as defined herein. In preferred embodiments, the pharmaceutical composition is formulated as an anti-malarial drug (e.g. prophylaxis and/or treatment of malarial infections, including *Plasmodium vivax* and/or by *Plasmodium falciparum* infections). According to some embodiments, the compound of the invention is selected from the compounds in Table 1A. According to some embodiments, the compound of the invention is selected from the compounds in Table 1B:

TABLE 1A
| Compound # | Structure | MW (Daltons) |
|---|---|---|
| A/G1 | 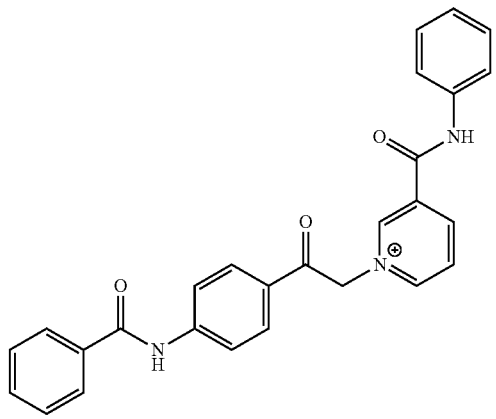 [SMILES: O=C(C[n+]1cccc(C(=O)Nc2ccccc2)c1)c1ccc(NC(=O)c2ccccc2)cc1] | 432 |
| A/G6 | 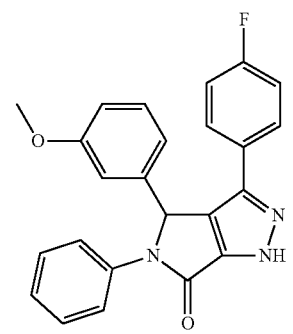 [SMILES: COc1cccc(C2c3c(-c4ccc(F)cc4)n[nH]c3C(=O)N2c2ccccc2)c1] | 399 |
| B/H5 | 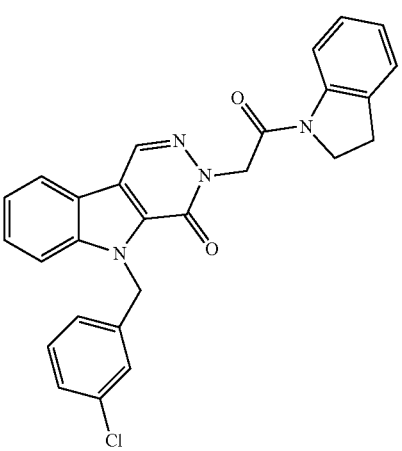 [SMILES: O=C(Cn1ncc2c3ccccc3n(Cc3cccc(Cl)c3)c2c1=O)N1CCc2ccccc21] | 468 |

TABLE 1B

| No. | Chemical Structure |
|---|---|
| I | 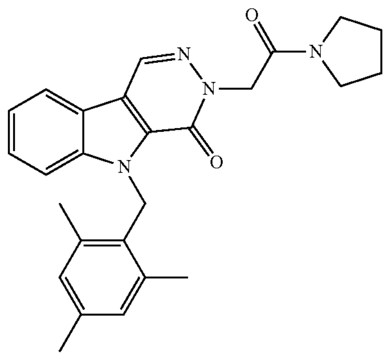 [SMILES: Cc1cc(C)c(Cn2c3ccccc3c3cnn(CC(=O)N4CCCC4)c(=O)c32)c(C)c1] |
| II | 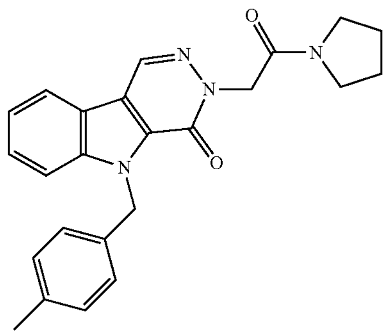 [SMILES: Cc1ccc(Cn2c3ccccc3c3cnn(CC(=O)N4CCCC4)c(=O)c32)cc1] |
| III | 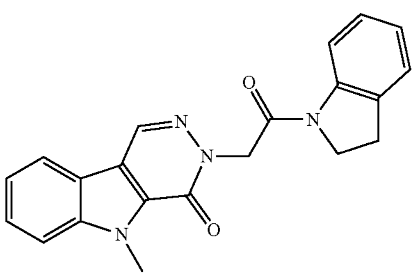 [SMILES: Cn1c2ccccc2c2cnn(CC(=O)N3CCc4ccccc43)c(=O)c21] |
| IV | 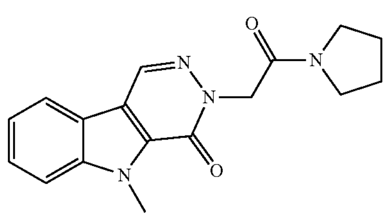 [SMILES: Cn1c2ccccc2c2cnn(CC(=O)N3CCCC3)c(=O)c21] |
| V | 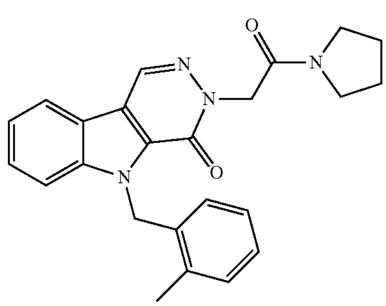 [SMILES: Cc1ccccc1Cn1c2ccccc2c2cnn(CC(=O)N3CCCC3)c(=O)c21] |
| VI | |
| VII | |
| VIII | |
| IX | |
| X | |

TABLE 1B-continued

| No. | Chemical Structure |
|---|---|
| AG6 | 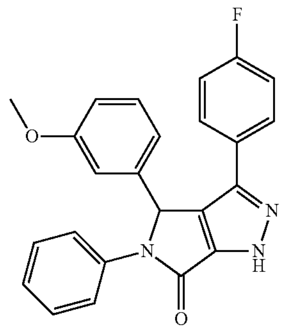 [SMILES: COc1cccc(C2c3c(-c4ccc(F)cc4)n[nH]c3C(=O)N2c2ccccc2)c1] |
| AG6-15 | 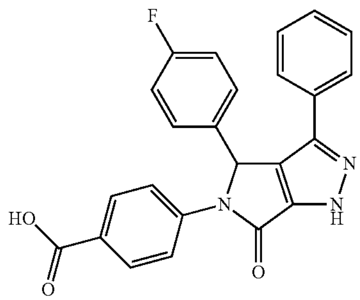 [SMILES: O=C(O)c1ccc(N2C(=O)c3[nH]nc(-c4ccccc4)c3C2c2ccc(F)cc2)cc1] |
| AG6-1 | 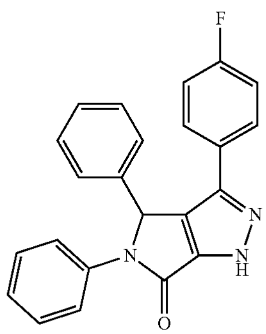 [SMILES: O=C1c2[nH]nc(-c3ccc(F)cc3)c2C(c2ccccc2)N1c1ccccc1] |
| AG6-5 | 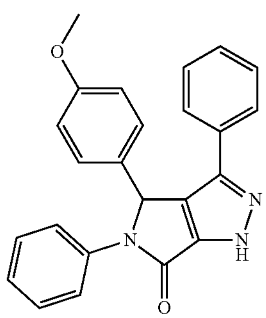 [SMILES: COc1ccc(C2c3c(-c4ccccc4)n[nH]c3C(=O)N2c2ccccc2)cc1] |
| AG6-3 | 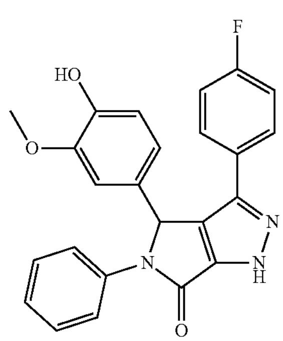 [SMILES: COc1cc(C2c3c(-c4ccc(F)cc4)n[nH]c3C(=O)N2c2ccccc2)ccc1O] |
| AG6-6 | 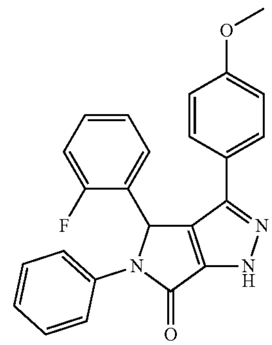 [SMILES: COc1ccc(-c2n[nH]c3c2C(c2ccccc2F)N(c2ccccc2)C3=O)cc1] |
| AG6-7 | 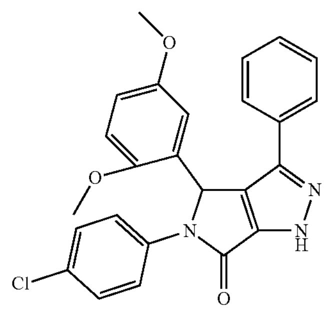 [SMILES: COc1ccc(OC)c(C2c3c(-c4ccccc4)n[nH]c3C(=O)N2c2ccc(Cl)cc2)c1] |
| AG6-2 | 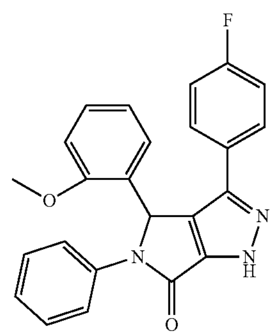 [SMILES: COc1ccccc1C1c2c(-c3ccc(F)cc3)n[nH]c2C(=O)N1c1ccccc1] |
| AG6-4 | 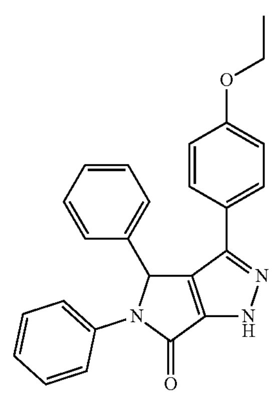 [SMILES: CCOc1ccc(-c2n[nH]c3c2C(c2ccccc2)N(c2ccccc2)C3=O)cc1] |

TABLE 1B-continued

| No. | Chemical Structure |
|---|---|
| AG6-14 | 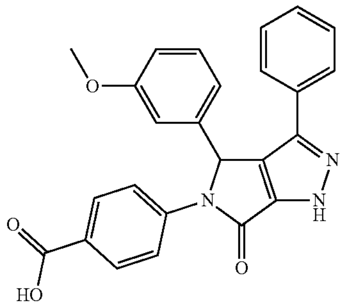 [SMILES: COc1cccc(C2c3c(-c4ccccc4)n[nH]c3C(=O)N2c2ccc(C(=O)O)cc2)c1] |
| AG6-11 | 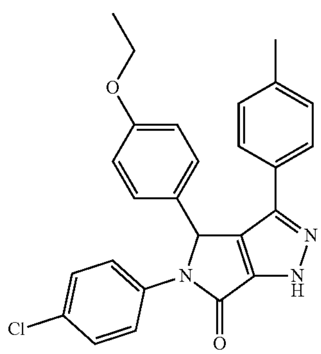 [SMILES: CCOc1ccc(C2c3c(-c4ccc(C)cc4)n[nH]c3C(=O)N2c2ccc(Cl)cc2)cc1] |
| AG6-8 | 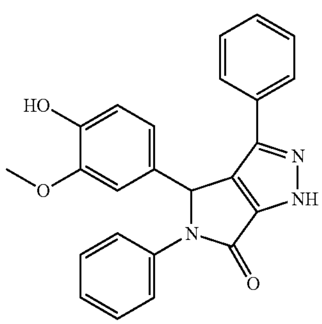 [SMILES: COc1cc(C2c3c(-c4ccccc4)n[nH]c3C(=O)N2c2ccccc2)ccc1O] |
| AG6-12 | 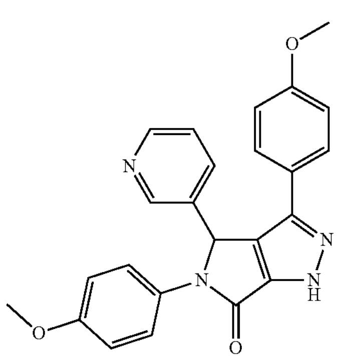 |
| AG6-9 | |
| AG6-13 | |
| AG6-10 | |
| AG6-16 | |

The invention encompasses pharmaceutically acceptable salt of the compounds of the invention, including acid addition salts, and base addition salts. As used herein, the term "pharmaceutically acceptable salt" is intended to mean those salts which retain the biological effectiveness and properties of the free acids or bases, which are not biologically or otherwise undesirable. Desirable are salts of a compound are those salts that retain or improve the biological effectiveness and properties of the free acids and bases of the parent compound as defined herein or that takes advantage of an intrinsically basic, acidic or charged functionality on the molecule and that is not biologically or otherwise undesirable. Examples of pharmaceutically acceptable salts are also described, for instance, in Berge et al., "Pharmaceutical Salts", J. Pharm. Sci. 66, 1-19 (1977).

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)— or (S)— or, as (D)- or (L)- for amino acids. The present invention is intended to include all such possible isomers, as well as, their racemic and optically pure forms. Certain compounds of the present invention may exist in Zwitterionic form and the present invention includes Zwitterionic forms of these compounds and mixtures thereof.

In general, all compounds of the present invention may be prepared by any conventional methods, using readily available and/or conventionally preparable starting materials, reagents and conventional synthesis procedures.

The invention also encompasses the uses of a compound of the invention as defined herein, in combination with one or more existing anti-malarial drug (see hereinafter).

According to some embodiments, the compounds and compositions of the invention are capable of targeting more than one enzyme, presumably at different parasite stages, thereby maximizing efficacy, and/or minimizing risks of failure or resistance. Preferably, the compounds inhibit the activity of at least one subtilisin-like protease, more preferably, SUB1, SUB2 and/or SUB3.

According to some embodiments, the compounds and compositions of the invention are capable of inhibiting *Plasmodium* resistant strains, including but not limited to strains resistant to chloroquin, strains resistant to artemisinin, and/or strains resistant to derivatives of such anti-malarial drugs.

In preferred embodiments the compounds of the invention have Ki less than about 50 µM on recombinant subtilisin-like protease, and in more preferred embodiments less than 10 µM. In other preferred embodiments the compounds of the invention have an IC50 of about 20 µM or less, of about 1 µM or less, or about 100 nM or less. In some embodiments the compounds of the invention have an in vivo LD50 (in humans or animals) of about 33 mg/kg or less (e.g. ≤30 mg/kg, ≤10 mg/kg, or ≤1 mg/kg).

In a related aspect, the invention concerns a method for preventing, treating, improving, and/or alleviating a *Plasmodium* infection in a subject, the method comprising administering to the subject a therapeutically effective amount of a compound or of a pharmaceutical composition as defined herein.

The term "subject" includes living organisms in which a *Plasmodium* infection can occur. The term "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as wild and domestic bird species (e.g. chickens), and transgenic species thereof. Preferably, the subject is a mammal. More preferably, the subject is a human.

The pharmaceutical compositions of the invention may comprise a therapeutic agent (e.g. a compound listed in Table 1A or 1B or a compound identified by the above screening method) in a pharmaceutically acceptable excipient, carrier, buffer, stabilizer or other materials well known to those skilled in the art. Such materials should be non-toxic and should not interfere with the efficacy of the active ingredient.

The precise nature of the carrier or other material may depend on the route of administration, e.g. oral, intravenous, cutaneous or subcutaneous, nasal, intramuscular, and intraperitoneal routes.

The pharmaceutical compositions of the invention may comprise a compound of the invention as defined herein, in combination with one or more existing anti-malarial drug, including but not limited to chloroquine FNA, resochin, dawaquin, artemisinin, quinine, amodiaquine, sulfadoxynie, pyrimethamine, mefloquine, proguanil, artesunate, halofantrine, and atovaquone.

With respect to pharmaceutically useful compounds or compositions according to the present invention that is to be given to an individual, administration is preferably in a "prophylactically effective amount" or a "therapeutically effective amount" (as the case may be, although prophylaxis may be considered therapy), this being sufficient to show benefits to the individual.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The invention is further illustrated by the following examples, which should not be construed as further limiting.

EXAMPLES

Example 1

An in Silico Screening Approach to Select Inhibitors of *Plasmodium*

Red blood cell egress and invasion by *Plasmodium* parasites strictly depend upon the precise maturations of parasite proteins SERA5, a cystein protease implicated in the rupture of the parasitophorous vacuole membrane and MSP1 (Merozoite Surface Protein 1). The parasite subtilisin-like serine protease SUB1 plays a key role in the process (S. Yeoh et al, *Cell*, 131(6), 1072-83 (2007)) as it is essential for the merozoite egress. On the other hand, SUB2, another subtilisin-like serine protease is essential for the merozoite entry into RBC. Taking advantage of the similarity of SUB1 active site with bacterial subtilisins, we have used an in silico screening approach and have identified inhibitors of *Plasmodium*.

A general strategy for screening and validation of *Plasmodium* inhibitors according to a preferred embodiment of the invention is summarized in FIG. 1A. Briefly, commonly used filters were applied in silico to a commercial chemical library comprising more than 600 000 compounds to identify compounds having a drug like structures (e.g. Lipinski's rules). The resulting compounds (149 992) were then screened by using an in silico approach by performing virtual screening on 3D-models of PvSUB1 active site structure using FlexX™, FlexX-Pharm™ or Icm™. As described hereinafter, in silico hits (366), compounds harbouring the best scores from the different in silico screening, were purchased and tested in the laboratory for Ki determination on PvSUB1 enzymatic activity, IC50 determination on *P. falciparum* in vitro culture, and in vivo evaluation.

The in silico step was based on in silico docking of test compounds into SUB1 modeled active sites, and more particularly a 3D model of a recombinant SUB1 protein (PvSUB1) derived from *Plasmodium vivax* sequences.

Figure 1B:
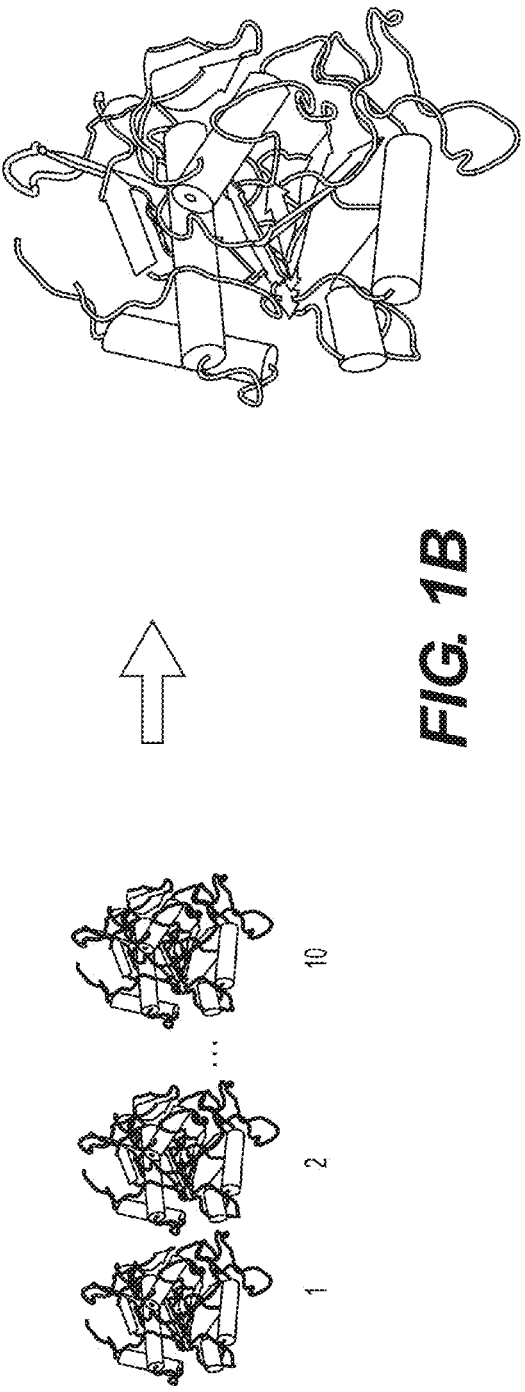
FIG. 1B is a panel showing the selection and optimization of a PvSUB1 optimized model according to an embodiment the invention (SEQ ID NOS: 12 to 191.

The selection and optimization of the PvSUB1 optimized model is illustrated in FIG. 1B. That figure (top) shows that the final 3D structure was obtained from conserved amino acid sequences surrounding D15, H58, N153, S221 which are involved in the calalytic cleavage site of PvSUB1. The bottom FIG. 1B shows a representative example of the iterative computerized process for obtaining a 3D model of the catalytic site of PvSUB1. The 3D structures of test compounds was also inputted and tested for docking into the active site by using different computer software (e.g. Flex™, FlexX-Pharm™, Icm™). Those with the best score were selected for the subsequent screening steps.

It is the amino acid sequence of PvSUB1 of *Plasmodium vivax* Bellem isolate which was used for creating the PvSUB1 optimized model described hereinabove (see FIG. 1C and its legend). The Table 2 hereinafter displays percentages of similarity and identity between the full length and enzymatic forms of all the SUB1 orthologues.

Figure 2A:
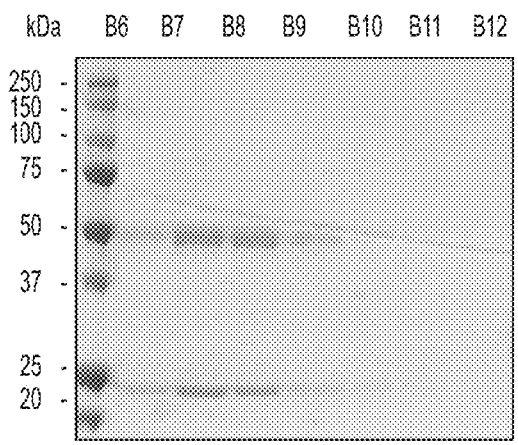
FIG. 2A (top panel) is a schematic representation of PvSUB1 precursor and auto-maturated active form. DHNS (SEQ ID NO: 24). DVSLA (SEQ ID NO. 25).
Figure 2A:
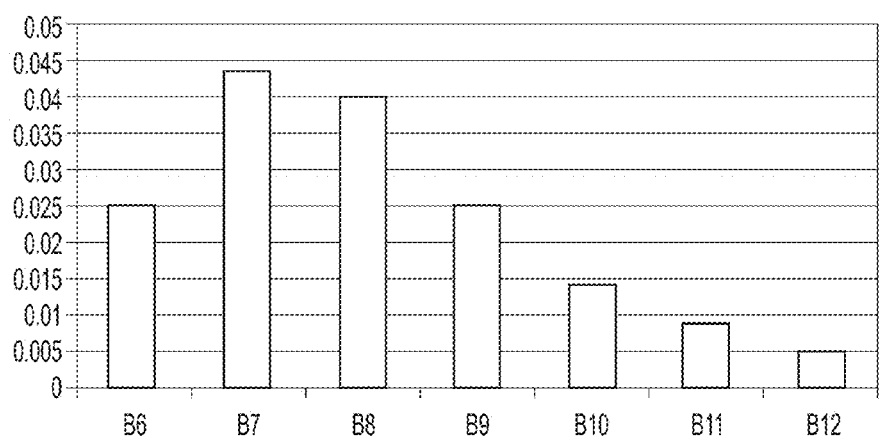
Figure 2B:
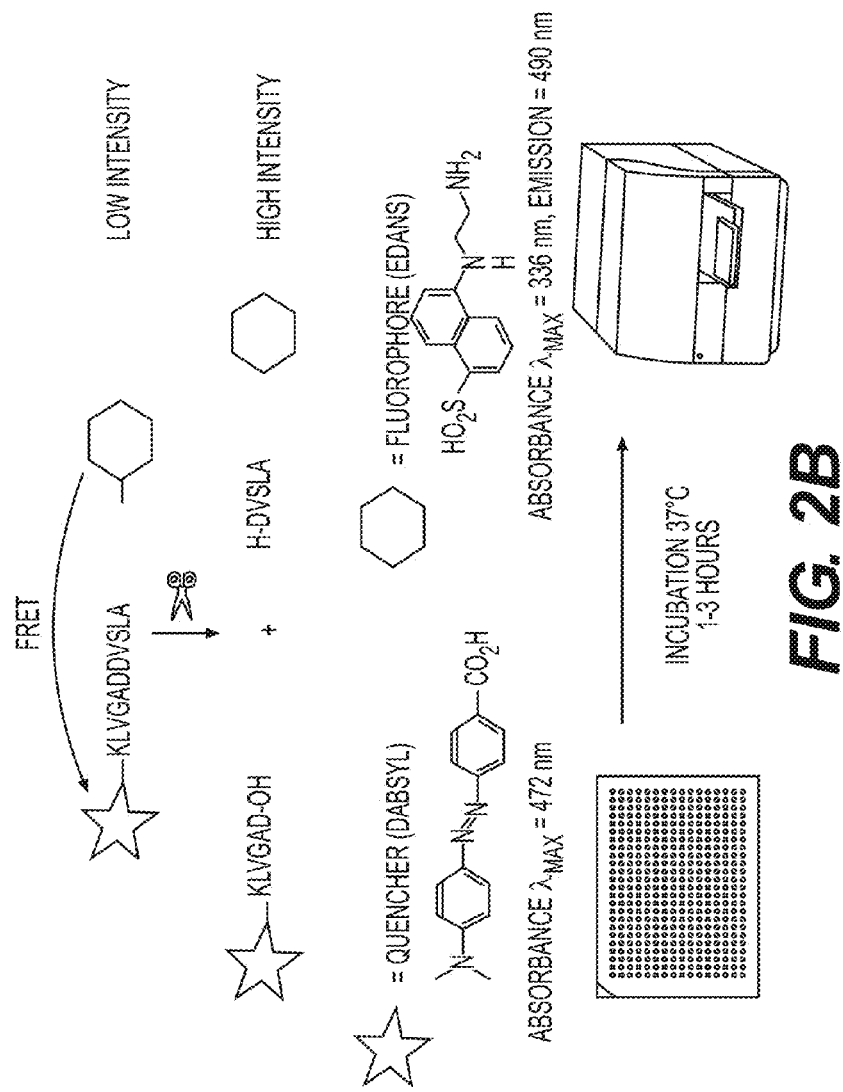
FIG. 2B is a schematic representation of a FRET-based PvSUB1-specific enzymatic assay according to an embodiment of the invention. PvSUB1 substrate KLVGADDVSLA (SEQ ID NO: 9). KLVGAD (SEQ ID NO: 26). DVSLA (SEQ ID NO: 25).
Figure 2C:
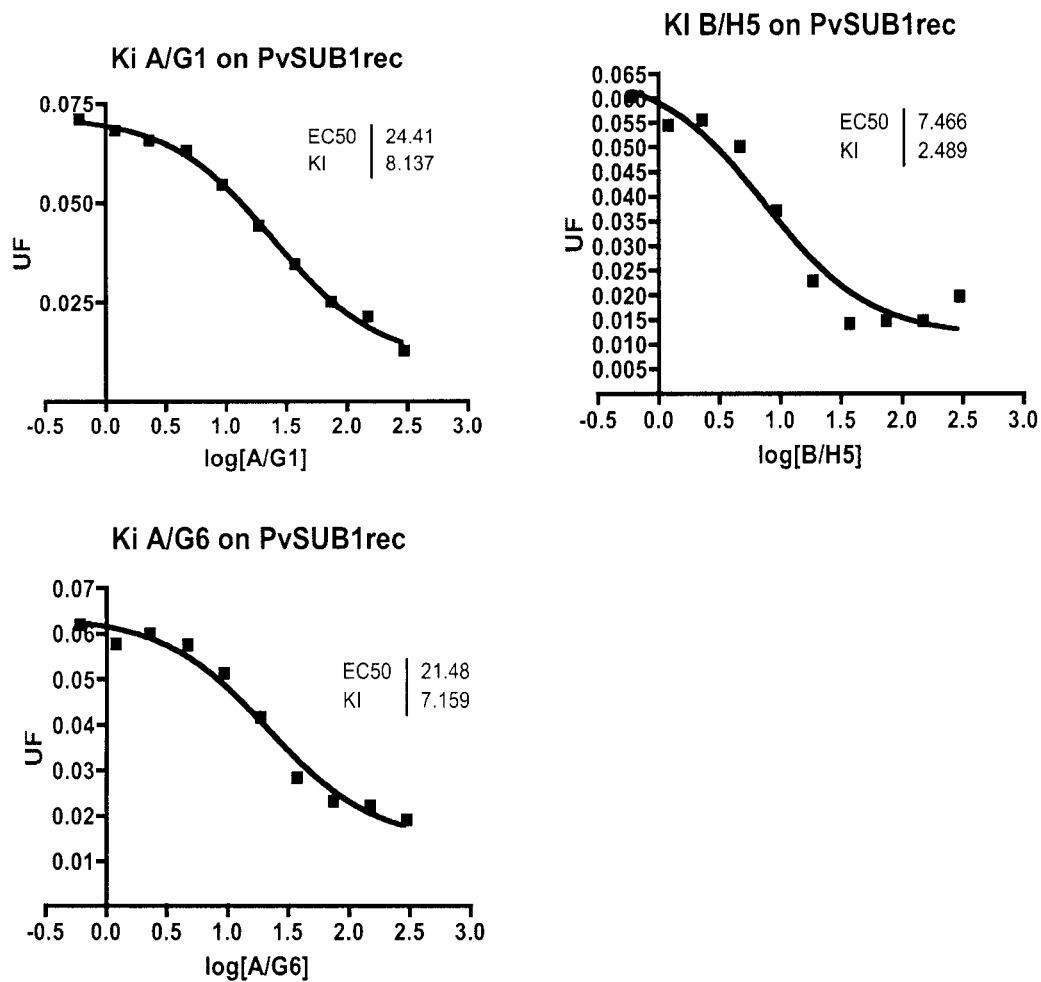
FIG. 2C is are line graphs providing the determination of the Ki of compounds AG6, AG1 and BH5 for the recombinant PvSUB1 enzyme with the Dabsyl Edans substrate.

FIG. 2B depicts the FRET-based specific enzymatic assay which was used. In this particular case the assay consists in measuring fluorescence of tagged peptidic substrate of SUB1. An uncleaved peptide has low intensity emission whereas, when the peptide is cleaved by SUB1, high intensity emissions are measured. Hereinafter the Table 3 shows the different substrates that were used (amino acid sequence, the quencher and the fluorofore (Dabcyl/EDANS or Far Red)). Molecules where thus tested and their Ki (inhibition constant) was determined on the PvSUB1 recombinant enzyme. FIG. 2C provides determination of the Ki of the AG6, AG1 and BH5 compounds for the recombinant PvSUB1 enzyme with the Dabsyl Edans substrate. Ten different concentrations, ranging from 300 μM to 585 nM following sequential 1:2 dilutions, of the compounds were tested using the PvSUB1 enzymatic assay. The final mixture was distributed in dupli-

TABLE 2

Similarity and identity percentages between the full length and enzymatic forms of SUB1 orthologs.

| | % Similarity | | | | | | | | | | |
|---|---|---|---|---|---|---|---|---|---|---|---|
| | Full length | | | | | Enzymatic form | | | | | |
| PbSUB1 | 100 | 89.3 | 62.8 | 64.2 | 57.9 | 100 | 95.3 | 64.6 | 66.7 | 62.7 | % identity |
| PySUB1 | 86.1 | 100 | 64.7 | 65.9 | 59.2 | 91.8 | 100 | 65.5 | 67.4 | 63.3 | |
| PvSUB1-Sal1 | 52.8 | 53.4 | 100 | 98.1 | 64.1 | 53.1 | 54.1 | 100 | 97.4 | 66 | |
| PvSUB1-Bellem | 54 | 54.7 | 98.1 | 100 | 65.8 | 55 | 55.9 | 97.4 | 100 | 68.3 | |
| PfSUB1-3D7 | 49.2 | 49.9 | 55.2 | 56.5 | 100 | 54 | 54.9 | 58.4 | 60.3 | 100 | |
| | Pb SUB1 | Py SUB1 | Pv SUB1-Sal1 | Pv SUB1-Belem | Pf SUB1-3D7 | Pb SUB1 | Py SUB1 | Pv SUB1-Sal1 | Pv SUB1-Belem | Pf SUB1-3D7 | |

The PvSUB1, PfSUB1 and PbSUB1 recombinant purified enzymes expressed using the baculovirus/insect cells expression system, in combination with a FRET assay, were used for Ki determination. The nucleotide and the amino acid sequences of each of PvSUB1, PfSUB1 and PbSUB1 are shown in FIGS. 4A to 6B. The nucleotide sequences of PfSUB1 and PbSUB1 was "recodoned" for avoiding codon bias of the *Plasmodium* open reading frames compared to other organisms, including insect cells.

Briefly, SUB1 proteins exist under a pro-form (80 kDa) and an active form (48-50 kDa). FIG. 2A top panel shows a scheme of PvSUB1 precursor and auto-maturated active form, PvSUB1 is synthesized as a precursor of 80 kDa, undergoes auto-maturation to produce the active enzyme of 48-50 kDa, which N-terminal (DVSLA) sequence is shown. The amino-acids involved in PvSUB1 active site (D, H, N, S) are shown.

FIG. 2A middle panel shows HPLC fractions containing pure active recombinant PvSUB1. HPLC-fractions of purified recombinant PvSUB1 were analyzed by SDS-PAGE stained with Coomassie blue. The active form of PvSUB1 enzyme (48-50 kDa) and its pro-region (25 kDa) accumulate mostly in fractions B7 and B8. Molecular weights are indicated in kDa.

HPLC-fractions of purified recombinant PvSUB1 were tested for enzymatic activity using the FRET-specific based assay. For each HPLC-fractions, the enzymatic initial velocity (V, expressed in Arbitrary Fluorescence Unit/minutes) has been determined, showing that PvSUB1 active enzyme accumulates mostly in fractions B7 and B8 (FIG. 2A bottom panel), thereby demonstrating that the recombinant purified PvSUB1 is an active enzyme.

cate into a 384-well black microtiter plate (Thermo Scientific) and the fluorescence was monitored. The slope of the linear part of the kinetic was determined in an Excel™ (Microsoft) spreadsheet. The Ki and EC50 values expressed in μM were determined using GraphPad Prism™ software. Out of the tested molecules, the ones with a Ki less than 50 μM were retained for determination of their anti-parasite effect (IC50) on the in vitro culture of the chloroquino-sensitive (3D7) and chloroquino-resistant (Dd2) *P. falciparum* clones according to Desjardins et al. (Desjardins et al. Antimicrob Agents Chemother. 1979 December; 16(6):710-8). Exemplary results are presented in Table 4 hereinafter. The fact that there is a very good correlation between Ki and IC50 for the compounds tested suggests that the anti-parasitic effect observed is likely to be the consequence of the inhibition of the PfSUB1 enzyme.

TABLE 3

Different substrates used for FRET-based SUB1 enzymatic test.

| | |
|---|---|
| PvSUB1 Dabsyl Edans substrate | Dabsyl- K-L-V-G-A-D-D-V-S-L-A-EDANS (SEQ ID NO: 9) |
| PvSUB1 FAR RED substrate | DYQ660- K-L-V-G-A-D-D-V-S-L-A-K-DY630 (SEQ ID NO: 10) |
| PfSUB1 Dabsyl Edans substrate | Dabsyl- K-L-V-S-A-D-N-I-D-I-S-EDANS (SEQ ID NO: 11) |

TABLE 4

Properties of PvSUB1 and *P. falciparum* in vitro growth inhibitors*.

| Compound | A/G1 | A/G6 | B/H5 | chloroquine |
|---|---|---|---|---|
| Molecular Weight (MW) (Daltons) | 432 | 399 | 468 | 319.9 |
| logP (solubility) | 3.61 | 5.06 | 5.01 | — |
| Virtual screening method | 1cm kcal | FlexX ™ (kJ) | 1cm kcal | — |
| PvSUB1 3D-model template | 34 | 20 | 34 | — |
| Ki on recombinant PvSUB1 (μM) | 5.5 ± 2.4 | 8.2 ± 1.9 | 1.4 ± 1.0 | — |
| IC50 on *P. falciparum* 3D7 strain (μM) | 4.7 ± 1.8 | 17.7 ± 1.7 | 16.9 ± 3.3 | 4.3 ± 1.3 (ng/ml) |
| IC50 on *P. falciparum* Dd2 strain (μM) | 3.5 ± 1.7 | 14.8 ± 6.7 | 13 ± 8.1 | 35.5 ± 13.7 (ng/ml) |

*The molecular weight, calculated logP of compounds tested on in vitro culture of *P. falciparum* chloroquino-sensitive clone 3D7 and chloroquine-resistant clone Dd2 are presented. The in silico screening method and the score they obtained, together with the PvSUB1 3D-model on which they have been selected are shown. The Ki and IC50 values are expressed as the mean of at least three independent experiments ± SEM.

Figure 3A:
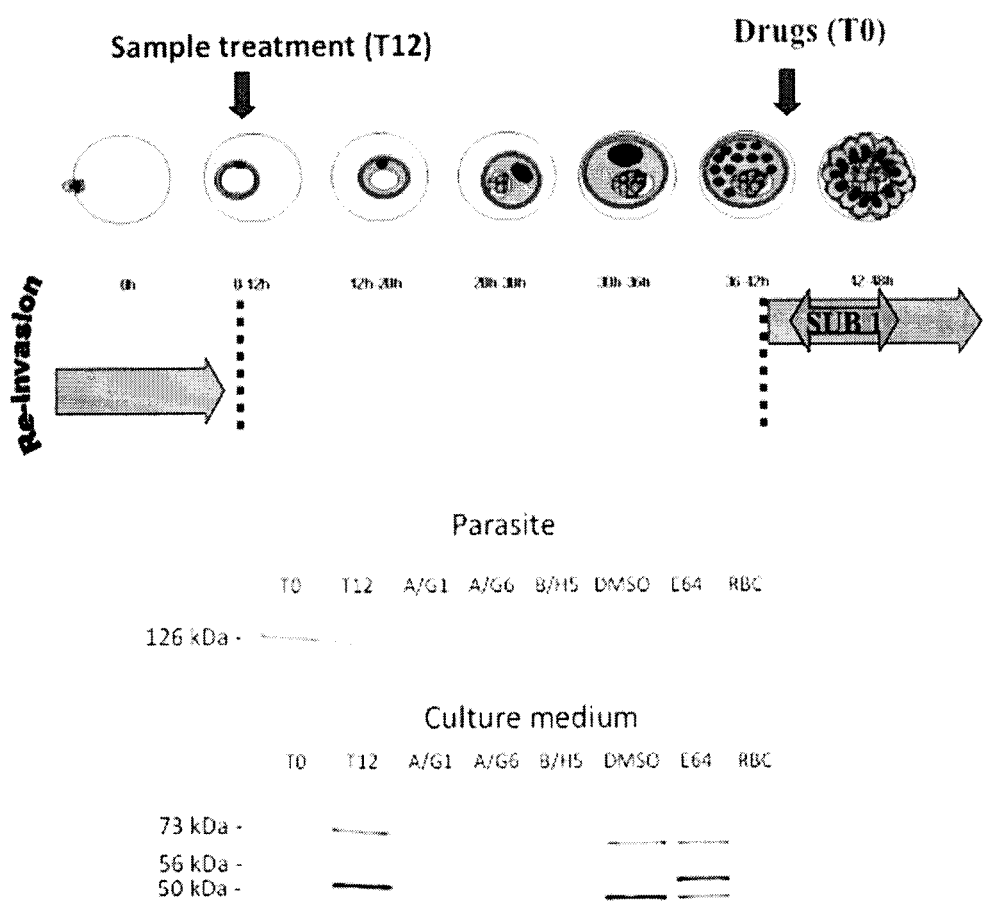
FIGS. 3A and 3B are panels depicting evaluation of selected SUB1 inhibitors for their impact on *P. falciparum* 3D7 stage-specific ex vivo culture.
Figure 3B:
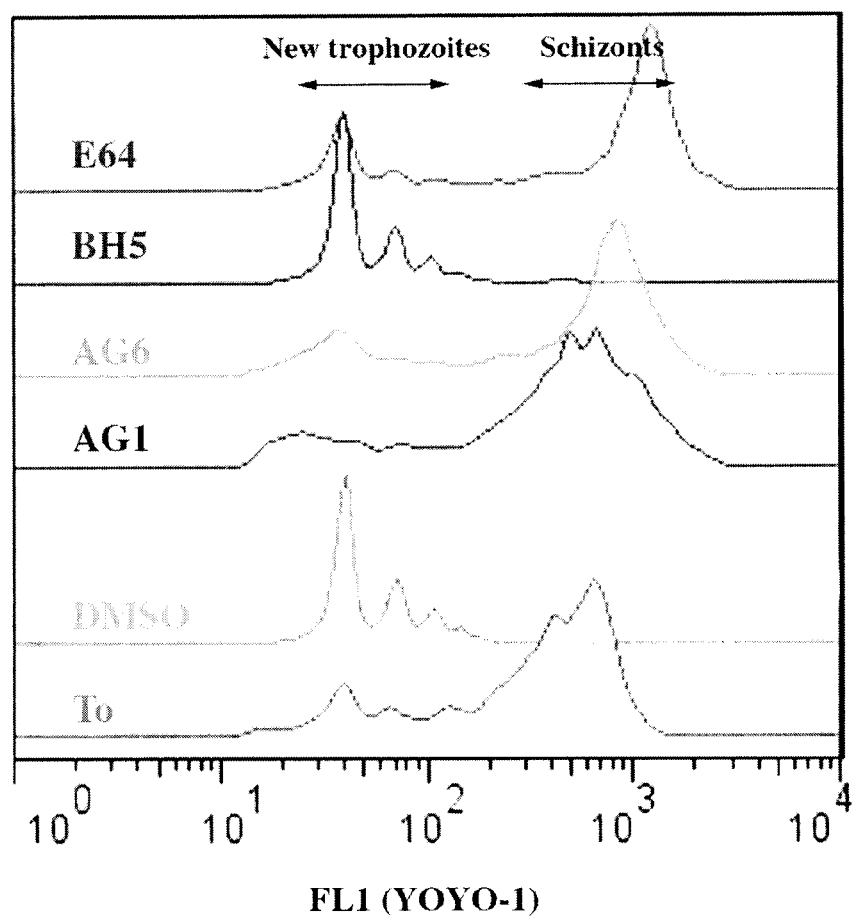

Next, the selected SUB1 inhibitors were evaluated biologically for their impact on *P. falciparum* 3D7 stage-specific ex vivo culture. FIG. 3A shows inhibition of the maturation of PfSUB1's natural substrate SERA5. In vitro synchronized culture of *P. falciparum* composed of 0.5% of segmented schizonts (To) was cultivated for 12 hr in serum-free medium in the absence (T12) or presence of DMSO (0.9% v/v) (lane DMSO). Lanes A/G1, A/G6, B/H5 correspond to parasites incubated with 90 μM of corresponding compounds. Lanes E64 and RBC correspond to parasites cultured in presence of E64 (10 μM) and uninfected erythrocytes respectively. Parasite extracts and culture supernatants were analyzed by western blot with mAb 24C6.1F1. SERA5 126 kDa precursor and its processed forms of 73, 56 and 50 kDa are indicated. FIG. 3B shows inhibition of the merozoites egress/invasion steps on *P. falciparum* in vitro culture. Segmented schizonts (starting material, To) were cultivated for 12 hr in serum-containing medium and their transition to newly formed trophozoites-stages in presence of 0.9% DMSO (DMSO) was analysed by flow cytometry using YOYO1 Facs technique (Li et al, Cytometry, 71A, 297-307, 2007). Gates were selected to exclude uninfected erythrocytes and converted to two-dimensional plots illustrating the consequence of the presence of tested compounds on the arrest of schizogony. All compounds were tested at 90 μM, except E64 tested at 10 μM. The results show the inhibition of the SERA 5 maturations and of the egress of the merozoites. As seen in western blots at bottom of FIG. 3A, the maturation of SERA5 by SUB1 successive cleavages is inhibited by all the test compounds, while the presence of DMSO or of an inhibitor of another protease (E64) are inactive on SERA5 maturation. As seen in FIG. 3B, the compounds A/G6 and A/G1 were able to maintain the parasites to the schizonts stage while, with the negative control (DMSO), the parasites evolved to the subsequent ring stage. Since PfSUB1 is known to be crucial for the merozoite egress, and since PvSUB1 inhibitors affect *P. falciparum* merozoites egress, these results demonstrate that PvSUB1 inhibitors also inhibit endogenous PfSUB1 enzyme ex vivo, thus explaining the anti-*P. falciparum* activity of the compounds.

Finally, the compounds were tested in vivo on *P. berghei*-infected mice. The compounds inhibited red blood cell infection in a dose-dependent manner. It was estimated that the compounds has a LD50 of about 33 mg/kg (LD50 of chloroquine is about 2 mg/kg) without showing any obvious signs of toxicity.

Altogether these results demonstrate that targeting a *Plasmodium vivax* therapeutic target leads to the selection and the validation of chemical compounds having a potent activity against different *Plasmodium* species, which are responsible for the severe forms of malaria. Therefore the screening methods and the chemical compounds described herein are potentially useful in anti-malaria therapy and prophylaxis against at least the two main *Plasmodium* infecting humans: *P. vivax* and *P. falciparum*.

Example 2

Screening Method to Select Inhibitors of *Plasmodium* Modeling of PvSUB1 and PfSUB1 Active Sites The homology modeling procedure was realized using the suite of tools, Biskit. In many ways, Biskit presents features to produce models as accurate as possible (Grünberg R, et al., A software platform for structural bioinformatics, Bioinformatics. 2007, 23(6):769-70). The multiple alignments and the construction of models are the most critical task of modeling. Biskit use respectively 3DCoffee™ (O'Sullivan et al. 3DCoffee: combining protein sequences and structures within multiple sequence alignments. J Mol Biol. 2004, 340(2):385-95) and Modeller™ (Sall and Blundell. Comparative protein modeling by satisfaction of spatial restraints. J Mol Biol 1993, 234(3): 779-815). For this study, modeling of PvSUB1 enzyme is restricted to its catalytic domain from residue 1302 to P586, which present a significant homology to bacterial subtilisins. Proteins structures displaying significant sequence similarities with PvSUB1 were searched in the PDB (Protein Data Bank) database using Blast (Altschul et al. Basic local alignment search tool. J Mol Biol. 1990, 215(3): 403-10). Several homologous proteins have been identified and only proteins with an e-value less than 0.001 and a resolution inferior to 2.5 A were considered. Then, structures were clustered according to their sequence similarities using Blastclust with the parameters simcut 1.75 and simlen 0.9 thereby doing 7 clusters. We decided to keep as template the structure of best resolution in each cluster, selecting in this way 7 templates, presented in the Table 5. The sequence identities of the catalytic domain of these templates with PvSUB1 and PfSUB1's are shown in Table 6.

TABLE 5

Subtilisin structures used as templates to build the PvSUB1 SD-model. 1IC6 corresponds to the SD-structure of the proteinase K, an eukaryotic subtilisin, while others are 3D-structures of bacterial enzymes. 1EA7, 1DBI, 1IC6 correspond to proteins in a free state and others to proteins bound to a peptidic inhibitor (2TEC, 1R0R, 1LW6, 1CGI).

| PDB Code | Enzyme | Resolution | IUBMB Enzyme | Inhibitor | Species | date |
|---|---|---|---|---|---|---|
| 1LW6 | Subtilisin BPN' | 1.50 Å | 3.4.21.62 | Inhibitor of the serine protease of the CI-2A family | *Bacillus amyloliquifaciens* | 2002 |

TABLE 5-continued

Subtilisin structures used as templates to build the PvSUB1 SD-model. 1IC6 corresponds to the SD-structure of the proteinase K, an eukaryotic subtilisin, while others are 3D-structures of bacterial enzymes. 1EA7, 1DBI, 1IC6 correspond to proteins in a free state and others to proteins bound to a peptidic inhibitor (2TEC, 1R0R, 1LW6, 1CGI).

| PDB Code | Enzyme | Resolution | IUBMB Enzyme | Inhibitor | Species | date |
|---|---|---|---|---|---|---|
| 1EA7 | Sphericase | 0.93 Å | | / | *Bacillus Sphaericus* | 2002 |
| 2TEC | Thermitase | 1.98 Å | 3.4.21.66 | eglin C (Potato inhibitor I family) | *Thermoactinomyces vulgaris* | 1992 |
| 1DBI | AK.1 Serine protease | 1.80 Å | | / | *Bacillus* sp. | 1999 |
| 1R0R | Subtilisin Carlsberg | 1.10 Å | 3.4.21.62 | Ovomucoid (Protein Inhibitor OMTKY3) | *Bacillus licheniformis* | 2003 |
| 1IC6 | Proteinase K | 0.98 Å | 3.4.21.64 | / | *Tritirachium album* | 2001 |
| 1GCI | *Bacillus lentus* Subtilisin | 0.78 Å | 3.4.21.62 | / | *Bacillus lentus* | 1998 |

TABLE 6

Sequence identity of catalytic domains of subtilisin homologues used as templates to build PvSUB1 and PfSUB1 3D-models.

| | 2TEC | 1DBI | 1GCI | 1R0R | 1LW6 | 1EA7 | 1IC6 | PfSUB1 | PvSUB1 |
|---|---|---|---|---|---|---|---|---|---|
| 2TEC | 100 | 62 | 50 | 48 | 45 | 39 | 37 | 28 | 31 |
| 1DBI | 62 | 100 | 44 | 43 | 45 | 37 | 36 | 29 | 35 |
| 1GCI | 50 | 44 | 100 | 62 | 61 | 42 | 39 | 32 | 33 |
| 1R0R | 48 | 43 | 62 | 100 | 70 | 42 | 37 | 32 | 33 |
| 1LW6 | 45 | 45 | 61 | 70 | 100 | 38 | 37 | 31 | 34 |
| 1EA7 | 39 | 37 | 42 | 42 | 38 | 100 | 34 | 22 | 29 |
| 1IC6 | 37 | 36 | 39 | 37 | 37 | 34 | 100 | 25 | 25 |
| PfSUB1 | 31 | 35 | 33 | 33 | 34 | 29 | 25 | 100 | 75 |
| PvSUB1 | 33 | 36 | 34 | 33 | 36 | 29 | 25 | 75 | 100 |

To be meaningful and reliable, a multiple sequence requires a large number of aligned sequences. Thus, protein sequences were also searched in the non-redundant sequence database of the Swiss-Prot Protein Knowledgebase (Boeckmann B. et al., The Swiss-Prot Protein Knowledgebase and its supplement TrEMBL in 2003. Nucleic Acids Res. 31:365-370 (2003); www.ncbi.nlm.nih.gov) displaying significant with an e value <0.01. 73 sequences clustered according to their similarities into 50 clusters, from each of which the member of longest sequence was further considered. The multiple sequence alignment of the target sequence in addition to the 7 template sequences and the additional 50 homologous sequences (Table 7) was performed using 3DCoffee™ which rely on structural alignments and local sequence alignment in order of producing a global alignment of all sequences (O'Sullivan, 2004, supra; Dalton and Jackson. An evaluation of automated homology modelling methods at low target template sequence similarity. Bioinformatics 2007, 23(15): 1901-8). Modeller™ version 7v7 was used to construct 50 3D-models of PvSUB1, guided from the sequences alignment and the 7 templates structures.

Selection and Validation of the 3D Models

The quality of the 3D-models was verified with ProCheck™ PROCHECK and Prosa II™ (Laskowski et al. PROCHECK: a program to check the stereochemical quality of protein structures. J of Applied Crystallography 1993, 26(2): 283-291). The structures analyzed by the ProCheck™ program present only few residues in disabled region of the Ramachandran diagram. These residues are situated in large inserted loops which mainly correspond to insertions into the PvSUB1 or PfSUB1 sequences compared to the templates, which can explain some deviation with respect to statistically observed geometries in experimental structures.

The ab initio construction by Modeller™ of these regions does not guaranty a reliable geometry. Nevertheless, such imprecision does not alter the correct construction of the binding site.

The active site was almost identical in all models, as expected from the very small deviation observed in the corresponding region of the template structures. The global root mean square deviation (RMSD) on all main chain atoms observed between the models was close to 2 Å. However, as could be anticipated, the main differences were found in the topology of the large inserts situated at the surface of the protein, far from the active site. The RMSD between all models calculated on all atoms of the active site pocket was equal to 0.1 Å. In other words, they were basically equivalent in this region, and the level of confidence in the conformation of the modeled active site was high, which allowed choosing one of the models for the following studies.

DEFINITION AND SETTING UP OF THE BINDING POCKET

A suitable characterization of the residues composing the binding pocket is a prerequisite to restrict the docking to a relevant area of the catalytic site. Competitive inhibitors should bind and interact with these selected residues.

The binding pocket was selected by superimposition of the PvSUB1 model to one of its template, the crystallographic structure of thermitase bound to the subtilisin inhibitor Eglin (2TEC) (Gros et al., Molecular dynamics refinement of a thermitase-eglin-c complex at 1.98 Å resolution and comparison of two crystal forms that differ in calcium content. J Mol Biol. 1989, 210(2): 347-67). Binding site was defined by the residues of PvSUB1 model which have at least one atom up to 6 Å from the Eglin pentapeptide P1'-P5. This region corresponds to the burriest part of the active site, which is as described by Siezen & Leunissen (Siezen and Leunissen. Subtilases: the superfamily of subtilisin-like serine proteases. Protein Sci. 1997, 6(3): 501-23.) primary for the substrate recognition. Moreover the Icm Pocket-Finder algorithm based on the exploration of the whole enzyme surface predicts/detects this same region as the most "druggable" pocket. Thus, the active site used for all docking experiments was composed of the entire residues D316, S317, N370, Y371, H372, L405, D406, H408, L410, G411, M416, S434, F435, S436, S461, A462, S463, N464, C465, P473, Y486, P488, Y511, L545, N546, G547, T548, S549 and M550. Consistent with the first step of the catalytic mechanism, the side chain of residue H372 that belongs to the catalytic triad was described in its uncharged form, i.e. with a single proton born by the $N^d$ nitrogen atoms of the indole ring.

TABLE 7

References of non-redundant sequences homologous to PvSUB1 extracted from the Swiss-Prot database and used to perform the multiple alignment.

| Entry | Protein | Enzyme code |
|---|---|---|
| SUBT_BACAM | Subtilisin BPN' precursor | EC 3.4.21.62 |
| P1P_LACLC | PI-type proteinase precursor | EC 3.4.21.— |
| NEC1_HUMAN | Neuroendocrine convertase 1 precursor | EC 3.4.21.93 |
| PRTM_BACSP | M-protease | EC 3.4.21.— |
| SCA2_STRPY | C5a peptidase precursor | EC 3.4.21.— |
| PAC4_HUMAN | Paired basic amino acid cleaving enzyme 4 precursor | EC3.4.21.— |
| FURI_BOVIN | Furin precursor | EC 3.4.21.75 |
| ORYZ_ASPFU | Oryzin precursor | EC 3.4.21.63 |
| PRTR_TRIAL | Proteinase R precursor | EC 3.4.21.— |
| ELYA_BACAO | Alkaline protease precursor | EC 3.4.21.— |
| SUBF_BACSU | Bacillopeptidase F precursor | EC 3.4.21.— |
| PLS_PYRFU | Pyrolysin precursor | EC 3.4.21.— |
| XPR6_YARLI | Dibasic processing endoprotease precursor | EC 3.4.21.— |
| BLI4_CAEEL | Endoprotease bli-4 precursor | EC 3.4.21.— |
| WPRA_BACSU | Cell wall-associated protease precursor | EC 3.4.21.— |
| SUBV_BACSU | Minor extracellular protease vpr precursor | EC 3.4.21.— |
| SUB2_DEIRA | Probable subtilase-type serine protease DRA0283 precursor | EC3.1.24.— |
| NISP_LACLA | Nisin leader peptide processing serine protease nisP precursor | EC 3.4.21.— |
| SUBE_BACSU | Minor extracellular protease epr precursor | EC 3.4.21.— |
| BPRV_BACNO | Extracellular basic protease precursor | EC 3.4.21.— |
| BPRX_BACNO | Extracellular subtilisin-like protease precursor | EC 3.4.21.— |
| EXPR_XANCP | Extracellular protease precursor | EC 3.4.21.— |
| PROA_VIBAL | Alkaline serine exoprotease A precursor | EC 3.4.21.— |
| PEPC_ASPNG | Subtilisin-like serine protease pepC precursor | EC 3.4.21.— |
| HLY_HAL17 | Halolysin precursor | EC 3.4.21.— |
| AQL1_THEAQ | Aqualysin I precursor | EC 3.4.21.— |
| YCT5_YEAST | Putative subtilase-type proteinase YCR045C precursor | EC 3.4.21.— |
| YSP3_YEAST | Subtilisin-like protease III precursor | EC 3.4.24.— |
| ISP6_SCHPO | Sexual differentiation process putative subtilase-type proteinaseisp6 | EC 3.4.21.— |
| EPIP_STAEP | Epidermin leader peptide processing serine protease epiPprecursor | EC 3.4.21.— |
| YLP1_SCHPO | Hypothetical subtilase-type proteinase C1006.01 in chromosome I | EC 3.4.21.— |
| TKSU_PYRKO | Tk-subtilisin precursor | EC 3.4.21.— |
| SUBT_BACS9 | Subtilisin precursor | EC 3.4.21.62 |
| ALP_TRIHA | Alkaline proteinase precursor | EC 3.4.21.— |
| SEPR_THESR | Extracellular serine proteinase precursor | EC 3.4.21.— |
| SMP1_MAGPO | Subtilisin-like proteinase Mp1 precursor | EC 3.4.21.— |
| ORYZ_ASPFL | Oryzin precursor | EC 3.4.21.63 |
| ALP_CEPAC | Alkaline proteinase precursor | EC 3.4.21.— |
| THES_BACSP | Thermophilic serine proteinase precursor | EC 3.4.21.— |
| CUDP_METAN | Cuticle-degrading protease precursor | EC 3.4.21.— |
| SUBT_BACLI | Subtilisin Carlsberg precursor | EC 3.4.21.62 |
| ELYA_BACSP | Alkaline elastase YaB precursor | EC 3.4.21.— |
| ELYA_BACHD | Thermostable alkaline protease precursor | EC 3.4.21.— |
| ISP_PAEPO | Intracellular serine protease | EC 3.4.21.— |
| ISP_BACCS | Intracellular alkaline protease | EC 3.4.21.— |
| ISP1_BACSU | Major intracellular serine protease | EC 3.4.21.— |
| PRTT_TRIAL | Proteinase T precursor | EC 3.4.21.— |
| THET_THEVU | Thermitase | EC 3.4.21.66 |
| SUBT_BACPU | Subtilisin | EC 3.4.21.62 |
| SUBD_BACLI | Subtilisin DY | EC 3.4.21.62 |

Set Up of the Chemical Database

The virtual screening was performed using the commercially available compounds from Chemdiv, Inc (chemdiv.com). The Chemdiv molecules were filtered using the program Filter (openeye.com), with standard parameters to select "drug-like" compounds. Predicted aggregators and toxic compounds were also eliminated. The 149 992 remaining compounds were converted as 3D conformers corresponding to a structure of minimized energy was generated with Corina (molecular-networks.com) and considered as an entry for the screening described above.

Virtual Screening

We used two of the most performing docking programs Icm (Totrov and Abagyan. Flexible protein-ligand docking by global energy optimization in internal coordinates. Proteins 1997, Suppl 1: 215-20) and FlexX™ (Rarey et al., A fast flexible docking method using an incremental construction algorithm. J Mol Biol. 1996, 261(3): 470-89), to extract relevant in silico hits from the selected 149 992 drug-like compounds. Icm was applied with its standard parameters. In parallel, we used FlexX to select a second pool of compounds. Unlike Icm, which requires 30 s to 1 minute to dock one compound, FlexX™ is faster, allowing to process different screening conditions. Thus FlexX™ was run using 3 different 3D-models of PvSUB1 selected from the 50 generated by Modeller™.

Screening was also performed, under pharmacophore restraints (Hindle, 2002). In many cases, the resolved subtilisins 3D-structures available in the PDB correspond to a complex composed of the enzyme catalytic domain co-crystallised with an inhibitor. We focused on 1 LW6, 1 R0R, 2TEC and on 1 BH6: the analyses of these four structures show that five inter-molecular hydrogen bonds are conserved and are involved in the interactions between conserved subtilisins residues and their ligands.

Therefore, we postulated that a screening protocol selecting molecules able to bind PvSUB1 using these conserved hydrogen bonds would help identifying better competitive inhibitors. However, a preliminary test using these four hydrogen bonds as a pharmacophore restraint was shown to be too drastic to find any docking solution. Therefore, we used FlexX™ to select molecules predicted to interact with the PvSUB1 3D-models with two of these four conserved hydrogen bonds.

PfSUB1 and PvSUB1 Production

Recombinant baculoviruses expressing recombinant forms of PvSUB1 and PfSUB1 were amplified by infecting $5 \times 10^6$ Sf9 cells in T-25 culture cultivated in Insect XPRESS medium (Lonza) supplemented with 5% fetal calf serum and 50 mg/L gentamycin. The final viral stock was titrated by end-point dilution assay. For large-scale protein production, Sf9 cells (1 L at $3 \times 10^6$ cells/mL) were infected for 72 h with recombinant baculovirus at a MOI of 10 in Insect Xpress™ medium supplemented with 50 mg/L gentamycin and 0.5 µg/mL of tunicamycine.

PfSUB1 and PvSUB1 Purification

PvSUB1 and PfSUB1 Culture supernatant containing the secreted and active PvSUB1 or PfSUB1 recombinant enzymes was harvested, centrifuged 30 min at 2150 rcf to remove cells and cellular debris and concentrated/diafiltrated against D-PBS 0.5 M NaCl; 5 mM Imidazole (loading buffer). The protein was purified on an AKTA™ purifier system (GE Healthcare). The sample was loaded onto a 3 mL TALON™ Metal affinity resin (Clontech Laboratories) previously equilibrated in loading buffer, thus allowing the binding of PvSUB1 or PfSUB1 recombinant proteins via the addition of a 6x-histidines tag in its C-terminal. The column was extensively washed with loading buffer and the bound protein was eluted with a linear gradient from 5 to 200 mM imidazole in D-PBS 0.5 M NaCl. Fractions containing PvSUB1 or PfSUB1 were pooled concentrated using a Amicon Ultra 15™ (10000 MWCO) and size fractionated onto a HiLoad™ 16/60 Superdex™ 75 column equilibrated with 20 mM Tris pH 7.5, 100 mM NaCl to remove imidazole and exchange buffer. Throughout the purification procedure, fractions were monitored by absorbance (280 nm) and analyzed by Coomassie blue staining of SDS-PAGE gels and activity assay. Fractions containing the PvSUB1 or PfSUB1 purified proteins were pooled, and protein concentration was determined using the BCA Protein Assay following manufacturer's recommendations (Bio Basic). Purified PvSUB1 or PfSUB1 recombinant proteins were stored at −20° C. following the addition of 30% v/v of pure glycerol.

PfSUB1 and PvSUB1 Enzymatic Assays

For the kinetic assays we used the recombinant PvSUB1/PfSUB1 enzymes and specific peptide substrates whose sequence are deduced from the auto-maturation site of each one: KLVGADDVSLA (SEQ ID NO: 9), which cleavage occurs between the two aspartates for PvSUB1 and KLVSADNIDIS (SEQ ID NO: 11) which is cleaved between the aspartate and the asparagine for PfSUB1. The substrates used had the fluorophores/quencher Dabsyl/Edans or DYQ660/DY630 at each edge. The enzymatic assays were performed with 13 ng of purified PvSUB1 or PfSUB1 in 20 mM Tris pH 7.5 and 25 mM CaCl2 at 37° C. The apparent Km of PfSUB1 and PvSUB1 for their substrate being 30.2 µM±3.4 and 19.7 µM±1.7 respectively, all further experiments were performed using 25 µM of substrates. For the determination of the Ki, the compounds, previously resuspended in 100% DMSO at 10 mM, were tested at ten different concentrations ranging from 300 µM to 585 nM following sequential 1:2 dilutions. The final mixture was distributed in duplicate into a 384-well black microtiter plate (Thermo Scientific) and the fluorescence was monitored every 3 minutes for 90 min at 37° C. in a Labsystems Fluoroskan Ascent™ spectrofluorometer or a Tecan Infinite M1000™ spectrofluorometer using the excitation and emission wavelengths of 460/500 nm or 620/680 nm for the Dabsyl/Edans or DYQ660/DY630 substrates respectively. The slope of the linear part of the kinetic was determined in an Excel™ (Microsoft) spreadsheet. Every steps of the enzymatic assay were done on ice to make sure that the protein was not active before the measure of the fluorescence. The Ki and IC50 values were determined (N=3) using GraphPad Prism™ software.

The enzymatic assay using approximately 13 ng of purified PvSUBI, in 20 mM Tris pH 7.5 and 25 mM CaCl2 at 37° C. in presence of 25 µM the Dabsyl-KLVGADDVSLA-Edans (Dabsvl-SEQ ID NO: 9-EDANS) has been validated on 384-well plates and is suitable for High Throughput Screening (HTS) with an average Z−0.52±0.04 [Zhang et al 1999, J Biomol Screen 4(2):67-73].

Culture Tests

Parasite Culture and In Vitro Drug Susceptibility Assay

Asexual cultures of reference clone 3D7 obtained from MR4 (MR4.org) was maintained in continuous cultures following the method of Trager and Jensen [1976, Science 193: 673-5], except that the medium was composed of RPMI 1640 medium supplemented with 10% decomplemented human serum (AB+), hypoxanthine 100 µM, gentamycin 50 ng/ml_. Parasites were incubated at 37° C. in an atmosphere composed of 5% O2, 5% CO2 and 90% N2. Quantitative assessment of the antimalarial activity of test compound was performed as described by Desjardins et al[1979, Antimicrob Agents Chemother 16:710-8.] and Bougdour et al[2009, J Exp Med 206: 953-66] on asynchronous culture of clone 3D7 (0.5% parasitemia and 1% hematocrit), except that the parasites were in contact with the drug for 48 hours, the culture medium contained 10 µM hypoxanthine. IC50/EC50 have been determined following nonlinear regression analysis using HN-NonLin V1.1 software (malaria.farch.net).

Flow Cytometry Analysis

A synchronised culture composed of segmented schizonts of *P. falciparum* (3D7 clone) at 0.5% parasitemia and 1% hematocrit is performed in a 24 wells plate. An aliquot corresponding to 10% of the starting culture (T0) is diluted in a solution at 0.04% of glutaraldehyde in PBS (Dulbecco) and store at 4° C. for further flow cytometry analysis. E64, a cysteine-protease inhibitor known to block the egress of *P. falciparum* merozoites in vitro [Salmon et al. 2001 Proc Natl Acad Sci USA 98: 271-6.] was used as a positive control at a final concentration of 10 µM, while the compounds were tested at a final concentration of 90 µM and a mock control (DMSO) received 0.9% DMSO, in which compounds are resuspended. The final experiment ended after an incubation of 12 hours, allowing the rupture of the parasitized erythrocytes, the egress of merozoites and their subsequent entry into fresh red blood cells. 10% of the cultures are resuspended in a solution of 0.04% glutaraldehyde in PBS (Dulbecco) and store at 4° C. for flow cytometry analysis. The progress of the parasitaemia from segmented schizont to newly formed trophozoites was assessed by flow cytometry after staining samples by the DNA-binding fluorescent dye, YOYO-1™, as previously described by Li and colleagues [2007, Cytometry A 71: 297-307.] with some modifications. Briefly, following a centrifugation at 450 g for 5 min the pelleted cells were re-suspended in 0.3 ml PBS (Dulbecco) supplemented with 0.25% Triton X-100™ and incubated for 10 min at room temperature. After centrifugation, the permeabilized cells were re-suspended in 500 µL of RNase at 50 µg/mL and incubated for at least 3 h at 37° C. Then YOYO-1™ solution (Invitrogen) was added to obtain a final concentration of 500 ng/mL. Samples were incubated at 4° C. in darkness for at least 4 h and centrifuged at 450 g for 5 min. The pelleted cells were re-suspended in 0.3 ml PBS before being analysed by flow cytometry using a FACSCanto™ (BD) apparatus and the data were analyzed using FlowJo™ (Tree Star) software. The fluorescent signal of YOYO-1™ dying cells was collected in FL-1 channel after compensation of fluorescent intensity in the FL-2 channel.

Headings are included herein for reference and to aid in locating certain sections These headings are not intended to limit the scope of the concepts described therein under, and these concepts may have applicability in other sections throughout the entire specification Thus, the present invention is not intended to be limited to the embodiments shown herein but is to be accorded the widest scope consistent with the principles and novel features disclosed herein.

As used herein and in the appended claims, the singular forms "a", "an", and "the" include plural referents unless the context clearly indicates otherwise. Thus, for example, reference to "a compound" includes one or more of such compounds, and reference to "the method" includes reference to equivalent steps and methods known to those of ordinary skill in the art that could be modified or substituted for the methods described herein.

Unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A peptidic substrate comprising a peptide having the amino acid sequence K-L-V-G-A-D-D-V-S-L-A (SEQ ID NO: 9), a fluorophore, and a quencher, wherein the fluorophore and the quencher are bound directly to the peptide on opposite sides of the aspartic acid residues, and wherein the peptidic substrate is cleavable by a protease comprising SEQ ID NO: 4.

2. The peptidic substrate of claim 1, wherein the quencher is Dabsyl or DYQ60 and wherein the fluorophore is EDANS or DY630.

3. The peptidic substrate of claim 2, wherein the substrate comprises one of the two following combinations of quencher and fluorophore: i) Dabsyl and EDANS; or ii) DYQ660 and DY630.

4. The peptidic substrate of claim 1, wherein said peptidic substrate consists of Dabsyl-K-L-V-G-A-D-D-V-S-L-A-EDANS (Dabsyl-SEQ ID NO: 9-EDANS) or DYQ660-K-L-V-G-A-D-D-V-S-L-A-K-DY630 (DYQ660-SEQ ID NO: 10-DY630).

5. An in vitro screening method for identifying inhibitors of *Plasmodium*, comprising:
   a) incubating a peptidic substrate according to claim 1 with malarial subtilisin-like protease 1 (SUB1) comprising SEQ ID NO: 4 in the presence of a candidate compound,
   b) detecting cleavage of the peptidic substrate by the protease comprising SEQ ID NO: 4; and
   c) comparing cleavage of the peptidic substrate by the protease in the presence of the candidate compound to cleavage of the peptidic substrate by the protease in the absence of the candidate compound.

6. The in vitro screening method of claim 5, wherein an inhibition of said cleavage in the presence of the candidate compound compared to the cleavage in the absence of the candidate compound identifies said candidate compound as a potential inhibitor of *Plasmodium* life cycle.

7. The in vitro screening method of claim 6, wherein said inhibition of cleavage identifies said candidate compound as a potential inhibitor of *Plasmodium vivax, Plasmodium falciparum* and/or *Plasmodium berghei*.

8. The in vitro screening method of claim 5, wherein said screening method is a high-throughput method.

9. The in vitro screening method of claim 5, wherein the cleavage in step b) is detected by fluorescence assay.

10. The in vitro screening method of claim 9, wherein the fluorescence assay is Fluorescent Resonance Energy Transfer (FRET) assay.

11. The in vitro screening method of claim 5, further comprising:
    selecting a candidate compound capable of inhibiting cleavage of said peptidic substrate; and
    testing ex vivo said selected candidate compound on a culture of one or more species of *Plasmodium* and/or testing in vivo said selected candidate compound in at least one *Plasmodium*-infected animal.

12. An isolated polypeptide, comprising the amino acid sequence of SEQ ID NO: 4.

13. A cell expressing the isolated polypeptide of claim 12.

14. A kit for in vitro screening test comprising a peptidic substrate as defined in claim 1, and a protease comprising SEQ ID NO: 4.

* * * * *

SEQUENCE LISTING

```
<160> NUMBER OF SEQ ID NOS: 26

<210> SEQ ID NO 1
<211> LENGTH: 2050
<212> TYPE: DNA
<213> ORGANISM: Plasmodium vivax
<220> FEATURE:
<221> NAME/KEY: CDS
<222> LOCATION: (37)..(1926)

<400> SEQUENCE: 1
agaattcgcc cttggtaact cctgcacagc aacgca atg gtg ctg acg cga aga      54
                                        Met Val Leu Thr Arg Arg
                                        1               5 gca gcg ctc ctc ctg tgc ccc tgg gta atc caa ctg gta atc aag cga     102
Ala Ala Leu Leu Leu Cys Pro Trp Val Ile Gln Leu Val Ile Lys Arg
            10                  15                  20 acc ctc gca ggg gac atc ctg ccg aat gag ggc aag aag gaa aag gat     150
Thr Leu Ala Gly Asp Ile Leu Pro Asn Glu Gly Lys Lys Glu Lys Asp
        25                  30                  35 gat gtg cat aaa att ata agc gag ttg cgc ttc cta cag aag gta gaa     198
Asp Val His Lys Ile Ile Ser Glu Leu Arg Phe Leu Gln Lys Val Glu
    40                  45                  50 acc att ttg gag agc agc aac atg agc gtt tca gat gtg gag gca gat     246
```

|   |   |
|---|---|
| Thr Ile Leu Glu Ser Ser Asn Met Ser Val Ser Asp Val Glu Ala Asp<br>55                       60                       65                       70 |   |
| gcg aat gcg tat aat cct gat agg gac gcc cct aaa gag gag ctg cag<br>Ala Asn Ala Tyr Asn Pro Asp Arg Asp Ala Pro Lys Glu Glu Leu Gln<br>                   75                       80                       85 | 294 |
| aag ctc caa gac cag cag gaa acc ccc tcg aag cag cct aat aac cta<br>Lys Leu Gln Asp Gln Gln Glu Thr Pro Ser Lys Gln Pro Asn Asn Leu<br>          90                       95                      100 | 342 |
| cgg aat agc ccc caa aaa aga gca gaa aaa aaa gag tca cct ggg aaa<br>Arg Asn Ser Pro Gln Lys Arg Ala Glu Lys Lys Glu Ser Pro Gly Lys<br>             105                     110                    115 | 390 |
| aat aaa aag tcg tta cgc tta att gtg agt gag aac cac gcc acg agt<br>Asn Lys Lys Ser Leu Arg Leu Ile Val Ser Glu Asn His Ala Thr Ser<br>120                     125                     130 | 438 |
| ccc tcc ttc ttc gag gag tct ctc ctt caa gaa gac gtg gtg agc ttc<br>Pro Ser Phe Phe Glu Glu Ser Leu Leu Gln Glu Asp Val Val Ser Phe<br>135                     140                     145                    150 | 486 |
| atc cag agc aaa ggg aag cta tcc aat ctg aag aat cta aaa tcg atg<br>Ile Gln Ser Lys Gly Lys Leu Ser Asn Leu Lys Asn Leu Lys Ser Met<br>                   155                     160                    165 | 534 |
| ata atc gat ttg aac agc gac atg acg gat gag gag ttg gca gag tac<br>Ile Ile Asp Leu Asn Ser Asp Met Thr Asp Glu Glu Leu Ala Glu Tyr<br>             170                     175                    180 | 582 |
| att agc ctg ttg gag agg aag ggg gcg ttg ata gaa tct gac aag ctc<br>Ile Ser Leu Leu Glu Arg Lys Gly Ala Leu Ile Glu Ser Asp Lys Leu<br>                   185                     190                    195 | 630 |
| gtg ggg gcg gac gac gtg agc ctt gca tct gta aag gat gcg gtc agg<br>Val Gly Ala Asp Asp Val Ser Leu Ala Ser Val Lys Asp Ala Val Arg<br>200                     205                     210 | 678 |
| cgc ggg gag agt agc gtc aat tgg ggt aaa ctc cgc agc acc atg ttg<br>Arg Gly Glu Ser Ser Val Asn Trp Gly Lys Leu Arg Ser Thr Met Leu<br>215                     220                     225                    230 | 726 |
| gag gtt cca agc ggg gag tcc ccc ccc agc cac gcc gct agc agt ggc<br>Glu Val Pro Ser Gly Glu Ser Pro Pro Ser His Ala Ala Ser Ser Gly<br>                   235                     240                    245 | 774 |
| agc ccc ttc gat gac gat gat gac ctc ctg tcg gag gcg gcc ctc cac<br>Ser Pro Phe Asp Asp Asp Asp Asp Leu Leu Ser Glu Ala Ala Leu His<br>             250                     255                    260 | 822 |
| agg gag gaa gcc cac ctg gcg ggg agc aaa acc acc aag ggg tac aaa<br>Arg Glu Glu Ala His Leu Ala Gly Ser Lys Thr Thr Lys Gly Tyr Lys<br>265                     270                     275 | 870 |
| ttc aac gat gag tac agg aac ctg cag tgg ggg ttg gac ctc gcc agg<br>Phe Asn Asp Glu Tyr Arg Asn Leu Gln Trp Gly Leu Asp Leu Ala Arg<br>          280                      285                    290 | 918 |
| cta gac gaa acg cag gat ctt ata aac gca aac cga gtg agc gta acc<br>Leu Asp Glu Thr Gln Asp Leu Ile Asn Ala Asn Arg Val Ser Val Thr<br>295                     300                     305                    310 | 966 |
| aaa atc tgc gta att gac agc ggg atc gat tac aac cac ccc gac ttg<br>Lys Ile Cys Val Ile Asp Ser Gly Ile Asp Tyr Asn His Pro Asp Leu<br>             315                     320                    325 | 1014 |
| agg aac aac ata gat gtg aat gtg aaa gag ctg cac gga aga aaa gga<br>Arg Asn Asn Ile Asp Val Asn Val Lys Glu Leu His Gly Arg Lys Gly<br>                   330                     335                    340 | 1062 |
| gtg gac gat gat agc aac gga gtc gtg gac gat gtg tat gga gcc aat<br>Val Asp Asp Asp Ser Asn Gly Val Val Asp Asp Val Tyr Gly Ala Asn<br>             345                     350                    355 | 1110 |
| ttt gta aac aac agt gga gat cct atg gat gat aat tac cac gga acg<br>Phe Val Asn Asn Ser Gly Asp Pro Met Asp Asp Asn Tyr His Gly Thr<br>360                     365                     370 | 1158 |

```
cat gtc tct gga atc att tcc gcc gtt ggg aat aat ggc ata ggt ata     1206
His Val Ser Gly Ile Ile Ser Ala Val Gly Asn Asn Gly Ile Gly Ile
375                 380                 385                 390 gtg ggg gta gat ggg cac tct aag cta gtc ata tgt aag gca cta gat     1254
Val Gly Val Asp Gly His Ser Lys Leu Val Ile Cys Lys Ala Leu Asp
                395                 400                 405 caa cac aag ctg gga cga cta ggg gac atg ttc aaa tgc att gac tac     1302
Gln His Lys Leu Gly Arg Leu Gly Asp Met Phe Lys Cys Ile Asp Tyr
            410                 415                 420 tgc ata agc aga cag gca cat atg att aat ggt agc ttt tca ttt gac     1350
Cys Ile Ser Arg Gln Ala His Met Ile Asn Gly Ser Phe Ser Phe Asp
        425                 430                 435 gag tat agc aat atc ttt aat gcg tct gtg gag cac cta cga tct ctg     1398
Glu Tyr Ser Asn Ile Phe Asn Ala Ser Val Glu His Leu Arg Ser Leu
    440                 445                 450 gga att ctt ttc ttc gtc tcg gcc agc aac tgt gca cat gat aag ctc     1446
Gly Ile Leu Phe Phe Val Ser Ala Ser Asn Cys Ala His Asp Lys Leu
455                 460                 465                 470 tcc aaa ccg gac att gcc aaa tgc gac ctc gcc gtt aat cat agg tac     1494
Ser Lys Pro Asp Ile Ala Lys Cys Asp Leu Ala Val Asn His Arg Tyr
                475                 480                 485 cct ccc atc ttg tct aaa acg cac aac aat gta atc gct gtt gcg aat     1542
Pro Pro Ile Leu Ser Lys Thr His Asn Asn Val Ile Ala Val Ala Asn
            490                 495                 500 ttg aag aga gac cta gat gag agc tac tcc ctc tct gtt aac tcc ttt     1590
Leu Lys Arg Asp Leu Asp Glu Ser Tyr Ser Leu Ser Val Asn Ser Phe
        505                 510                 515 tac agt aat att tat tgc cag ttg gct gct ccg ggg act aat ata tat     1638
Tyr Ser Asn Ile Tyr Cys Gln Leu Ala Ala Pro Gly Thr Asn Ile Tyr
    520                 525                 530 tct acc acg cct atg aat aac tat cgg aag ctc aat ggc act tcc atg     1686
Ser Thr Thr Pro Met Asn Asn Tyr Arg Lys Leu Asn Gly Thr Ser Met
535                 540                 545                 550 gca tct ccg cac gtg gct gca atc gcc tcc atc gtt agg tct atc aac     1734
Ala Ser Pro His Val Ala Ala Ile Ala Ser Ile Val Arg Ser Ile Asn
                555                 560                 565 cct aat ttg act tac ctg caa att gtc gaa att ttg agg aac gcc att     1782
Pro Asn Leu Thr Tyr Leu Gln Ile Val Glu Ile Leu Arg Asn Ala Ile
            570                 575                 580 gtg aag ctc ccc tcc ctc acc gag agg gtc tcg tgg gga ggc tac gtc     1830
Val Lys Leu Pro Ser Leu Thr Glu Arg Val Ser Trp Gly Gly Tyr Val
        585                 590                 595 gac atc ctg cgc gcc gtc aac ctg gcc atc gac tcc aag gcg gcg ccc     1878
Asp Ile Leu Arg Ala Val Asn Leu Ala Ile Asp Ser Lys Ala Ala Pro
    600                 605                 610 tac atc aag tcg cac tcc tgg ttc agg tgg aag cag ggc agt agg cgg     1926
Tyr Ile Lys Ser His Ser Trp Phe Arg Trp Lys Gln Gly Ser Arg Arg
615                 620                 625                 630 taggcggtgg acggtggacg gtgggcggtg ggcggtggag cggtaaagcg gtggagcggc   1986
acgcgacagg gcaacagagc aacagagcaa cagagcggcg tcacatcaga gcgaccgcgc   2046
aaca                                                                2050
```

<210> SEQ ID NO 2
<211> LENGTH: 630
<212> TYPE: PRT
<213> ORGANISM: Plasmodium vivax

<400> SEQUENCE: 2

Met Val Leu Thr Arg Arg Ala Ala Leu Leu Leu Cys Pro Trp Val Ile

-continued

```
  1               5                  10                 15
Gln Leu Val Ile Lys Arg Thr Leu Ala Gly Asp Ile Leu Pro Asn Glu
                 20                 25                 30
Gly Lys Lys Glu Lys Asp Asp Val His Lys Ile Ile Ser Glu Leu Arg
                 35                 40                 45
Phe Leu Gln Lys Val Glu Thr Ile Leu Glu Ser Ser Asn Met Ser Val
 50                                 55                 60
Ser Asp Val Glu Ala Asp Ala Asn Ala Tyr Asn Pro Asp Arg Asp Ala
 65                 70                 75                 80
Pro Lys Glu Glu Leu Gln Lys Leu Gln Asp Gln Gln Glu Thr Pro Ser
                 85                 90                 95
Lys Gln Pro Asn Asn Leu Arg Asn Ser Pro Gln Lys Arg Ala Glu Lys
                100                105                110
Lys Glu Ser Pro Gly Lys Asn Lys Lys Ser Leu Arg Leu Ile Val Ser
                115                120                125
Glu Asn His Ala Thr Ser Pro Ser Phe Phe Glu Glu Ser Leu Leu Gln
                130                135                140
Glu Asp Val Val Ser Phe Ile Gln Ser Lys Gly Lys Leu Ser Asn Leu
145                150                155                160
Lys Asn Leu Lys Ser Met Ile Ile Asp Leu Asn Ser Asp Met Thr Asp
                165                170                175
Glu Glu Leu Ala Glu Tyr Ile Ser Leu Leu Glu Arg Lys Gly Ala Leu
                180                185                190
Ile Glu Ser Asp Lys Leu Val Gly Ala Asp Val Ser Leu Ala Ser
                195                200                205
Val Lys Asp Ala Val Arg Arg Gly Glu Ser Ser Val Asn Trp Gly Lys
210                215                220
Leu Arg Ser Thr Met Leu Glu Val Pro Ser Gly Glu Ser Pro Pro Ser
225                230                235                240
His Ala Ala Ser Ser Gly Ser Pro Phe Asp Asp Asp Asp Leu Leu
                245                250                255
Ser Glu Ala Ala Leu His Arg Glu Glu Ala His Leu Ala Gly Ser Lys
                260                265                270
Thr Thr Lys Gly Tyr Lys Phe Asn Asp Glu Tyr Arg Asn Leu Gln Trp
                275                280                285
Gly Leu Asp Leu Ala Arg Leu Asp Glu Thr Gln Asp Leu Ile Asn Ala
                290                295                300
Asn Arg Val Ser Val Thr Lys Ile Cys Val Ile Asp Ser Gly Ile Asp
305                310                315                320
Tyr Asn His Pro Asp Leu Arg Asn Asn Ile Asp Val Asn Val Lys Glu
                325                330                335
Leu His Gly Arg Lys Gly Val Asp Asp Ser Asn Gly Val Val Asp
                340                345                350
Asp Val Tyr Gly Ala Asn Phe Val Asn Ser Gly Asp Pro Met Asp
                355                360                365
Asp Asn Tyr His Gly Thr His Val Ser Gly Ile Ile Ser Ala Val Gly
                370                375                380
Asn Asn Gly Ile Gly Ile Val Gly Val Asp Gly His Ser Lys Leu Val
385                390                395                400
Ile Cys Lys Ala Leu Asp Gln His Lys Leu Gly Arg Leu Gly Asp Met
                405                410                415
Phe Lys Cys Ile Asp Tyr Cys Ile Ser Arg Gln Ala His Met Ile Asn
                420                425                430
```

```
Gly Ser Phe Ser Phe Asp Glu Tyr Ser Asn Ile Phe Asn Ala Ser Val
            435                 440                 445

Glu His Leu Arg Ser Leu Gly Ile Leu Phe Phe Val Ser Ala Ser Asn
            450                 455                 460

Cys Ala His Asp Lys Leu Ser Lys Pro Asp Ile Ala Lys Cys Asp Leu
465                 470                 475                 480

Ala Val Asn His Arg Tyr Pro Pro Ile Leu Ser Lys Thr His Asn Asn
            485                 490                 495

Val Ile Ala Val Ala Asn Leu Lys Arg Asp Leu Asp Glu Ser Tyr Ser
            500                 505                 510

Leu Ser Val Asn Ser Phe Tyr Ser Asn Ile Tyr Cys Gln Leu Ala Ala
            515                 520                 525

Pro Gly Thr Asn Ile Tyr Ser Thr Thr Pro Met Asn Asn Tyr Arg Lys
            530                 535                 540

Leu Asn Gly Thr Ser Met Ala Ser Pro His Val Ala Ala Ile Ala Ser
545                 550                 555                 560

Ile Val Arg Ser Ile Asn Pro Asn Leu Thr Tyr Leu Gln Ile Val Glu
            565                 570                 575

Ile Leu Arg Asn Ala Ile Val Lys Leu Pro Ser Leu Thr Glu Arg Val
            580                 585                 590

Ser Trp Gly Gly Tyr Val Asp Ile Leu Arg Ala Val Asn Leu Ala Ile
            595                 600                 605

Asp Ser Lys Ala Ala Pro Tyr Ile Lys Ser His Ser Trp Phe Arg Trp
610                 615                 620

Lys Gln Gly Ser Arg Arg
625                 630

<210> SEQ ID NO 3
<211> LENGTH: 652
<212> TYPE: PRT
<213> ORGANISM: Plasmodium vivax

<400> SEQUENCE: 3

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro Gly Asp Ile Leu Pro Asn Glu
            35                  40                  45

Gly Lys Lys Glu Lys Asp Asp Val His Lys Ile Ile Ser Glu Leu Arg
    50                  55                  60

Phe Leu Gln Lys Val Glu Thr Ile Leu Glu Ser Ser Asn Met Ser Val
65              70                  75                  80

Ser Asp Val Glu Ala Asp Ala Asn Ala Tyr Asn Pro Asp Arg Asp Ala
            85                  90                  95

Pro Lys Glu Glu Leu Gln Lys Leu Gln Asp Gln Glu Thr Pro Ser
            100                 105                 110

Lys Gln Pro Asn Asn Leu Arg Asn Ser Pro Gln Lys Arg Ala Glu Lys
            115                 120                 125

Lys Glu Ser Pro Gly Lys Asn Lys Lys Ser Leu Arg Leu Ile Val Ser
    130                 135                 140

Glu Asn His Ala Thr Ser Pro Ser Phe Phe Glu Glu Ser Leu Leu Gln
145                 150                 155                 160

Glu Asp Val Val Ser Phe Ile Gln Ser Lys Gly Lys Leu Ser Asn Leu
```

-continued

```
                165                 170                 175
Lys Asn Leu Lys Ser Met Ile Ile Asp Leu Asn Ser Asp Met Thr Asp
            180                 185                 190

Glu Glu Leu Ala Glu Tyr Ile Ser Leu Leu Glu Arg Lys Gly Ala Leu
            195                 200                 205

Ile Glu Ser Asp Lys Leu Val Gly Ala Asp Val Ser Leu Ala Ser
210                 215                 220

Val Lys Asp Ala Val Arg Arg Gly Glu Ser Ser Val Asn Trp Gly Lys
225                 230                 235                 240

Leu Arg Ser Thr Met Leu Glu Val Pro Ser Gly Glu Ser Pro Pro Ser
                245                 250                 255

His Ala Ala Ser Ser Gly Ser Pro Phe Asp Asp Asp Asp Leu Leu
            260                 265                 270

Ser Glu Ala Ala Leu His Arg Glu Glu Ala His Leu Ala Gly Ser Lys
            275                 280                 285

Thr Thr Lys Gly Tyr Lys Phe Asn Asp Glu Tyr Arg Asn Leu Gln Trp
            290                 295                 300

Gly Leu Asp Leu Ala Arg Leu Asp Glu Thr Gln Asp Leu Ile Asn Ala
305                 310                 315                 320

Asn Arg Val Ser Val Thr Lys Ile Cys Val Ile Asp Ser Gly Ile Asp
                325                 330                 335

Tyr Asn His Pro Asp Leu Arg Asn Asn Ile Asp Val Asn Val Lys Glu
            340                 345                 350

Leu His Gly Arg Lys Gly Val Asp Asp Ser Asn Gly Val Val Asp
            355                 360                 365

Asp Val Tyr Gly Ala Asn Phe Val Asn Asn Ser Gly Asp Pro Met Asp
            370                 375                 380

Asp Asn Tyr His Gly Thr His Val Ser Gly Ile Ser Ala Val Gly
385                 390                 395                 400

Asn Asn Gly Ile Gly Ile Val Gly Val Asp Gly His Ser Lys Leu Val
                405                 410                 415

Ile Cys Lys Ala Leu Asp Gln His Lys Leu Gly Arg Leu Gly Asp Met
            420                 425                 430

Phe Lys Cys Ile Asp Tyr Cys Ile Ser Arg Gln Ala His Met Ile Asn
            435                 440                 445

Gly Ser Phe Ser Phe Asp Glu Tyr Ser Asn Ile Phe Asn Ala Ser Val
            450                 455                 460

Glu His Leu Arg Ser Leu Gly Ile Leu Phe Phe Val Ser Ala Ser Asn
465                 470                 475                 480

Cys Ala His Asp Lys Leu Ser Lys Pro Asp Ile Ala Lys Cys Asp Leu
                485                 490                 495

Ala Val Asn His Arg Tyr Pro Pro Ile Leu Ser Lys Thr His Asn Asn
            500                 505                 510

Val Ile Ala Val Ala Asn Leu Lys Arg Asp Leu Asp Glu Ser Tyr Ser
            515                 520                 525

Leu Ser Val Asn Ser Phe Tyr Ser Asn Ile Tyr Cys Gln Leu Ala Ala
            530                 535                 540

Pro Gly Thr Asn Ile Tyr Ser Thr Thr Pro Met Asn Asn Tyr Arg Lys
545                 550                 555                 560

Leu Asn Gly Thr Ser Met Ala Ser Pro His Val Ala Ala Ile Ala Ser
                565                 570                 575

Ile Val Arg Ser Ile Asn Pro Asn Leu Thr Tyr Leu Gln Ile Val Glu
            580                 585                 590
```

```
Ile Leu Arg Asn Ala Ile Val Lys Leu Pro Ser Leu Thr Glu Arg Val
        595                 600                 605

Ser Trp Gly Gly Tyr Val Asp Ile Leu Arg Ala Val Asn Leu Ala Ile
610                 615                 620

Asp Ser Lys Ala Ala Pro Tyr Ile Lys Ser His Ser Trp Phe Arg Trp
625                 630                 635                 640

Lys Gln Gly Ser Arg Arg His His His His His
                645                 650

<210> SEQ ID NO 4
<211> LENGTH: 434
<212> TYPE: PRT
<213> ORGANISM: Plasmodium vivax

<400> SEQUENCE: 4

Asp Val Ser Leu Ala Ser Val Lys Asp Ala Val Arg Arg Gly Glu Ser
1               5                   10                  15

Ser Val Asn Trp Gly Lys Leu Arg Ser Thr Met Leu Glu Val Pro Ser
                20                  25                  30

Gly Glu Ser Pro Pro Ser His Ala Ala Ser Ser Gly Ser Pro Phe Asp
            35                  40                  45

Asp Asp Asp Asp Leu Leu Ser Glu Ala Ala Leu His Arg Glu Glu Ala
50                  55                  60

His Leu Ala Gly Ser Lys Thr Thr Lys Gly Tyr Lys Phe Asn Asp Glu
65                  70                  75                  80

Tyr Arg Asn Leu Gln Trp Gly Leu Asp Leu Ala Arg Leu Asp Glu Thr
                85                  90                  95

Gln Asp Leu Ile Asn Ala Asn Arg Val Ser Val Thr Lys Ile Cys Val
            100                 105                 110

Ile Asp Ser Gly Ile Asp Tyr Asn His Pro Asp Leu Arg Asn Asn Ile
        115                 120                 125

Asp Val Asn Val Lys Glu Leu His Gly Arg Lys Gly Val Asp Asp Asp
    130                 135                 140

Ser Asn Gly Val Val Asp Asp Val Tyr Gly Ala Asn Phe Val Asn Asn
145                 150                 155                 160

Ser Gly Asp Pro Met Asp Asp Asn Tyr His Gly Thr His Val Ser Gly
                165                 170                 175

Ile Ile Ser Ala Val Gly Asn Asn Ile Gly Ile Val Gly Val Asp
            180                 185                 190

Gly His Ser Lys Leu Val Ile Cys Lys Ala Leu Asp Gln His Lys Leu
        195                 200                 205

Gly Arg Leu Gly Asp Met Phe Lys Cys Ile Asp Tyr Cys Ile Ser Arg
    210                 215                 220

Gln Ala His Met Ile Asn Gly Ser Phe Ser Phe Asp Glu Tyr Ser Asn
225                 230                 235                 240

Ile Phe Asn Ala Ser Val Glu His Leu Arg Ser Leu Gly Ile Leu Phe
                245                 250                 255

Phe Val Ser Ala Ser Asn Cys Ala His Asp Lys Leu Ser Lys Pro Asp
            260                 265                 270

Ile Ala Lys Cys Asp Leu Ala Val Asn His Arg Tyr Pro Pro Ile Leu
        275                 280                 285

Ser Lys Thr His Asn Asn Val Ile Ala Val Ala Asn Leu Lys Arg Asp
    290                 295                 300

Leu Asp Glu Ser Tyr Ser Leu Ser Val Asn Ser Phe Tyr Ser Asn Ile
```

-continued

```
            305                 310                 315                 320
Tyr Cys Gln Leu Ala Ala Pro Gly Thr Asn Ile Tyr Ser Thr Thr Pro
                325                 330                 335

Met Asn Asn Tyr Arg Lys Leu Asn Gly Thr Ser Met Ala Ser Pro His
            340                 345                 350

Val Ala Ala Ile Ala Ser Ile Val Arg Ser Ile Asn Pro Asn Leu Thr
        355                 360                 365

Tyr Leu Gln Ile Val Glu Ile Leu Arg Asn Ala Ile Val Lys Leu Pro
    370                 375                 380

Ser Leu Thr Glu Arg Val Ser Trp Gly Gly Tyr Val Asp Ile Leu Arg
385                 390                 395                 400

Ala Val Asn Leu Ala Ile Asp Ser Lys Ala Ala Pro Tyr Ile Lys Ser
                405                 410                 415

His Ser Trp Phe Arg Trp Lys Gln Gly Ser Arg Arg His His His
            420                 425                 430

His His
```

```
<210> SEQ ID NO 5
<211> LENGTH: 2253
<212> TYPE: DNA
<213> ORGANISM: Plasmodium falciparum
<220> FEATURE:
<221> NAME/KEY: CDS
<222> LOCATION: (85)..(2217)

<400> SEQUENCE: 5
ttactgtttt cgtacagttt tgtaataaaa aaacctataa atattccgga ttattcatac      60
cgtcccacca tcgggcgcgg atct atg cta cta gta aat cag tca cac caa       111
                          Met Leu Leu Val Asn Gln Ser His Gln
                            1               5 ggc ttc aat aag gaa cac aca agc aag atg gta agc gct att gtt tta      159
Gly Phe Asn Lys Glu His Thr Ser Lys Met Val Ser Ala Ile Val Leu
 10                  15                  20                  25 tat gtg ctt ttg gcg gcg gcg gcg cat tct gcc ttt gcg gcg gat ctt      207
Tyr Val Leu Leu Ala Ala Ala Ala His Ser Ala Phe Ala Ala Asp Leu
                 30                  35                  40 gga tct aag gag gtg aga tcc gaa gag aac ggc aaa ata caa gac gat      255
Gly Ser Lys Glu Val Arg Ser Glu Glu Asn Gly Lys Ile Gln Asp Asp
             45                  50                  55 gcg aag aaa ata gtg agc gag ctc cgg ttt ctt gag aag gtt gaa gac      303
Ala Lys Lys Ile Val Ser Glu Leu Arg Phe Leu Glu Lys Val Glu Asp
         60                  65                  70 gtc att gag aaa agc aat ata gga ggc aac gag gtg gat gca gac gag      351
Val Ile Glu Lys Ser Asn Ile Gly Gly Asn Glu Val Asp Ala Asp Glu
     75                  80                  85 aat agt ttc aac cct gat aca gaa gtg ccc atc gag gag ata gaa gag      399
Asn Ser Phe Asn Pro Asp Thr Glu Val Pro Ile Glu Glu Ile Glu Glu
 90                  95                 100                 105 atc aag atg cga gag ctg aag gac gtc aaa gag gaa aag aat aaa aac      447
Ile Lys Met Arg Glu Leu Lys Asp Val Lys Glu Glu Lys Asn Lys Asn
                110                 115                 120 gat aat cac aac aat aat aat aac aat att agt agt tcc agt tct tcc      495
Asp Asn His Asn Asn Asn Asn Asn Ile Ser Ser Ser Ser Ser Ser
            125                 130                 135 agt agc aac acg ttt gga gag gaa aaa gaa gag gtt agt aag aaa aaa      543
Ser Ser Asn Thr Phe Gly Glu Glu Lys Glu Glu Val Ser Lys Lys Lys
        140                 145                 150 aag aaa ctg aga ctg atc gtg tca gag aat cat gca act acc cct agc      591
```

-continued

```
                Lys Lys Leu Arg Leu Ile Val Ser Glu Asn His Ala Thr Thr Pro Ser
                    155                 160                 165 ttc ttc cag gaa tcc ctg ctc gaa cca gac gtc ttg agc ttt ctg gaa          639
Phe Phe Gln Glu Ser Leu Leu Glu Pro Asp Val Leu Ser Phe Leu Glu
170                 175                 180                 185 tca aag ggc aac ctg agc aat ctg aag aac atc aat tcc atg att att          687
Ser Lys Gly Asn Leu Ser Asn Leu Lys Asn Ile Asn Ser Met Ile Ile
                190                 195                 200 gaa ctc aag gaa gac acc acc gac gat gaa ctc atc tct tat atc aag          735
Glu Leu Lys Glu Asp Thr Thr Asp Asp Glu Leu Ile Ser Tyr Ile Lys
                    205                 210                 215 att ttg gag gag aaa gga gct ctc atc gag tcc gat aag ctg gtt agt          783
Ile Leu Glu Glu Lys Gly Ala Leu Ile Glu Ser Asp Lys Leu Val Ser
                220                 225                 230 gca gac aac atc gat att tcc ggt atc aag gat gcc ata cgc agg gga          831
Ala Asp Asn Ile Asp Ile Ser Gly Ile Lys Asp Ala Ile Arg Arg Gly
        235                 240                 245 gag gaa aac atc gat gtg aat gat tac aag agc atg ctt gaa gtg gaa          879
Glu Glu Asn Ile Asp Val Asn Asp Tyr Lys Ser Met Leu Glu Val Glu
250                 255                 260                 265 aat gat gcc gaa gac tat gat aaa atg ttt gga atg ttc aac gag agc          927
Asn Asp Ala Glu Asp Tyr Asp Lys Met Phe Gly Met Phe Asn Glu Ser
                    270                 275                 280 cat gcc gcc aca agt aag cgg aaa aga cac tcc aca aac gag agg ggc          975
His Ala Ala Thr Ser Lys Arg Lys Arg His Ser Thr Asn Glu Arg Gly
                285                 290                 295 tac gac act ttt agc tca cct agt tat aag acc tac tcc aag tct gac         1023
Tyr Asp Thr Phe Ser Ser Pro Ser Tyr Lys Thr Tyr Ser Lys Ser Asp
                    300                 305                 310 tac ctg tac gac gac gac aac aat aac aat aac tac tac tac agc cat         1071
Tyr Leu Tyr Asp Asp Asp Asn Asn Asn Asn Asn Tyr Tyr Tyr Ser His
315                 320                 325 tcc agc aat gga cat aat tcc tca agt cga aat agc tct agc tca cgc         1119
Ser Ser Asn Gly His Asn Ser Ser Ser Arg Asn Ser Ser Ser Ser Arg
330                 335                 340                 345 agt agg cca ggc aaa tac cac ttt aac gac gag ttc aga aac ctg caa         1167
Ser Arg Pro Gly Lys Tyr His Phe Asn Asp Glu Phe Arg Asn Leu Gln
                    350                 355                 360 tgg gga ctg gac ttg tca cga ctc gac gag act cag gaa ttg atc aac         1215
Trp Gly Leu Asp Leu Ser Arg Leu Asp Glu Thr Gln Glu Leu Ile Asn
                365                 370                 375 gag cac cag gtg atg tcc act cgc att tgc gtc ata gac tcc gga att         1263
Glu His Gln Val Met Ser Thr Arg Ile Cys Val Ile Asp Ser Gly Ile
        380                 385                 390 gat tat aac cac cct gac ctg aag gac aat atc gag ctt aat ctg aag         1311
Asp Tyr Asn His Pro Asp Leu Lys Asp Asn Ile Glu Leu Asn Leu Lys
395                 400                 405 gaa ctc cac ggg agg aag gga ttt gat gat gat aat aat ggc atc gtg         1359
Glu Leu His Gly Arg Lys Gly Phe Asp Asp Asp Asn Asn Gly Ile Val
410                 415                 420                 425 gac gac atc tac ggt gcc aat ttc gtg aat aac agc ggg aac ccg atg         1407
Asp Asp Ile Tyr Gly Ala Asn Phe Val Asn Asn Ser Gly Asn Pro Met
                430                 435                 440 gac gat aac tat cat ggt acg cac gtt tct ggc atc atc agc gcc atc         1455
Asp Asp Asn Tyr His Gly Thr His Val Ser Gly Ile Ile Ser Ala Ile
                    445                 450                 455 ggc aat aac aac att gga gta gtt ggt gta gat gtc aac tca aaa ttg         1503
Gly Asn Asn Asn Ile Gly Val Val Gly Val Asp Val Asn Ser Lys Leu
                460                 465                 470
```

-continued

| | |
|---|---|
| atc atc tgt aag gcc ctt gac gaa cac aaa ctt gga cgg ctg ggc gat<br>Ile Ile Cys Lys Ala Leu Asp Glu His Lys Leu Gly Arg Leu Gly Asp<br>475                    480                    485 | 1551 |
| atg ttc aag tgc ctt gac tat tgc ata tct agg aat gcc cac atg ata<br>Met Phe Lys Cys Leu Asp Tyr Cys Ile Ser Arg Asn Ala His Met Ile<br>490                    495                    500                    505 | 1599 |
| aac ggc tca ttc tca ttc gac gag tac tct ggg atc ttt aac tct tca<br>Asn Gly Ser Phe Ser Phe Asp Glu Tyr Ser Gly Ile Phe Asn Ser Ser<br>510                    515                    520 | 1647 |
| gtg gag tat ctt cag cgc aaa gga ata ctc ttc ttt gtc agc gca agc<br>Val Glu Tyr Leu Gln Arg Lys Gly Ile Leu Phe Phe Val Ser Ala Ser<br>525                    530                    535 | 1695 |
| aat tgt tca cac ccc aag tct tct aca cct gat att cgg aag tgt gac<br>Asn Cys Ser His Pro Lys Ser Ser Thr Pro Asp Ile Arg Lys Cys Asp<br>540                    545                    550 | 1743 |
| ctg agc att aac gct aag tac cca ccc atc ctg tca act gtg tac gat<br>Leu Ser Ile Asn Ala Lys Tyr Pro Pro Ile Leu Ser Thr Val Tyr Asp<br>555                    560                    565 | 1791 |
| aat gtc atc agc gtg gct aat ctg aaa aag aac gac aac aac aat cac<br>Asn Val Ile Ser Val Ala Asn Leu Lys Lys Asn Asp Asn Asn Asn His<br>570                    575                    580                    585 | 1839 |
| tat agt ctt tct atc aac tct ttc tat tct aac aaa tat tgc cag ttg<br>Tyr Ser Leu Ser Ile Asn Ser Phe Tyr Ser Asn Lys Tyr Cys Gln Leu<br>590                    595                    600 | 1887 |
| gcg gct cca ggc acc aat atc tat agc aca gca ccc cat aac tca tat<br>Ala Ala Pro Gly Thr Asn Ile Tyr Ser Thr Ala Pro His Asn Ser Tyr<br>605                    610                    615 | 1935 |
| aga aaa ctc aac ggg acc tct atg gct gca ccc cac gta gcc gct att<br>Arg Lys Leu Asn Gly Thr Ser Met Ala Ala Pro His Val Ala Ala Ile<br>620                    625                    630 | 1983 |
| gcc tcc ctg att ttc agc att aac cca gat ttg tcc tac aaa aag gtc<br>Ala Ser Leu Ile Phe Ser Ile Asn Pro Asp Leu Ser Tyr Lys Lys Val<br>635                    640                    645 | 2031 |
| att cag att ctg aag gac tcc ata gtt tac ttg ccc tcc ttg aag aac<br>Ile Gln Ile Leu Lys Asp Ser Ile Val Tyr Leu Pro Ser Leu Lys Asn<br>650                    655                    660                    665 | 2079 |
| atg gtg gca tgg gcc ggt tac gct gat att aat aag gcc gtg aac ctt<br>Met Val Ala Trp Ala Gly Tyr Ala Asp Ile Asn Lys Ala Val Asn Leu<br>670                    675                    680 | 2127 |
| gct atc aaa tcc aag aaa acc tac att aat tca aat att agc aac aaa<br>Ala Ile Lys Ser Lys Lys Thr Tyr Ile Asn Ser Asn Ile Ser Asn Lys<br>685                    690                    695 | 2175 |
| tgg aag aaa aaa tct cgg tat ctg cat cac cat cat cac cac<br>Trp Lys Lys Lys Ser Arg Tyr Leu His His His His His His<br>700                    705                    710 | 2217 |
| tgaagatccc gggccatggg aatccggagc ggccgc | 2253 |

<210> SEQ ID NO 6
<211> LENGTH: 711
<212> TYPE: PRT
<213> ORGANISM: Plasmodium falciparum

<400> SEQUENCE: 6

Met Leu Leu Val Asn Gln Ser His Gln Gly Phe Asn Lys Glu His Thr
1                  5                      10                    15

Ser Lys Met Val Ser Ala Ile Val Leu Tyr Val Leu Leu Ala Ala Ala
                  20                    25                    30

Ala His Ser Ala Phe Ala Ala Asp Leu Gly Ser Lys Glu Val Arg Ser
        35                    40                    45

Glu Glu Asn Gly Lys Ile Gln Asp Asp Ala Lys Lys Ile Val Ser Glu
    50                  55                  60

Leu Arg Phe Leu Glu Lys Val Glu Asp Val Ile Glu Lys Ser Asn Ile
65                  70                  75                  80

Gly Gly Asn Glu Val Asp Ala Asp Glu Asn Ser Phe Asn Pro Asp Thr
                85                  90                  95

Glu Val Pro Ile Glu Glu Ile Glu Glu Ile Lys Met Arg Glu Leu Lys
            100                 105                 110

Asp Val Lys Glu Glu Lys Asn Lys Asn Asp Asn His Asn Asn Asn Asn
            115                 120                 125

Asn Asn Ile Ser Ser Ser Ser Ser Ser Ser Asn Thr Phe Gly Glu
    130                 135                 140

Glu Lys Glu Glu Val Ser Lys Lys Lys Lys Leu Arg Leu Ile Val
145                 150                 155                 160

Ser Glu Asn His Ala Thr Thr Pro Ser Phe Phe Gln Glu Ser Leu Leu
                165                 170                 175

Glu Pro Asp Val Leu Ser Phe Leu Glu Ser Lys Gly Asn Leu Ser Asn
            180                 185                 190

Leu Lys Asn Ile Asn Ser Met Ile Ile Glu Leu Lys Glu Asp Thr Thr
    195                 200                 205

Asp Asp Glu Leu Ile Ser Tyr Ile Lys Ile Leu Glu Glu Lys Gly Ala
    210                 215                 220

Leu Ile Glu Ser Asp Lys Leu Val Ser Ala Asp Asn Ile Asp Ile Ser
225                 230                 235                 240

Gly Ile Lys Asp Ala Ile Arg Arg Gly Glu Glu Asn Ile Asp Val Asn
                245                 250                 255

Asp Tyr Lys Ser Met Leu Glu Val Glu Asn Asp Ala Glu Asp Tyr Asp
            260                 265                 270

Lys Met Phe Gly Met Phe Asn Glu Ser His Ala Ala Thr Ser Lys Arg
    275                 280                 285

Lys Arg His Ser Thr Asn Glu Arg Gly Tyr Asp Thr Phe Ser Ser Pro
    290                 295                 300

Ser Tyr Lys Thr Tyr Ser Lys Ser Asp Tyr Leu Tyr Asp Asp Asn
305                 310                 315                 320

Asn Asn Asn Asn Tyr Tyr Tyr Ser His Ser Ser Asn Gly His Asn Ser
                325                 330                 335

Ser Ser Arg Asn Ser Ser Ser Arg Ser Arg Pro Gly Lys Tyr His
    340                 345                 350

Phe Asn Asp Glu Phe Arg Asn Leu Gln Trp Gly Leu Asp Leu Ser Arg
    355                 360                 365

Leu Asp Glu Thr Gln Glu Leu Ile Asn Glu His Gln Val Met Ser Thr
    370                 375                 380

Arg Ile Cys Val Ile Asp Ser Gly Ile Asp Tyr Asn His Pro Asp Leu
385                 390                 395                 400

Lys Asp Asn Ile Glu Leu Asn Leu Lys Glu Leu His Gly Arg Lys Gly
                405                 410                 415

Phe Asp Asp Asp Asn Asn Gly Ile Val Asp Ile Tyr Gly Ala Asn
            420                 425                 430

Phe Val Asn Asn Ser Gly Asn Pro Met Asp Asp Asn Tyr His Gly Thr
                435                 440                 445

His Val Ser Gly Ile Ile Ser Ala Ile Gly Asn Asn Ile Gly Val
    450                 455                 460

Val Gly Val Asp Val Asn Ser Lys Leu Ile Ile Cys Lys Ala Leu Asp

```
                   465                 470                 475                 480
        Glu His Lys Leu Gly Arg Leu Gly Asp Met Phe Lys Cys Leu Asp Tyr
                            485                 490                 495

Cys Ile Ser Arg Asn Ala His Met Ile Asn Gly Ser Phe Ser Phe Asp
                        500                 505                 510

Glu Tyr Ser Gly Ile Phe Asn Ser Ser Val Glu Tyr Leu Gln Arg Lys
                    515                 520                 525

Gly Ile Leu Phe Phe Val Ser Ala Ser Asn Cys Ser His Pro Lys Ser
                530                 535                 540

Ser Thr Pro Asp Ile Arg Lys Cys Asp Leu Ser Ile Asn Ala Lys Tyr
        545                 550                 555                 560

Pro Pro Ile Leu Ser Thr Val Tyr Asp Asn Val Ile Ser Val Ala Asn
                            565                 570                 575

Leu Lys Lys Asn Asp Asn Asn His Tyr Ser Leu Ser Ile Asn Ser
                        580                 585                 590

Phe Tyr Ser Asn Lys Tyr Cys Gln Leu Ala Ala Pro Gly Thr Asn Ile
                    595                 600                 605

Tyr Ser Thr Ala Pro His Asn Ser Tyr Arg Lys Leu Asn Gly Thr Ser
                610                 615                 620

Met Ala Ala Pro His Val Ala Ile Ala Ser Leu Ile Phe Ser Ile
        625                 630                 635                 640

Asn Pro Asp Leu Ser Tyr Lys Lys Val Ile Gln Ile Leu Lys Asp Ser
                            645                 650                 655

Ile Val Tyr Leu Pro Ser Leu Lys Asn Met Val Ala Trp Ala Gly Tyr
                        660                 665                 670

Ala Asp Ile Asn Lys Ala Val Asn Leu Ala Ile Lys Ser Lys Lys Thr
                    675                 680                 685

Tyr Ile Asn Ser Asn Ile Ser Asn Lys Trp Lys Lys Ser Arg Tyr
                690                 695                 700

Leu His His His His His His
        705                 710

<210> SEQ ID NO 7
<211> LENGTH: 1878
<212> TYPE: DNA
<213> ORGANISM: Plasmodium berghei
<220> FEATURE:
<221> NAME/KEY: CDS
<222> LOCATION: (1)..(1869)

<400> SEQUENCE: 7 atg cta cta gta aat cag tca cac caa ggc ttc aat aag gaa cac aca        48
Met Leu Leu Val Asn Gln Ser His Gln Gly Phe Asn Lys Glu His Thr
1               5                   10                  15 agc aag atg gta agc gct att gtt tta tat gtg ctt ttg gcg gcg gcg        96
Ser Lys Met Val Ser Ala Ile Val Leu Tyr Val Leu Leu Ala Ala Ala
                20                  25                  30 gcg cat tct gcc ttt gcg gcg gat ccg cac aac gac ctg atg aac aag      144
Ala His Ser Ala Phe Ala Ala Asp Pro His Asn Asp Leu Met Asn Lys
            35                  40                  45 gag aag gac gtg cag aag atc atc gag gac ctc agg ttc ctg gag aag      192
Glu Lys Asp Val Gln Lys Ile Ile Glu Asp Leu Arg Phe Leu Glu Lys
        50                  55                  60 gtg gac gct atc ctg gag aac tcc aac atg act atc gac gac gtg aag      240
Val Asp Ala Ile Leu Glu Asn Ser Asn Met Thr Ile Asp Asp Val Lys
65                  70                  75                  80 gcc gac gct gac gct tac aac cct gac gag gac gcc cct aag gag gag      288
```

|   |   |   |   |   |   |   |   |   |   |   |   |   |   |   |   |   |
|---|---|---|---|---|---|---|---|---|---|---|---|---|---|---|---|---|
| Ala | Asp | Ala | Asp | Ala | Tyr | Asn | Pro | Asp | Glu | Asp | Ala | Pro | Lys | Glu | Glu | |
|   |   |   |   | 85 |   |   |   | 90 |   |   |   | 95 |   |   | | |

```
ctg aac aag atc gag atg gag aag aag aag gct gag gag gag gct aag      336
Leu Asn Lys Ile Glu Met Glu Lys Lys Lys Ala Glu Glu Glu Ala Lys
            100                 105                 110 aac tct aag aag aag atc ctg gag agg tac ctc ctg gac gag aag aag      384
Asn Ser Lys Lys Lys Ile Leu Glu Arg Tyr Leu Leu Asp Glu Lys Lys
            115                 120                 125 aag aag tcc ctg agg ctg atc gtg tcc gag aac cac gct act tct cct      432
Lys Lys Ser Leu Arg Leu Ile Val Ser Glu Asn His Ala Thr Ser Pro
130                 135                 140 tcc ttc ttc gag gag agc ctg atc cag gag gac ttc atg tcc ttc atc      480
Ser Phe Phe Glu Glu Ser Leu Ile Gln Glu Asp Phe Met Ser Phe Ile
145                 150                 155                 160 cag tcc aag ggc gag atc gtg aac ctg aag aac ctg aag agc atg atc      528
Gln Ser Lys Gly Glu Ile Val Asn Leu Lys Asn Leu Lys Ser Met Ile
            165                 170                 175 atc gag ctc aac agc gac atg acc gac aag gag ctc gag gcc tac atc      576
Ile Glu Leu Asn Ser Asp Met Thr Asp Lys Glu Leu Glu Ala Tyr Ile
            180                 185                 190 act ctg ctg aag aag aag ggt gct cac gtc gag tct gac gag ctg gtg      624
Thr Leu Leu Lys Lys Lys Gly Ala His Val Glu Ser Asp Glu Leu Val
            195                 200                 205 gga gct gac tcc atc tac gtc gac atc atc aag gac gct gtg aag cgt      672
Gly Ala Asp Ser Ile Tyr Val Asp Ile Ile Lys Asp Ala Val Lys Arg
210                 215                 220 ggc gac acc tcc atc aac ttc aag aag atg cag tcc aac atg ctg gag      720
Gly Asp Thr Ser Ile Asn Phe Lys Lys Met Gln Ser Asn Met Leu Glu
225                 230                 235                 240 gtc gag aac aag acc tac gag aag ctc aac aac aac ctc aag aag agc      768
Val Glu Asn Lys Thr Tyr Glu Lys Leu Asn Asn Asn Leu Lys Lys Ser
            245                 250                 255 aag aac agc tac aag aag agc ttc ttc aac gac gag tac cgc aac ctc      816
Lys Asn Ser Tyr Lys Lys Ser Phe Phe Asn Asp Glu Tyr Arg Asn Leu
            260                 265                 270 cag tgg gga ctg gac ctg gcc cgc ctg gac gac gct cag gag atg atc      864
Gln Trp Gly Leu Asp Leu Ala Arg Leu Asp Asp Ala Gln Glu Met Ile
            275                 280                 285 acc acc aac agc gtg gag act acc aag atc tgc gtg atc gac tcc gga      912
Thr Thr Asn Ser Val Glu Thr Thr Lys Ile Cys Val Ile Asp Ser Gly
            290                 295                 300 atc gac tac aac cac ccc gac ctg aag ggc aac atc tac gtg aac ctg      960
Ile Asp Tyr Asn His Pro Asp Leu Lys Gly Asn Ile Tyr Val Asn Leu
305                 310                 315                 320 aac gag ctc aac ggc aag gag ggt atc gac gac gac aac aac ggc atc     1008
Asn Glu Leu Asn Gly Lys Glu Gly Ile Asp Asp Asp Asn Asn Gly Ile
            325                 330                 335 atc gac gac atc tac gga gtg aac tac gtg aac aac acc ggt gac cct     1056
Ile Asp Asp Ile Tyr Gly Val Asn Tyr Val Asn Asn Thr Gly Asp Pro
            340                 345                 350 tgg gac gac cac aac cac ggt tct cac gtg agc gga atc atc tcc gct     1104
Trp Asp Asp His Asn His Gly Ser His Val Ser Gly Ile Ile Ser Ala
            355                 360                 365 atc ggt aac aac tcc atc ggt gtg gtc ggt gtc aac ccc tcc tct aag     1152
Ile Gly Asn Asn Ser Ile Gly Val Val Gly Val Asn Pro Ser Ser Lys
370                 375                 380 ctc gtc atc tgc aag gct ctg gac gac aag aag ctc gga agg ctg ggc     1200
Leu Val Ile Cys Lys Ala Leu Asp Asp Lys Lys Leu Gly Arg Leu Gly
385                 390                 395                 400
```

```
aac atc ttc aag tgc atc gac tac tgc atc aac aag aag gtc aac atc      1248
Asn Ile Phe Lys Cys Ile Asp Tyr Cys Ile Asn Lys Lys Val Asn Ile
            405                 410                 415 atc aac ggc tcc ttc tcc ttc gac gag tac tcc acc atc ttc tcc tcc      1296
Ile Asn Gly Ser Phe Ser Phe Asp Glu Tyr Ser Thr Ile Phe Ser Ser
        420                 425                 430 act atc gag tac ctc gcc cgt ctc ggc atc ctg ttc gtg gtc tcc agc      1344
Thr Ile Glu Tyr Leu Ala Arg Leu Gly Ile Leu Phe Val Val Ser Ser
    435                 440                 445 tcc aac tgc agc cac ccc ccc tcc tcc atc cct gac atc act cgc tgc      1392
Ser Asn Cys Ser His Pro Pro Ser Ser Ile Pro Asp Ile Thr Arg Cys
450                 455                 460 gac ctg tcc gtc aac tcc aag tac ccc tcc gtg ctg tcc acc cag tac      1440
Asp Leu Ser Val Asn Ser Lys Tyr Pro Ser Val Leu Ser Thr Gln Tyr
465                 470                 475                 480 gac aac atg gtg gtg gtc gct aac ctg aag aag aag atc aac ggc gag      1488
Asp Asn Met Val Val Val Ala Asn Leu Lys Lys Lys Ile Asn Gly Glu
                485                 490                 495 tac gac atc tcc atc aac tcc ttc tac tct gac atc tac tgc cag gtc      1536
Tyr Asp Ile Ser Ile Asn Ser Phe Tyr Ser Asp Ile Tyr Cys Gln Val
            500                 505                 510 tcc gct ccc ggc gct aac atc tac tcc acc gct tcc cgc ggt tct tac      1584
Ser Ala Pro Gly Ala Asn Ile Tyr Ser Thr Ala Ser Arg Gly Ser Tyr
        515                 520                 525 atg gag ctg tcc gga act tcc atg gct gcc cct cac gtg gct ggt atc      1632
Met Glu Leu Ser Gly Thr Ser Met Ala Ala Pro His Val Ala Gly Ile
    530                 535                 540 gct tcc atc atc ctg tct atc aac cct gac ctg acc tac aag cag gtg      1680
Ala Ser Ile Ile Leu Ser Ile Asn Pro Asp Leu Thr Tyr Lys Gln Val
545                 550                 555                 560 gtg aac atc ctc aag aac agc gtg gtg aag ctg agc agc cac aag aac      1728
Val Asn Ile Leu Lys Asn Ser Val Val Lys Leu Ser Ser His Lys Asn
                565                 570                 575 aag atc gcc tgg ggt ggt tac atc gac atc ctg aac gct gtc aag aac      1776
Lys Ile Ala Trp Gly Gly Tyr Ile Asp Ile Leu Asn Ala Val Lys Asn
            580                 585                 590 gcc atc tct agc aag aac tct tac atc agg ttc cag ggt atc agg atg      1824
Ala Ile Ser Ser Lys Asn Ser Tyr Ile Arg Phe Gln Gly Ile Arg Met
        595                 600                 605 tgg aag agc aag aag cgt aac gct gct cac cac cac cac cac cac          1869
Trp Lys Ser Lys Lys Arg Asn Ala Ala His His His His His His
    610                 615                 620 taagaattc                                                             1878

<210> SEQ ID NO 8
<211> LENGTH: 623
<212> TYPE: PRT
<213> ORGANISM: Plasmodium berghei

<400> SEQUENCE: 8

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp Pro His Asn Asp Leu Met Asn Lys
        35                  40                  45

Glu Lys Asp Val Gln Lys Ile Ile Glu Asp Leu Arg Phe Leu Glu Lys
    50                  55                  60

Val Asp Ala Ile Leu Glu Asn Ser Asn Met Thr Ile Asp Asp Val Lys
```

```
            65                  70                  75                  80
Ala Asp Ala Asp Ala Tyr Asn Pro Asp Glu Asp Ala Pro Lys Glu Glu
                    85                  90                  95

Leu Asn Lys Ile Glu Met Glu Lys Lys Ala Glu Glu Ala Lys
                100                 105                 110

Asn Ser Lys Lys Lys Ile Leu Glu Arg Tyr Leu Leu Asp Glu Lys Lys
            115                 120                 125

Lys Lys Ser Leu Arg Leu Ile Val Ser Glu Asn His Ala Thr Ser Pro
130                 135                 140

Ser Phe Phe Glu Glu Ser Leu Ile Gln Glu Asp Phe Met Ser Phe Ile
145                 150                 155                 160

Gln Ser Lys Gly Glu Ile Val Asn Leu Lys Asn Leu Lys Ser Met Ile
                165                 170                 175

Ile Glu Leu Asn Ser Asp Met Thr Asp Lys Glu Leu Glu Ala Tyr Ile
                180                 185                 190

Thr Leu Leu Lys Lys Lys Gly Ala His Val Glu Ser Asp Glu Leu Val
            195                 200                 205

Gly Ala Asp Ser Ile Tyr Val Asp Ile Ile Lys Asp Ala Val Lys Arg
210                 215                 220

Gly Asp Thr Ser Ile Asn Phe Lys Lys Met Gln Ser Asn Met Leu Glu
225                 230                 235                 240

Val Glu Asn Lys Thr Tyr Glu Lys Leu Asn Asn Asn Leu Lys Lys Ser
                245                 250                 255

Lys Asn Ser Tyr Lys Lys Ser Phe Phe Asn Asp Glu Tyr Arg Asn Leu
            260                 265                 270

Gln Trp Gly Leu Asp Leu Ala Arg Leu Asp Asp Ala Gln Glu Met Ile
                275                 280                 285

Thr Thr Asn Ser Val Glu Thr Thr Lys Ile Cys Val Ile Asp Ser Gly
            290                 295                 300

Ile Asp Tyr Asn His Pro Asp Leu Lys Gly Asn Ile Tyr Val Asn Leu
305                 310                 315                 320

Asn Glu Leu Asn Gly Lys Glu Gly Ile Asp Asp Asn Asn Gly Ile
                325                 330                 335

Ile Asp Asp Ile Tyr Gly Val Asn Tyr Val Asn Asn Thr Gly Asp Pro
                340                 345                 350

Trp Asp Asp His Asn His Gly Ser His Val Ser Gly Ile Ile Ser Ala
                355                 360                 365

Ile Gly Asn Asn Ser Ile Gly Val Val Gly Val Asn Pro Ser Ser Lys
            370                 375                 380

Leu Val Ile Cys Lys Ala Leu Asp Asp Lys Lys Leu Gly Arg Leu Gly
385                 390                 395                 400

Asn Ile Phe Lys Cys Ile Asp Tyr Cys Ile Asn Lys Lys Val Asn Ile
                405                 410                 415

Ile Asn Gly Ser Phe Ser Phe Asp Glu Tyr Ser Thr Ile Phe Ser Ser
            420                 425                 430

Thr Ile Glu Tyr Leu Ala Arg Leu Gly Ile Leu Phe Val Val Ser Ser
            435                 440                 445

Ser Asn Cys Ser His Pro Pro Ser Ser Ile Pro Asp Ile Thr Arg Cys
450                 455                 460

Asp Leu Ser Val Asn Ser Lys Tyr Pro Ser Val Leu Ser Thr Gln Tyr
465                 470                 475                 480

Asp Asn Met Val Val Val Ala Asn Leu Lys Lys Lys Ile Asn Gly Glu
                485                 490                 495
```

```
Tyr Asp Ile Ser Ile Asn Ser Phe Tyr Ser Asp Ile Tyr Cys Gln Val
            500                 505                 510

Ser Ala Pro Gly Ala Asn Ile Tyr Ser Thr Ala Ser Arg Gly Ser Tyr
        515                 520                 525

Met Glu Leu Ser Gly Thr Ser Met Ala Ala Pro His Val Ala Gly Ile
    530                 535                 540

Ala Ser Ile Ile Leu Ser Ile Asn Pro Asp Leu Thr Tyr Lys Gln Val
545                 550                 555                 560

Val Asn Ile Leu Lys Asn Ser Val Val Lys Leu Ser Ser His Lys Asn
                565                 570                 575

Lys Ile Ala Trp Gly Gly Tyr Ile Asp Ile Leu Asn Ala Val Lys Asn
                580                 585                 590

Ala Ile Ser Ser Lys Asn Ser Tyr Ile Arg Phe Gln Gly Ile Arg Met
            595                 600                 605

Trp Lys Ser Lys Lys Arg Asn Ala Ala His His His His His His
    610                 615                 620

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Leu Val Gly Ala Asp Asp Val Ser Leu Ala
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Val Gly Ala Asp Asp Val Ser Leu Ala Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Leu Val Ser Ala Asp Asn Ile Asp Ile Ser
1               5                   10

<210> SEQ ID NO 12
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Ser Gly Ala Lys Ile Ala Ile Val Asp Thr Gly Val Gln Ser Asn
```

```
1               5                   10                  15
His Pro Asp Leu Asn Gly His Gly Thr His Cys Ala Gly Ile Ala Val
            20                  25                  30

Val Val Ala Ala Ala Gly Asn Ala Gly Asn Ser Leu Ser Gly Thr Ser
        35                  40                  45

Met Ala Thr Pro His Val Ala Gly Val Ala Gly Leu Ile Ala
    50                  55                  60

<210> SEQ ID NO 13
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Ser Gly Gln Glu Ile Ala Val Ile Asp Thr Gly Val Asp Tyr Thr
1               5                   10                  15

His Pro Asp Leu Asn Asn His Gly Thr His Val Ala Gly Ile Ala Val
            20                  25                  30

Val Val Ala Ala Ala Gly Asn Asn Ser Tyr Met Ser Gly Thr Ser Met
        35                  40                  45

Ala Ser Pro His Val Ala Gly Leu Ala Ala Leu Ile Ala
    50                  55                  60

<210> SEQ ID NO 14
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Ser Gly Val Lys Val Ala Ala Val Leu Asp Thr Gly Ile Ser Thr
1               5                   10                  15

His Pro Asp Leu Asn Gly His Gly Thr His Val Ala Gly Thr Ile Leu
            20                  25                  30

Val Val Ala Ala Ser Gly Asn Ser Gly Ala Ser Leu Asn Gly Thr Ser
        35                  40                  45

Met Ala Thr Pro His Val Ala Gly Ala Ala Ala Leu Val Lys
    50                  55                  60

<210> SEQ ID NO 15
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ala Asn Val Lys Val Ala Val Leu Asp Thr Gly Ile Gln Ala Ser
1               5                   10                  15

His Pro Asp Leu Asn Gly His Gly Thr His Val Ala Gly Thr Val Val
            20                  25                  30

Val Val Ala Ala Ala Gly Asn Ser Gly Asn Thr Leu Asn Gly Thr Ser
        35                  40                  45

Met Ala Ser Pro His Val Ala Gly Ala Ala Ala Leu Ile Leu
    50                  55                  60
```

<210> SEQ ID NO 16
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Gly Ser Asn Val Lys Val Ala Val Ile Asp Ser Gly Ile Asp Ser Ser
1               5                   10                  15

His Pro Asp Leu Asn Ser His Gly Thr His Val Ala Gly Thr Val Val
            20                  25                  30

Val Val Ala Ala Ala Gly Asn Glu Gly Thr Ala Tyr Asn Gly Thr Ser
        35                  40                  45

Met Ala Ser Pro His Val Ala Gly Ala Ala Ala Leu Ile Leu
    50                  55                  60

<210> SEQ ID NO 17
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Gly Ser Gly Ile Asn Ile Ala Val Leu Asp Thr Gly Val Asn Thr Ser
1               5                   10                  15

His Pro Asp Leu Asn Gly His Gly Thr His Val Ala Gly Thr Ala Leu
            20                  25                  30

Ile Val Ala Ala Ala Gly Asn Ser Gly Tyr Thr Ile Ser Gly Thr Ser
        35                  40                  45

Met Ala Thr Pro His Val Ser Gly Leu Ala Ala Lys Ile Trp
    50                  55                  60

<210> SEQ ID NO 18
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Gly Gln Gly Ser Cys Val Tyr Val Ile Asp Thr Gly Ile Glu Ala Ser
1               5                   10                  15

His Pro Glu Phe Asn Gly His Gly Thr His Cys Ala Gly Thr Val Met
            20                  25                  30

Val Ala Val Ala Ala Gly Asn Asn Asn Ala Ser Ile Ser Gly Thr Ser
        35                  40                  45

Met Ala Thr Pro His Val Ala Gly Leu Ala Ala Tyr Leu Met
    50                  55                  60

<210> SEQ ID NO 19
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Asn Lys Asn Val Lys Val Cys Val Val Asp Ser Gly Ala Asp Ile Asn
1               5                   10                  15

Arg Val Asp Leu Ser Gly His Gly Thr His Val Thr Gly Ile Ile Val
            20                  25                  30

Leu Ile Ala Ala Ser Gly Asn Lys Ser Asn Ile Phe Thr Gly Thr Ser
        35                  40                  45

Met Ala Ala Pro His Val Cys Gly Val Ser Ala Leu Val Tyr
    50                  55                  60
```

<210> SEQ ID NO 20
<211> LENGTH: 562
<212> TYPE: PRT
<213> ORGANISM: Plasmodium berghei
<220> FEATURE:
<221> NAME/KEY: MOD_RES
<222> LOCATION: (478)..(478)
<223> OTHER INFORMATION: Any naturally occurring amino acid

<400> SEQUENCE: 20

```
Lys Ile Ile Glu Asp Leu Arg Phe Leu Glu Lys Val Asp Ala Ile Leu
1               5                   10                  15

Glu Asn Ser Asn Met Thr Ile Asp Asp Val Lys Ala Asp Ala Asp Ala
            20                  25                  30

Tyr Asn Pro Asp Glu Asp Ala Pro Lys Glu Glu Leu Asn Lys Ile Glu
        35                  40                  45

Met Glu Lys Lys Lys Ala Glu Glu Ala Lys Asn Ser Lys Lys Lys
    50                  55                  60

Ile Leu Glu Arg Tyr Leu Leu Asp Glu Lys Lys Lys Ser Leu Arg
65              70                  75                  80

Leu Ile Val Ser Glu Asn His Ala Thr Ser Pro Ser Phe Phe Glu Glu
                85                  90                  95

Ser Leu Ile Gln Glu Asp Phe Met Ser Phe Ile Gln Ser Lys Gly Glu
            100                 105                 110

Ile Val Asn Leu Lys Asn Leu Lys Ser Met Ile Ile Glu Leu Asn Ser
        115                 120                 125

Asp Met Thr Asp Lys Glu Leu Glu Ala Tyr Ile Thr Leu Leu Lys Lys
    130                 135                 140

Lys Gly Ala His Val Glu Ser Asp Glu Leu Val Gly Ala Asp Ser Ile
145                 150                 155                 160

Tyr Val Asp Ile Ile Lys Asp Ala Val Lys Arg Gly Asp Thr Ser Ile
                165                 170                 175

Asn Phe Lys Lys Met Gln Ser Asn Met Leu Glu Val Glu Asn Lys Thr
            180                 185                 190

Tyr Glu Lys Leu Asn Asn Asn Leu Lys Lys Ser Lys Asn Ser Tyr Lys
        195                 200                 205

Lys Ser Phe Phe Asn Asp Glu Tyr Arg Asn Leu Gln Trp Gly Leu Asp
    210                 215                 220

Leu Ala Arg Leu Asp Asp Ala Gln Glu Met Ile Thr Thr Asn Ser Val
225                 230                 235                 240

Glu Thr Thr Lys Ile Cys Val Ile Asp Ser Gly Ile Asp Tyr Asn His
                245                 250                 255

Pro Asp Leu Lys Gly Asn Ile Tyr Val Asn Leu Asn Glu Leu Asn Gly
            260                 265                 270

Lys Glu Gly Ile Asp Asp Asp Asn Asn Gly Ile Ile Asp Asp Ile Tyr
        275                 280                 285
```

Gly Val Asn Tyr Val Asn Asn Thr Gly Asp Pro Trp Asp His Asn
            290                 295                 300

His Gly Ser His Val Ser Gly Ile Ile Ser Ala Ile Gly Asn Asn Ser
305                 310                 315                 320

Ile Gly Val Val Gly Val Asn Pro Ser Ser Lys Leu Val Ile Cys Lys
                325                 330                 335

Ala Leu Asp Asp Lys Lys Leu Gly Arg Leu Gly Asn Ile Phe Lys Cys
            340                 345                 350

Ile Asp Tyr Cys Ile Asn Lys Lys Val Asn Ile Ile Asn Gly Ser Phe
        355                 360                 365

Ser Phe Asp Glu Tyr Ser Thr Ile Phe Ser Ser Thr Ile Glu Tyr Leu
    370                 375                 380

Ala Arg Leu Gly Ile Leu Phe Val Val Ser Ser Ser Asn Cys Ser His
385                 390                 395                 400

Pro Pro Ser Ser Ile Pro Asp Ile Thr Arg Cys Asp Leu Ser Val Asn
                405                 410                 415

Ser Lys Tyr Pro Ser Val Leu Ser Thr Gln Tyr Asp Asn Met Val Val
            420                 425                 430

Val Ala Asn Leu Lys Lys Ile Asn Gly Glu Tyr Asp Ile Ser Ile
        435                 440                 445

Asn Ser Phe Tyr Ser Asp Ile Tyr Cys Gln Val Ser Ala Pro Gly Ala
    450                 455                 460

Asn Ile Tyr Ser Thr Ala Ser Arg Gly Ser Tyr Met Glu Xaa Ser Gly
465                 470                 475                 480

Thr Ser Met Ala Ala Pro His Val Ala Gly Ile Ala Ser Ile Ile Leu
                485                 490                 495

Ser Ile Asn Pro Asp Leu Thr Tyr Lys Gln Val Val Asn Ile Leu Lys
            500                 505                 510

Asn Ser Val Val Lys Leu Ser Ser His Lys Asn Lys Ile Ala Trp Gly
        515                 520                 525

Gly Tyr Ile Asp Ile Leu Asn Ala Val Lys Asn Ala Ile Ser Ser Lys
    530                 535                 540

Asn Ser Tyr Ile Arg Phe Gln Gly Ile Arg Met Trp Lys Ser Lys Lys
545                 550                 555                 560

Arg Asn

<210> SEQ ID NO 21
<211> LENGTH: 599
<212> TYPE: PRT
<213> ORGANISM: Plasmodium yoelii

<400> SEQUENCE: 21

Met Gly Phe Ser Lys Met Arg Arg Phe Phe Ile Tyr Gly Cys Val Val
1               5                   10                  15

Ser Leu Ala Leu Cys Thr Ile Ser Ala His Asn Asp Leu Met Asn Lys
            20                  25                  30

Glu Lys Asp Val Gln Lys Ile Ile Glu Asp Leu Arg Phe Leu Glu Lys
        35                  40                  45

Val Asp Ala Ile Leu Glu Asn Ser Asn Met Thr Ile Asp Asp Val Glu
    50                  55                  60

Pro Asp Gly Asp Ala Tyr Asn Pro Asp Glu Asp Ala Pro Lys Glu Glu
65                  70                  75                  80

Leu Asn Lys Ile Glu Met Glu Lys Lys Lys Ala Glu Glu Glu Glu Lys
                85                  90                  95

-continued

His Ser Lys Lys Lys Ile Leu Glu Lys Asp Leu Leu Asn Glu Lys Lys
            100                 105                 110

Asn Lys Ser Leu Arg Leu Ile Val Ser Glu Asn His Ala Thr Thr Pro
        115                 120                 125

Ser Phe Phe Glu Glu Ser Ile Ile Gln Glu Asp Phe Met Ser Phe Ile
130                 135                 140

Gln Ser Lys Gly Glu Ile Val Asn Leu Lys Asn Ile Lys Ser Met Ile
145                 150                 155                 160

Ile Glu Leu Asn Ser Asp Met Thr Asp Lys Glu Leu Glu Thr Tyr Ile
                165                 170                 175

Thr Leu Leu Lys Lys Lys Gly Ala His Val Glu Ser Asp Glu Leu Val
            180                 185                 190

Gly Ala Asp Ser Ile Tyr Val Asp Ile Ile Lys Asp Ala Val Lys Arg
        195                 200                 205

Gly Asp Thr Ser Ile Asn Phe Lys Lys Ile Gln Ser Asn Met Leu Glu
210                 215                 220

Val Glu Asn Asn Thr Tyr Glu Lys Ile Asn Asn Lys Leu Glu Lys Ser
225                 230                 235                 240

Lys Asn Ser Asp Lys Lys Ser Tyr Phe Asn Asp Glu Tyr Arg Asn Leu
                245                 250                 255

Gln Trp Gly Leu Asp Leu Ala Arg Leu Asp Asp Ala Gln Glu Met Ile
            260                 265                 270

Thr Thr Asn Ser Val Glu Thr Thr Lys Val Cys Val Ile Asp Ser Gly
        275                 280                 285

Ile Asp Tyr Asn His Pro Asp Leu Lys Gly Asn Ile Tyr Val Asn Leu
290                 295                 300

Lys Glu Leu Asn Gly Lys Pro Gly Val Asp Asp Asn Asn Gly Ile
305                 310                 315                 320

Ile Asp Asp Ile Tyr Gly Ala Asn Tyr Val Asn Asn Thr Gly Asp Pro
                325                 330                 335

Trp Asp Asp His Asn His Gly Thr His Val Ala Gly Ile Ile Ser Ala
            340                 345                 350

Ile Gly Asn Asn Ser Ile Gly Val Val Gly Val Asn Thr Asn Ser Lys
        355                 360                 365

Leu Val Ile Cys Lys Ala Leu Asp Asp Lys Lys Leu Gly Arg Leu Gly
370                 375                 380

Asn Ile Phe Lys Cys Ile Asp Tyr Cys Ile Asn Asn Lys Ala Asn Ile
385                 390                 395                 400

Ile Asn Gly Ser Phe Ser Phe Asp Glu Tyr Ser Thr Val Phe Ser Ser
                405                 410                 415

Thr Ile Glu Tyr Leu Gly Arg Leu Gly Ile Leu Phe Val Val Ser Ser
            420                 425                 430

Ser Asn Cys Ser His Pro Thr Ser Ser Ile Pro Asp Ile Thr Arg Cys
        435                 440                 445

Asp Leu Ser Val Asn Ser Lys Tyr Pro Ser Val Leu Ser Thr Gln Tyr
450                 455                 460

Asp Asn Val Val Val Ala Asn Leu Lys Lys Lys Asn Gly Glu
465                 470                 475                 480

Tyr Asp Val Ser Ile Asn Ser Phe Tyr Ser Asp Ile Tyr Cys Gln Val
                485                 490                 495

Ser Ala Pro Gly Ala Asn Ile Tyr Ser Thr Ala Thr Arg Gly Ser Tyr
            500                 505                 510

```
Leu Glu Leu Ser Gly Thr Ser Met Ala Ala Pro His Val Ala Gly Ile
            515                 520                 525

Ala Ser Ile Ile Leu Ser Ile Asn Pro Glu Leu Thr Tyr Lys Gln Val
        530                 535                 540

Val Ser Ile Leu Lys Asn Ser Val Val Lys Leu Ser Ser His Lys Asn
545                 550                 555                 560

Lys Ile Ala Trp Gly Gly Tyr Ile Asp Ile Leu Lys Ala Val Lys Asn
                565                 570                 575

Ala Ile Ser Ser Lys Asn Ser Tyr Ile Arg Phe Gln Gly Ile Ser Ile
                580                 585                 590

Trp Lys Asn Lys Lys Arg Asn
        595

<210> SEQ ID NO 22
<211> LENGTH: 619
<212> TYPE: PRT
<213> ORGANISM: Plasmodium vivax

<400> SEQUENCE: 22

Met Val Leu Thr Arg Arg Ala Ala Leu Leu Leu Cys Pro Trp Val Ile
1               5                   10                  15

Gln Leu Val Ile Lys Arg Thr Leu Ala Gly Asp Ile Leu Pro Asn Glu
            20                  25                  30

Gly Lys Lys Glu Lys Asp Asp Val His Lys Ile Ile Ser Glu Leu Arg
        35                  40                  45

Phe Leu Gln Lys Val Glu Thr Ile Leu Glu Ser Ser Asn Met Ser Val
    50                  55                  60

Ser Asp Val Glu Ala Asp Ala Asn Ala Tyr Asn Pro Asp Arg Asp Ala
65                  70                  75                  80

Pro Lys Glu Glu Leu Gln Lys Leu Gln Asp Gln Gln Glu Thr Pro Ser
                85                  90                  95

Lys Glu Pro Asn Asn Leu Arg Asn Ser Pro Gln Lys Arg Ala Glu Lys
            100                 105                 110

Lys Glu Ser Pro Gly Lys Asn Lys Ser Leu Arg Leu Ile Val Ser
        115                 120                 125

Glu Asn His Ala Thr Ser Pro Ser Phe Phe Glu Glu Ser Leu Leu Gln
    130                 135                 140

Glu Asp Val Val Ser Phe Ile Gln Ser Lys Gly Lys Leu Ser Asn Leu
145                 150                 155                 160

Lys Asn Leu Lys Ser Met Ile Ile Asp Leu Asn Ser Asp Met Thr Asp
                165                 170                 175

Glu Glu Leu Ala Glu Tyr Ile Ser Leu Leu Glu Arg Lys Gly Ala Leu
            180                 185                 190

Ile Glu Ser Asp Lys Leu Val Gly Ala Asp Val Ser Leu Ala Ser
        195                 200                 205

Val Lys Asp Ala Val Arg Arg Gly Glu Ser Ser Val Asn Trp Gly Lys
    210                 215                 220

Leu Arg Ser Thr Met Leu Glu Val Pro Ser Gly Glu Ser Pro Pro Ser
225                 230                 235                 240

His Ala Ala Ser Ser Gly Ser Pro Phe Asp Asp Asp Asp Leu Leu
                245                 250                 255

Ser Glu Ala Ala Leu His Arg Glu Glu Ala His Leu Ala Gly Ser Lys
            260                 265                 270

Thr Thr Lys Gly Tyr Lys Phe Asn Asp Glu Tyr Arg Asn Leu Gln Trp
        275                 280                 285
```

Gly Leu Asp Leu Ala Arg Leu Asp Glu Thr Gln Asp Leu Ile Asn Ala
    290                 295                 300

Asn Arg Val Ser Val Thr Lys Ile Cys Val Ile Asp Ser Gly Ile Asp
305                 310                 315                 320

Tyr Asn His Pro Asp Leu Arg Asn Asn Ile Asp Val Asn Val Lys Glu
                325                 330                 335

Leu His Gly Arg Lys Gly Val Asp Asp Ser Asn Gly Val Val Asp
            340                 345                 350

Asp Val Tyr Gly Ala Asn Phe Val Asn Asn Ser Gly Asp Pro Met Asp
        355                 360                 365

Asp Asn Tyr His Gly Thr His Val Ser Gly Ile Ile Ser Ala Val Gly
370                 375                 380

Asn Asn Gly Ile Gly Ile Val Gly Val Asp Gly His Ser Lys Leu Val
385                 390                 395                 400

Ile Cys Lys Ala Leu Asp Gln His Lys Leu Gly Arg Leu Gly Asp Met
                405                 410                 415

Ala His Met Ile Asn Gly Ser Phe Ser Phe Asp Glu Tyr Ser Asn Ile
            420                 425                 430

Phe Asn Ala Ser Val Glu His Leu Arg Ser Leu Gly Ile Leu Phe Phe
        435                 440                 445

Val Ser Ala Ser Asn Cys Ala His Asp Lys Leu Ser Lys Pro Asp Ile
450                 455                 460

Ala Lys Cys Asp Leu Ala Val Asn His Arg Tyr Pro Pro Ile Leu Ser
465                 470                 475                 480

Lys Thr His Asn Asn Val Ile Ala Val Ala Asn Leu Lys Arg Asp Leu
                485                 490                 495

Asp Glu Ser Tyr Ser Leu Ser Val Asn Ser Phe Tyr Ser Asn Ile Tyr
            500                 505                 510

Cys Gln Leu Ala Ala Pro Gly Thr Asn Ile Tyr Ser Thr Thr Pro Met
        515                 520                 525

Asn Asn Tyr Arg Lys Leu Asn Gly Thr Ser Met Ala Ser Pro His Val
530                 535                 540

Ala Ala Ile Ala Ser Ile Val Arg Ser Ile Asn Pro Asn Leu Thr Tyr
545                 550                 555                 560

Leu Gln Ile Val Glu Ile Leu Arg Asn Ala Ile Val Lys Leu Pro Ser
                565                 570                 575

Leu Thr Glu Arg Val Ser Trp Gly Gly Tyr Val Asp Ile Leu Arg Ala
            580                 585                 590

Val Asn Leu Ala Ile Asp Ser Lys Ala Ala Pro Tyr Ile Lys Ser His
        595                 600                 605

Ser Trp Phe Arg Trp Lys Gln Gly Ser Arg Arg
610                 615

<210> SEQ ID NO 23
<211> LENGTH: 688
<212> TYPE: PRT
<213> ORGANISM: Plasmodium falciparum

<400> SEQUENCE: 23

Met Met Leu Asn Lys Lys Val Val Ala Leu Cys Thr Leu Thr Leu His
1               5                   10                  15

Leu Phe Cys Ile Phe Leu Cys Leu Gly Lys Glu Val Arg Ser Glu Glu
            20                  25                  30

Asn Gly Lys Ile Gln Asp Asp Ala Lys Lys Ile Val Ser Glu Leu Arg

```
               35                  40                  45
Phe Leu Glu Lys Val Glu Asp Val Ile Glu Lys Ser Asn Ile Gly Gly
 50                  55                  60

Asn Glu Val Asp Ala Asp Glu Asn Ser Phe Asn Pro Asp Thr Glu Val
 65                  70                  75                  80

Pro Ile Glu Glu Ile Glu Ile Lys Met Arg Glu Leu Lys Asp Val
                     85                  90                  95

Lys Glu Glu Lys Asn Lys Asn Asp Asn His Asn Asn Asn Asn Asn Asn
                100                 105                 110

Ile Ser Ser Ser Ser Ser Ser Ser Asn Thr Phe Gly Glu Glu Lys
            115                 120                 125

Glu Glu Val Ser Lys Lys Lys Lys Leu Arg Leu Ile Val Ser Glu
        130                 135                 140

Asn His Ala Thr Thr Pro Ser Phe Phe Gln Ser Leu Leu Glu Pro
145                 150                 155                 160

Asp Val Leu Ser Phe Leu Glu Ser Lys Gly Asn Leu Ser Asn Leu Lys
                    165                 170                 175

Asn Ile Asn Ser Met Ile Ile Glu Leu Lys Glu Asp Thr Thr Asp Asp
                180                 185                 190

Glu Leu Ile Ser Tyr Ile Lys Ile Leu Glu Glu Lys Gly Ala Leu Ile
            195                 200                 205

Glu Ser Asp Lys Leu Val Ser Ala Asp Asn Ile Asp Ile Ser Gly Ile
        210                 215                 220

Lys Asp Ala Ile Arg Arg Gly Glu Glu Asn Ile Asp Val Asn Asp Tyr
225                 230                 235                 240

Lys Ser Met Leu Glu Val Asn Asp Ala Glu Asp Tyr Asp Lys Met
                    245                 250                 255

Phe Gly Met Phe Asn Glu Ser His Ala Ala Thr Ser Lys Arg Lys Arg
                260                 265                 270

His Ser Thr Asn Glu Arg Gly Tyr Asp Thr Phe Ser Ser Pro Ser Tyr
            275                 280                 285

Lys Thr Tyr Ser Lys Ser Asp Tyr Leu Tyr Asp Asp Asn Asn Asn
        290                 295                 300

Asn Asn Tyr Tyr Tyr Ser His Ser Ser Asn Gly His Asn Ser Ser Ser
305                 310                 315                 320

Arg Asn Ser Ser Ser Arg Ser Arg Pro Gly Lys Tyr His Phe Asn
                    325                 330                 335

Asp Glu Phe Arg Asn Leu Gln Trp Gly Leu Asp Leu Ser Arg Leu Asp
                340                 345                 350

Glu Thr Gln Glu Leu Ile Asn Glu His Gln Val Met Ser Thr Arg Ile
            355                 360                 365

Cys Val Ile Asp Ser Gly Ile Asp Tyr Asn His Pro Asp Leu Lys Asp
        370                 375                 380

Asn Ile Glu Leu Asn Leu Lys Glu Leu His Gly Arg Lys Gly Phe Asp
385                 390                 395                 400

Asp Asp Asn Asn Gly Ile Val Asp Ile Tyr Gly Ala Asn Phe Val
                    405                 410                 415

Asn Asn Ser Gly Asn Pro Met Asp Asp Asn Tyr His Gly Thr His Val
                420                 425                 430

Ser Gly Ile Ile Ser Ala Ile Gly Asn Asn Ile Gly Val Val Gly
            435                 440                 445

Val Asp Val Asn Ser Lys Leu Ile Ile Cys Lys Ala Leu Asp Glu His
        450                 455                 460
```

Lys Leu Gly Arg Leu Gly Asp Met Phe Lys Cys Leu Asp Tyr Cys Ile
465                 470                 475                 480

Ser Arg Asn Ala His Met Ile Asn Gly Ser Phe Ser Phe Asp Glu Tyr
                485                 490                 495

Ser Gly Ile Phe Asn Ser Ser Val Glu Tyr Leu Gln Arg Lys Gly Ile
            500                 505                 510

Leu Phe Phe Val Ser Ala Ser Asn Cys Ser His Pro Lys Ser Ser Thr
            515                 520                 525

Pro Asp Ile Arg Lys Cys Asp Leu Ser Ile Asn Ala Lys Tyr Pro Pro
        530                 535                 540

Ile Leu Ser Thr Val Tyr Asp Asn Val Ile Ser Val Ala Asn Leu Lys
545                 550                 555                 560

Lys Asn Asp Asn Asn His Tyr Ser Leu Ser Ile Asn Ser Phe Tyr
                565                 570                 575

Ser Asn Lys Tyr Cys Gln Leu Ala Ala Pro Gly Thr Asn Ile Tyr Ser
            580                 585                 590

Thr Ala Pro His Asn Ser Tyr Arg Lys Leu Asn Gly Thr Ser Met Ala
        595                 600                 605

Ala Pro His Val Ala Ala Ile Ala Ser Leu Ile Phe Ser Ile Asn Pro
    610                 615                 620

Asp Leu Ser Tyr Lys Lys Val Ile Gln Ile Leu Lys Asp Ser Ile Val
625                 630                 635                 640

Tyr Leu Pro Ser Leu Lys Asn Met Val Ala Trp Ala Gly Tyr Ala Asp
                645                 650                 655

Ile Asn Lys Ala Val Asn Leu Ala Ile Lys Ser Lys Lys Thr Tyr Ile
            660                 665                 670

Asn Ser Asn Ile Ser Asn Lys Trp Lys Lys Lys Ser Arg Tyr Leu His
        675                 680                 685

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp His Asn Ser
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Val Ser Leu Ala
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Lys Leu Val Gly Ala Asp
1               5
```